US011015187B2

(12) United States Patent
Gundling

(10) Patent No.: US 11,015,187 B2
(45) Date of Patent: *May 25, 2021

(54) PURIFICATION OF NUCLEIC ACIDS USING COPPER-TITANIUM OXIDES

(71) Applicant: ABBOTT MOLECULAR INC., Des Plaines, IL (US)

(72) Inventor: Gerard J. Gundling, Des Plaines, IL (US)

(73) Assignee: ABBOTT MOLECULAR INC., Des Plaines, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/692,820

(22) Filed: Nov. 22, 2019

(65) Prior Publication Data

US 2020/0087655 A1 Mar. 19, 2020

Related U.S. Application Data

(60) Division of application No. 16/503,874, filed on Jul. 5, 2019, now Pat. No. 10,526,596, which is a continuation of application No. 15/209,318, filed on Jul. 13, 2016, now Pat. No. 10,392,613.

(60) Provisional application No. 62/192,444, filed on Jul. 14, 2015.

(51) Int. Cl.
*C12N 15/10* (2006.01)
*C01G 23/00* (2006.01)
*C07H 1/08* (2006.01)

(52) U.S. Cl.
CPC ......... *C12N 15/1006* (2013.01); *C01G 23/00* (2013.01); *C07H 1/08* (2013.01); *C01P 2004/61* (2013.01); *C01P 2004/62* (2013.01)

(58) Field of Classification Search
CPC ....... C12N 15/1006; C01G 23/00; C07H 1/08
See application file for complete search history.

(56) References Cited

U.S. PATENT DOCUMENTS

| 5,283,174 A | 2/1994 | Arnold et al. |
| 5,491,224 A | 2/1996 | Bittner et al. |
| 5,539,256 A | 7/1996 | Mikagi |
| 5,695,934 A | 12/1997 | Brenner |
| 5,714,330 A | 2/1998 | Brenner et al. |
| 5,750,341 A | 5/1998 | Macevicz |
| 5,776,688 A | 7/1998 | Bittner et al. |
| 5,817,798 A | 10/1998 | Gundling |
| 5,912,148 A | 6/1999 | Eggerding |
| 6,130,073 A | 10/2000 | Eggerding |
| 6,210,891 B1 | 4/2001 | Nyren et al. |
| 6,258,568 B1 | 7/2001 | Nyren |
| 6,306,597 B1 | 10/2001 | Macevicz |
| 6,432,360 B1 | 8/2002 | Church |
| 6,485,944 B1 | 11/2002 | Church et al. |
| 6,511,803 B1 | 1/2003 | Church et al. |
| 6,787,308 B2 | 9/2004 | Balasubramanian et al. |
| 6,818,395 B1 | 11/2004 | Quake et al. |
| 6,833,246 B2 | 12/2004 | Balasubramanian |
| 6,897,027 B2 | 5/2005 | Smarason et al. |
| 6,911,345 B2 | 6/2005 | Quake et al. |
| 6,936,414 B2 | 8/2005 | Gundling |
| 6,969,488 B2 | 11/2005 | Bridgham et al. |
| 7,115,400 B1 | 10/2006 | Adessi et al. |
| 7,169,560 B2 | 1/2007 | Lapidus et al. |
| 7,282,337 B1 | 10/2007 | Harris |
| 7,329,492 B2 | 2/2008 | Hardin et al. |
| 7,482,120 B2 | 1/2009 | Buzby |
| 2002/0068821 A1 | 6/2002 | Gundling |
| 2005/0130173 A1 | 6/2005 | Leamon et al. |
| 2006/0177855 A1 | 8/2006 | Utermohlen et al. |
| 2006/0223071 A1 | 10/2006 | Wisniewski et al. |
| 2007/0238114 A1 | 10/2007 | Lee et al. |
| 2007/0250274 A1 | 10/2007 | Volkov et al. |
| 2008/0241951 A1 | 10/2008 | Battulga et al. |
| 2009/0026082 A1 | 1/2009 | Rothberg et al. |
| 2009/0035777 A1 | 2/2009 | Kokoris et al. |
| 2009/0127589 A1 | 5/2009 | Rothberg et al. |
| 2009/0182120 A1 | 7/2009 | Utermohlen et al. |
| 2010/0137143 A1 | 6/2010 | Rothberg et al. |
| 2010/0188073 A1 | 7/2010 | Rothberg et al. |
| 2010/0197507 A1 | 8/2010 | Rothberg et al. |
| 2010/0207051 A1 | 8/2010 | Fonnum et al. |
| 2010/0301398 A1 | 12/2010 | Rothberg et al. |
| 2012/0059160 A1 | 3/2012 | Bitner et al. |
| 2013/0158247 A1 | 6/2013 | Fabis et al. |
| 2017/0081655 A1 | 3/2017 | Gundling |
| 2019/0345481 A1 | 11/2019 | Gundling |

FOREIGN PATENT DOCUMENTS

| DE | 19854973 | 5/2000 |
| EP | 1842914 A1 | 10/2007 |
| WO | WO199218514 | 10/1992 |
| WO | WO2000018957 | 4/2000 |

(Continued)

OTHER PUBLICATIONS

Examination Report issued in corresponding EP Patent Application No. 16825099.1, dated Jan. 8, 2020, 6 pages.
Adessi et al., "Solid phase DNA amplification: characterisation of primer attachment and amplification mechanisms." Nucleic Acids Res. Oct. 15, 2000;28(20):E87.
Astier et al., "Toward single molecule DNA sequencing: direct identification of ribonucleoside and deoxyribonucleoside 5'-monophosphates by using an engineered protein nanopore equipped with a molecular adapter." J Am Chem Soc. Feb. 8, 2006;128(5):1705-10.
Bennett et al., "Toward the 1,000 dollars human genome." Pharmacogenomics. Jun. 2005;6(4):373-82.
Birren B., et al., eds., Genome Analysis—A Laboratory Manual, vol. 1, Cold Spring Harbor Laboratory Press, 1997, Table of Contents.
Brenner et al., "Gene expression analysis by massively parallel signature sequencing (MPSS) on microbead arrays." Nat Biotechnol. Jun. 2000;18(6):630-4.

(Continued)

*Primary Examiner* — Kenneth R Horlick
(74) *Attorney, Agent, or Firm* — Casimir Jones, S.C.; Kirk Hogan

(57) ABSTRACT

The present disclosure relates to systems and methods for purifying nucleic acid. In particular, the present disclosure relates to systems and methods for purifying nucleic acids using metal or metal oxide compositions.

13 Claims, 76 Drawing Sheets

(56) References Cited

FOREIGN PATENT DOCUMENTS

| WO | WO2006084132 | 8/2006 |
|---|---|---|
| WO | WO2011151428 | 12/2011 |
| WO | WO2014144209 | 9/2014 |
| WO | WO2017011538 | 1/2017 |

OTHER PUBLICATIONS

Margulies et al., "Genome sequencing in microfabricated high-density picolitre reactors." Nature. Sep. 15, 2005;437(7057):376-80.

Maclean et al., "Application of 'next-generation' sequencing technologies to microbial genetics." Nat Rev Microbiol. Apr. 2009;7(4):287-96.

Mitra et al., "Fluorescent in situ sequencing on polymerase colonies." Anal Biochem. Sep. 1, 2003;320(1):55-65.

Morozova et al., "Applications of next-generation sequencing technologies in functional genomics." Genomics. Nov. 2008;92(5):255-64.

Morrison et al., "Labeling fluorescence in situ hybridization probes for genomic targets." Methods Mol Biol. 2002;204:21-40.

Nelson N.C., et al., "Detection of Acridinium Esters by Chemiluminescence," in: Nonisotopic Probing, Blotting and Sequencing, 1995, Chapter 17, Academic Press, Inc., pp. 391-428.

Pennisi "Genomics. Semiconductors inspire new sequencing technologies." Science. Mar. 5, 2010;327(5970):1190.

Qiagen RNeasy Plus Universal Handbook. Dec. 2014, 66 pages.

Shendure et al., "Accurate multiplex polony sequencing of an evolved bacterial genome." Science. Sep. 9, 2005;309(5741):1728-32.

Supplementary EP Search Report issued in corresponding EP Application No. 16825099.1, dated Dec. 20, 2018, 6 pages.

Search Report of Related PCT/US2016/042065, dated Oct. 4, 2016, 13 pages.

Voelkerding et al., "Next-generation sequencing: from basic research to diagnostics." Clin Chem. Apr. 2009;55(4):641-58.

PURIFICATION OF NUCLEIC ACIDS USING COPPER-TITANIUM OXIDES

CROSS-REFERENCE TO RELATED APPLICATIONS

This application is a divisional of U.S. patent application Ser. No. 16/503,874, filed Jul. 5, 2019, now U.S. Pat. No. 10,526,596, issued Jan. 7, 2020, which is a continuation of U.S. patent application Ser. No. 15/209,318, filed Jul. 13, 2016, now U.S. Pat. No. 10,392,613, issued Aug. 27, 2019, which claims priority to U.S. Provisional Application Ser. No. 62/192,444 filed Jul. 14, 2015, the entirety of which is incorporated by reference herein.

TECHNICAL FIELD

The present disclosure relates to systems and methods for purifying nucleic acid. In particular, the present disclosure relates to systems and methods for purifying nucleic acids using metal or metal oxide compositions.

BACKGROUND

Nucleic acids found in cells can be deoxyribonucleic acid or ribonucleic acid and can be genomic DNA, extrachromosomal DNA (e.g. plasmids and episomes), mitochondrial DNA, messenger RNA, miRNA, and transfer RNA. Nucleic acids can also be foreign to the host and contaminate a cell as an infectious agent, e.g. bacteria, viruses, fungi or single celled organisms and infecting multicellular organisms (parasites). Recently, detection and analysis of the presence of nucleic acids has become important for the identification of single nucleotide polymorphisms (SNPs), chromosomal rearrangements, the insertion of foreign genes, and alterations in methylation status of nucleic acids. These include infectious viruses, e.g. HIV and other retroviruses, jumping genes, e.g. transposons, and the identification of nucleic acids from recombinantly engineered organisms containing foreign genes, e.g. Roundup Ready plants.

The analysis of nucleic acids has a wide array of uses. For example, the presence of a foreign agent can be used as a medical diagnostic tool. The identification of the genetic makeup of cancerous tissues can also be used as a medical diagnostic tool, confirming that a tissue is cancerous, and determining the aggressive nature of the cancerous tissue. Chromosomal rearrangements, SNPs and abnormal variations in gene expression can be used as a medical diagnostic for particular disease states. Further, genetic information can be used to ascertain the effectiveness of particular pharmaceutical drugs, known as the field of pharmacogenomics.

While many nucleic acid purification procedures are well known and have been in existence for years, these procedures can be time consuming and may employ reagents that present dangers to those performing the purification. For example, it has long been known that DNA can readily be obtained in a purified form from a test sample using organic extraction procedures, but such procedures can require several extractions and therefore can be time consuming. Additionally, the use of some organic solvents is undesirable and dangerous if proper precautions are not followed.

Accordingly, there is a need for an efficient, effective and convenient method for isolating nucleic acids preparing cell-free nucleic acids for analysis.

SUMMARY

The present disclosure relates to systems and methods for purifying nucleic acid. In particular, the present disclosure relates to systems and methods for purifying nucleic acids using metal or metal oxide compositions.

For example, in some embodiments, the present disclosure provides a method of capturing DNA and/or RNA from a biological sample, comprising: a) contacting the sample with a particle and/or solid support comprising or coated with a metal or metal oxide such that DNA and/or RNA in the sample binds the particle or solid support; b) washing the particle or solid support to remove contaminants; and c) eluting the DNA and/or RNA from the particle or solid support. In some embodiments, the metal oxide is CuTi. The present disclosure in not limited to particular amounts of copper and titanium. In some embodiments, the CuTi is present at a ratio of approximately 2:1 Cu to Ti (e.g., 3:1, 2:1, 1:1, 1:2, 1:3, etc.). In some embodiments, the metal or metal oxide is AlTi, CaTi, CoTi, $Fe_2Ti$, $Fe_3Ti$, MgTi, MnTi, NiTi, SnTi, ZnTi, $Fe_2O_3$, $Fe_3O_4$, Mg, Mn, Sn, Ti, or Zn (e.g., anhydride or hydrated forms). In some embodiments, the particles have a diameter of 0.3 to 2 μm (e.g., 0.5 μm, 1.0 μm, 1.5 μm, 2.0 μm, 5.0 μm, 10.0 μm, 20.0 μm, 30.0 μm, 40.0 μm, 50.0 μm, etc.). In some embodiments, the particles or solid surface are magnetic (e.g., paramagnetic, or ferromagnetic) (e.g. iron), metallic, an inorganic solid (e.g., silica), a polymer, or a combination thereof. In some embodiments, the solid surface or particles have a planer, acicular, cuboidal, tubular, fibrous, columnar or amorphous shape. In some embodiments, the particles preferentially bind DNA (e.g. single or double stranded DNA) or RNA, depending on the metal or metal oxide. In some embodiments, the method further comprises the step of eluting DNA and/or RNA from the particles. In some embodiments, the elution comprises an elution buffer. In some embodiments, the elution buffer comprises phosphate (e.g., an inorganic phosphate or an organophosphate) at a concentration of 0.5 to 20 mM (e.g. 1, 2, 3, 4, 5, 6, 7, 8, 9, or 10 mM). In some embodiments, the elution buffer is at a concentration higher than 10 mM and is diluted to a lower concentration after the sample has been eluted. In some embodiments, the elution buffer is at a concentration higher than 10 mM and a small volume is used in the assay to prevent inhibition. In some embodiments, the RNA and/or DNA is viral, eukaryotic, or prokaryotic RNA and/or DNA (e.g., from a pathogen). In some embodiments, particles do not substantially bind DNA.

In some embodiments, the method further comprises the step of determining the identity and/or amount of the RNA present in the sample (e.g., using one or more detection methods selected from, for example, amplification, hybridization, or sequencing).

Further embodiments provide systems and/or kits, comprising a) a particle and/or solid support comprising or coated with a metal oxide; and b) an elution buffer. In some embodiments, kits further comprise one or more reagents selected from, for example, one or more nucleic acid primers and one or more nucleic acid probes, controls, instructions, buffers (e.g., binding and/or wash buffers), etc.

Additional embodiments provide a method of capturing RNA from a biological sample, comprising: a) contacting the sample with a particle and/or solid support comprising or coated with a metal oxide such that RNA in the sample binds the particle but not DNA in the sample; b) washing the particle to remove contaminants; and c) eluting the RNA from the particle. In some embodiments, the particles bind less than 20% (e.g., less than 19%, 18%, 17%, 16%, 15%, 14%, 13%, 12%, 11%, 10%, 9%, 8%, 7%, 6%, 5%, 4%, 3%, 2%, or 1%) of DNA in the sample. In some embodiments, the DNA is genomic, bacterial, and/or viral DNA.

Further embodiments provide the use of the kits or particles described herein to purify RNA.

Additional embodiments are described herein.

DETAILED DESCRIPTION

Figure 1A:
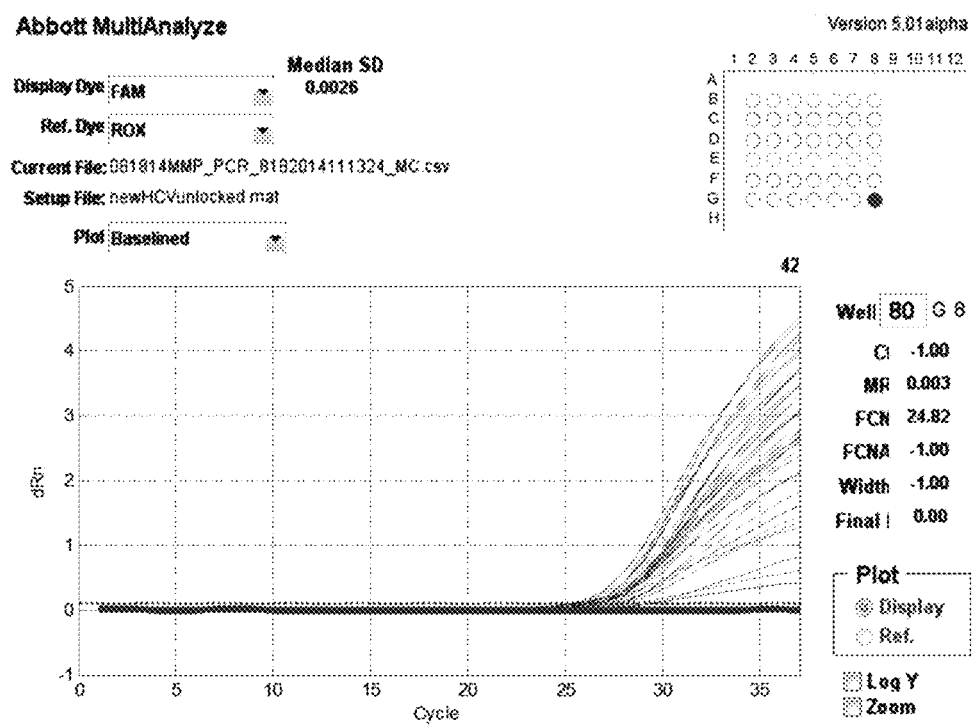
FIGS. 1A-D shows statistical analysis of RNA binding by CuTi particles.
Figure 1B:
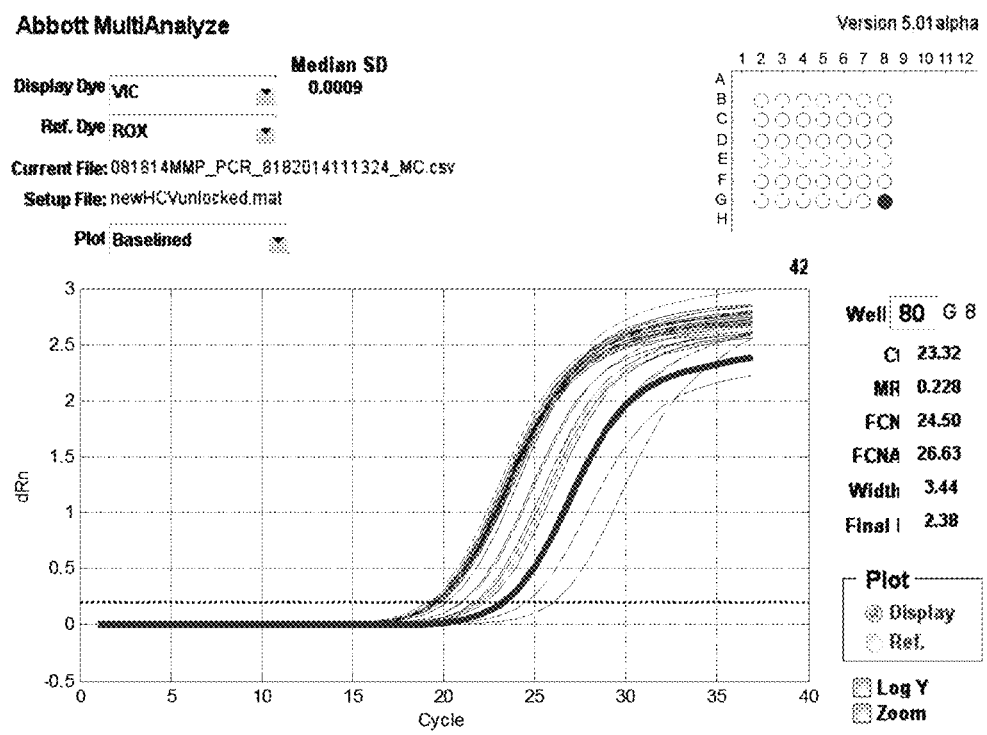
Figure 1C:
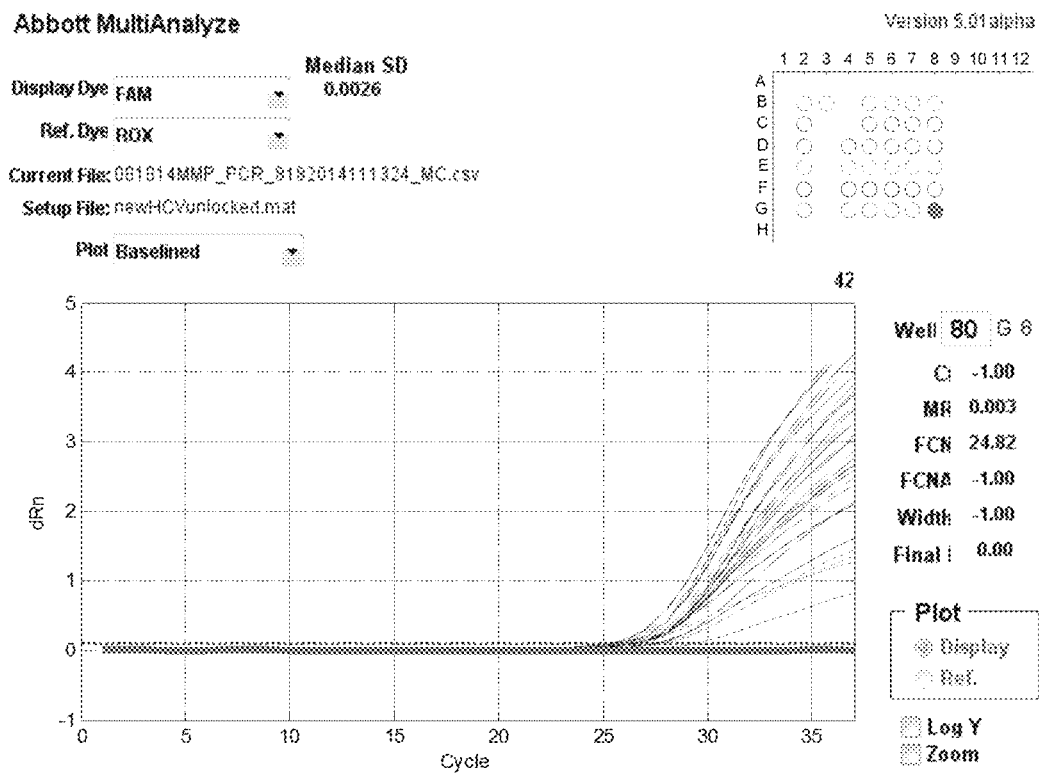
Figure 1D:
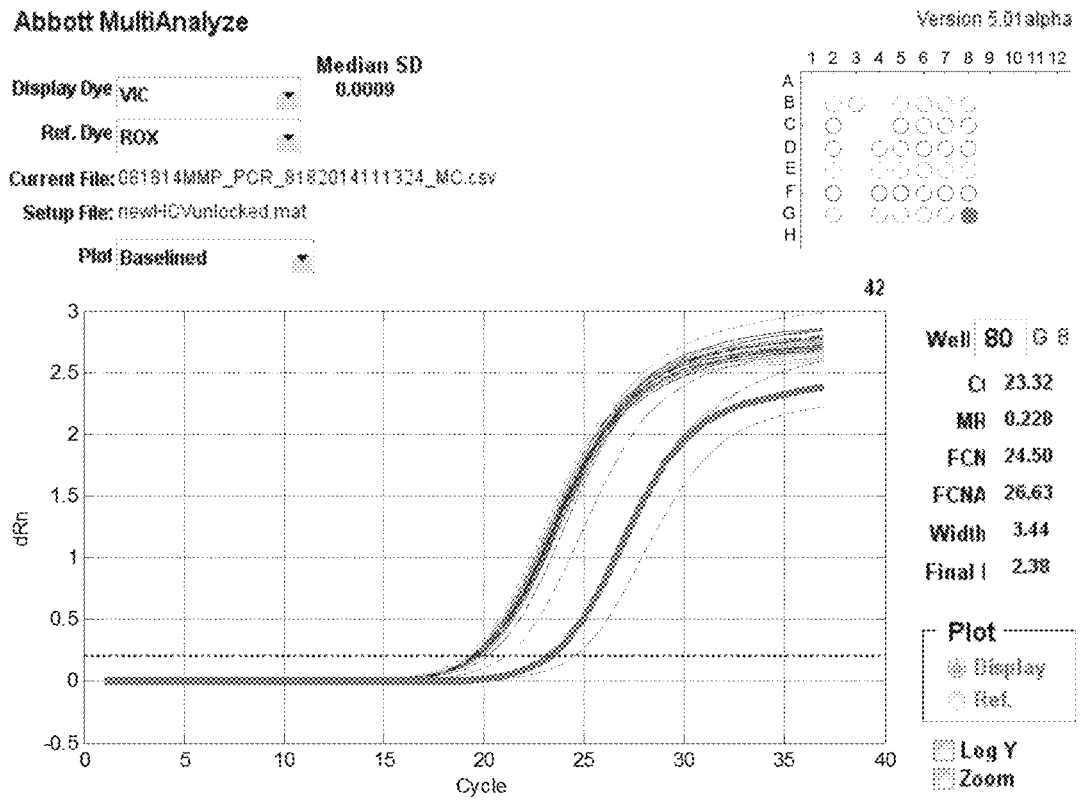

The present disclosure relates to systems and methods for purifying nucleic acid. In particular, the present disclosure relates to systems and methods for purifying nucleic acids using metal or metal oxide compositions.

Definitions

To facilitate an understanding of the present technology, a number of terms and phrases are defined below. Additional definitions are set forth throughout the detailed description.

As used herein, "a" or "an" or "the" can mean one or more than one. For example, "a" widget can mean one widget or a plurality of widgets.

A "blood-borne microorganism" is intended to encompass any microorganism that can be found in blood. Examples of blood-borne microorganisms include bacteria, viruses, fungi, and parasites.

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5 (carboxyhydroxyl¬methyl) uracil, 5-fluorouracil, 5 bromouracil, 5-carboxymethylaminomethyl 2 thiouracil, 5 carboxymethyl¬aminomethyluracil, dihydrouracil, inosine, N6 isopentenyladenine, 1 methyladenine, 1-methylpseudo¬uracil, 1 methylguanine, 1 methylinosine, 2,2-dimethyl¬guanine, 2 methyladenine, 2 methylguanine, 3-methyl¬cytosine, 5 methylcytosine, N6 methyladenine, 7 methylguanine, 5 methylaminomethyluracil, 5-methoxy¬amino¬methyl 2 thiouracil, beta D mannosylqueosine, 5' methoxycarbonylmethyluracil, 5 methoxyuracil, 2 methylthio N6 isopentenyladenine, uracil 5 oxyacetic acid methylester, uracil 5 oxyacetic acid, oxybutoxosine, pseudouracil, queosine, 2 thiocytosine, 5-methyl-2 thiouracil, 2-thiouracil, 4 thiouracil, 5-methyluracil, N-uracil 5 oxyacetic acid methylester, uracil 5 oxyacetic acid, pseudouracil, queosine, 2-thiocytosine, and 2,6 diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment is retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "amplifying" or "amplification" in the context of nucleic acids refers to the production of multiple copies of a polynucleotide, or a portion of the polynucleotide, typically starting from a small amount of the polynucleotide (e.g., as few as a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR) are forms of amplification. Amplification is not limited to the strict duplication of the starting molecule. For example, the generation of multiple cDNA molecules from a limited amount of RNA in a sample using reverse transcription (RT)-PCR is a form of amplification. Furthermore, the generation of multiple RNA molecules from a single DNA molecule during the process of transcription is also a form of amplification.

As used herein, the term "particles" refers to a substrate or other solid material that does not dissolve in aqueous solutions utilized in nucleic acid purification or isolation. For example, in some embodiments, particles are substrates utilized in nucleic acid purification and isolation. Examples include, but are not limited to, beads, spheres, or other shaped particles. In some embodiments, particles are coated or functionalized with material that enhances nucleic acid binding (e.g., CuTi compounds).

As used herein, the terms "subject" and "patient" refer to any animal, such as a dog, a cat, a bird, livestock, and particularly a mammal, and preferably a human.

As used herein, the term "sample" is used in its broadest sense. In one sense, it is meant to include a representative portion or culture obtained from any source, including biological and environmental sources. Biological samples may be obtained from animals (including humans) and encompass fluids, solids, tissues, and gases. Biological samples include blood products, such as plasma, serum, and the like. In some embodiments, samples comprise cells (e.g., tumor cells) or tissues (e.g., tumor or biopsy tissues) or nucleic acids (e.g., DNA or RNA) isolated from such cells or tissues. Environmental samples include environmental material such as surface matter, soil, mud, sludge, biofilms, water, and industrial samples. Such examples are not however to be construed as limiting the sample types applicable to the present disclosure.

As used herein, the term "substantially bind" as in reference to particles that do not substantially bind DNA, refers to particles that bind DNA at a low level (e.g., relative to the level of RNA bound by the particles). In some embodiments, particles that do not substantially bind DNA have a higher affinity for RNA than DNA. For example, in some embodiments, particles bind less than 30%, 25%, 20%, 15%, 10%, or 5% as much DNA as RNA. In some embodiments, particles have a decreased affinity for DNA relative to RNA (e.g., decreased by 20%, 30%, 40%, 50%, 60%, 70%, 80%, 90% or more).

Embodiments of the Technology

Although the disclosure herein refers to certain illustrated embodiments, it is to be understood that these embodiments are presented by way of example and not by way of limitation.

Embodiments of the present disclosure provide metal (e.g., CuTi or other Ti particles) for use in purification of RNA. For example, in some embodiments, particles are used in the capture of RNA (e.g., from microorganism) present in biological samples. In some embodiments, the presence of RNA is then detected using suitable methods (e.g., to determine the presence, absence, or amount of microorganism (e.g., viral target)) in a biological sample.

Experiments described herein demonstrated that CuTi particles capture RNA as well as other methods but do not capture DNA as well as the other methods. This means that the CuTi particles can selectively capture RNA. This is important, for example, in the measure method of RNA viruses. In some embodiments, it is not desirable to capture DNA because the presence of pro-viral DNA in the extraction could give an inaccurate determination of the amount of viral particles.

I. Capture

Embodiments of the present disclosure provide compositions and method for selectively capturing DNA or RNA. In some embodiments, compositions and methods of the present disclosure utilize particles and/or solid supports comprising or coated with metal oxides (See e.g., U.S. Pat. No. 6,936,414; herein incorporated by reference in its entirety). The present disclosure is not limited to particular metal oxides. In some embodiments, the metal oxide is a copper titanium oxide. In some embodiments, the CuTi is present at a ratio of approximately 2:1 Cu to Ti (e.g., 3:1, 2:1, 1:1, 1:2, 1:3, etc.).

In some embodiments, the metal or metal oxide is AlTi, CaTi, CoTi, $Fe_2Ti$, $Fe_3Ti$, MgTi, MnTi, NiTi, SnTi, ZnTi, $Fe_2O_3$, $Fe_3O_4$, Mg, Mn, Sn, Ti, or Zn (e.g., anhydrated or hydrated forms).

In some embodiments, the particles have a diameter of 0.5 to 50 μm (e.g., 0.5 μm, 1.0 μm, 1.5 μm, 2.0 μm, 5.0 μm, 10.0 μm, 20.0 μm, 30.0 μm, 40.0 μm, 50.0 μm, etc.). In some embodiments, particles and/or solid surfaces are comprised of organic polymers such as polystyrene and derivatives thereof, polyacrylates and polymethacrylates, and derivatives thereof or polyurethanes, nylon, polyethylene, polypropylene, polybutylene, and copolymers of these materials. In some embodiments, particles are polysaccharides, in particular hydrogels such as agarose, cellulose, dextran, Sephadex, Sephacryl, chitosan, inorganic materials such as e.g. glass or further metal oxides and metalloid oxides (in particular oxides of formula MeO, wherein Me is selected from, e.g., Al, Ti, Zr, Si, B, in particular $Al_2O_3$, $TiO_2$, silica and boron oxide) or metal surfaces, e.g. gold.

In some embodiments, particles are magnetic (e.g., paramagnetic, ferrimagnetic, ferromagnetic or superparamagnetic).

In some embodiments, the particles and/or solid surface may have a planer, acicular, cuboidal, tubular, fibrous, columnar or amorphous shape, although other geometries are specifically contemplated.

In some embodiments, commercially available particles (e.g., obtained from ISK Magnetics, Valparaiso, Ind.; Qiagen, Venlo, The Netherlands; Promega Corporation, Madison, Wis.; Life Technologies, Carlsbad, Calif.; Ademtech, NY, NY, and Sperotech, Lake Forest, Ill.).

In some embodiments, RNA capture comprises the step of contacting a biological sample (e.g., blood, blood product, cells, tissues, urine, semen, saliva, etc.) with a metal oxide particle. In some embodiments, the sample is processed prior to capture (e.g., cell lysis, purification, etc.). In some embodiments, the sample is not processed.

In some embodiments, particles described herein have the advantage of not substantially binding DNA (e.g., genomic, viral, and/or bacterial DNA) or not substantially binding RNA. For example in some embodiments, the particles bind less than 20% (e.g., less than 19%, 18%, 17%, 16%, 15%, 14%, 13%, 12%, 11%, 10%, 9%, 8%, 7%, 6%, 5%, 4%, 3%, 2%, or 1%) of DNA or RNA in the sample.

After binding of DNA or RNA to the particle, particles are washed to remove unbound components of the sample (e.g., using a wash buffer). In some embodiments, commercially available buffers (e.g., available from Qiagen, Venlo, The Netherlands; Promega Corporation, Madison, Wis.; and Abbott, Abbott Park, Ill.) are utilized. In some embodiments, particles are then isolated from the sample (e.g., using a magnet, centrifugation, or other suitable technique such as those method described by the aforementioned commercial vendors).

In some embodiments, RNA and/or DNA is eluted from the particles or solid support (e.g., using an elution buffer). In some embodiments, the elution buffer comprises phosphate (e.g., inorganic phosphate or organophosphate) at a concentration of 1 to 10 mM (e.g. 1, 2, 3, 4, 5, 6, 7, 8, 9, or 10 mM). In some embodiments, the metal or metal oxide and/or phosphate concentration is chosen to preferentially bind and/or elute DNA or RNA (See e.g., Example 10 below).

In some embodiments, the present disclosure provides kits and systems for capturing and purifying DNA and/or RNA. In some embodiments, the kits and systems comprise the particles described herein, controls, buffers, instructions, solid supports, separation components, (e.g., magnets), and the like. In some embodiments, kits and systems further comprising reagents for downstream analysis of captured RNA (e.g., reagents for performing a detection assay described below).

In some embodiments, captured DNA or RNA is subjected to further analysis to determine the identity and/or quantity of the DNA or RNA (e.g., using one or more detection methods described below). In some embodiments, the RNA is RNA from a pathogenic virus (e.g., bymoviruses, comoviruses, nepoviruses, nodaviruses, picornaviruses, potyviruses, sobemoviruses, luteoviruses (beet western yellows virus and potato leafroll virus), the picorna like group (Picornavirata), carmoviruses, dianthoviruses, flaviviruses, pestiviruses, tombusviruses, single-stranded RNA bacteriophages, hepatitis C virus and a subset of luteoviruses (barley yellow dwarf virus)—the flavi like group (Flavivirata), alphaviruses, carlaviruses, furoviruses, hordeiviruses, potexviruses, rubiviruses, tobraviruses, tricornaviruses, tymoviruses, apple chlorotic leaf spot virus, beet yellows virus and hepatitis E virus—the alpha like group (Rubivirata), family Birnaviridae, family Chrysoviridae, family Cystoviridae, family Endornaviridae, family Hypoviridae, family Megabirnaviridae, family Partitiviridae, family Picobirnaviridae, family Reoviridae—includes Rotavirus, family Totiviridae, Botrytis porri RNA virus 1, Circulifer tenellus virus 1, Cucurbit yellows associated virus, Sclerotinia sclerotiorum debilitation-associated virus, Spissistilus festinus virus 1, order Nidovirales, family Arteriviridae, family Coronaviridae—includes Coronavirus, SARS, family Mesoniviridae, family Roniviridae, order Picornavirales, family Dicistroviridae, family Iflaviridae, family Marnaviridae, family Picornaviridae—includes Poliovirus, Rhinovirus (a common cold virus), Hepatitis A virus, family Secoviridae includes subfamily Comovirinae, genus Bacillarionavirus, genus Labyrnavirus, order Tymovirales, family Alphaflexiviridae, family Betaflexiviridae, family Gammaflexiviridae, family Tymoviridae, family Alphatetraviridae, family Alvernaviridae, family Astroviridae, family Barnaviridae, family Bromoviridae, family Caliciviridae—includes Norwalk virus, family Carmotetraviridae, family Closteroviridae, family Flaviviridae—includes Yellow fever virus, West Nile virus, Hepatitis C virus (HCV), Dengue fever virus, family Leviviridae, family Luteoviridae—includes Barley yellow dwarf virus, family Narnaviridae, family Nodaviridae, family Permutotetraviridae, family Potyviridae, family Togaviridae—includes Rubella virus, Ross River virus, Sindbis virus, Chikungunya virus, family Tombusviridae, family Virgaviridae, genus Benyvirus, genus Blunervirus, genus Cilevirus, genus Hepevirus—includes Hepatitis E virus, genus Higrevirus, genus Idaeovirus, genus Negevirus, genus Ourmiavirus, genus Polemovirus, genus Sobemovirus, genus Umbravirus, Acyrthosiphon pisum virus, Blueberry necrotic ring blotch virus, Botrytis virus F, Canine picodicistrovirus, Chronic bee paralysis associated satellite virus, Extra small virus, Heterocapsa circularisquama RNA virus, Kelp fly virus, Le Blanc virus, Plasmopara halstedii virus, Orsay virus, Rosellinia necatrix fusarivirus 1, Santeuil virus, Solenopsis invicta virus 2, Solenopsis invicta virus 3, order Mononegavirales, family Bornaviridae—Borna disease virus, family Filoviridae—includes Ebola virus, Marburg virus, family Paramyxoviridae—includes Measles virus, Mumps virus, Nipah virus, Hendra virus, RSV and NDV, family Rhabdoviridae—includes Rabies virus, family Nyamiviridae—includes Nyavirus, family Arenaviridae—includes Lassa virus, family Bunyaviridae—includes Hantavirus, Crimean-Congo hemorrhagic fever, family Ophioviridae, family Orthomyxoviridae—includes Influenza viruses, genus Deltavirus—includes Hepatitis D virus, genus Dichorhavirus, genus Emaravirus, genus Nyavirus—includes Nyamanini and Midway viruses, genus Tenuivirus, genus Varicosavirus, Taastrup virus, or Sclerotinia sclerotiorum negative-stranded RNA virus 1.

In some embodiments, particles find use in sensors that generate or modulate an electrical signal upon the binding of a nucleic acid.

II. Assays

In some embodiments, following capture, RNA is detected and/or quantitated. Exemplary assays are described herein.

In some embodiments, assays are nucleic acid detection assays (e.g., amplification, sequencing, hybridization, etc.). Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

In some embodiments, nucleic acid sequencing methods are utilized (e.g., for detection of amplified nucleic acids). In some embodiments, the technology provided herein finds use in a Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), semiconductor sequencing, massive parallel clonal, massive parallel single molecule SBS, massive parallel single molecule real-time, massive parallel single molecule real-time nanopore technology, etc. Morozova and Marra provide a review of some such technologies in *Genomics,* 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

A number of DNA sequencing techniques are suitable, including fluorescence-based sequencing methodologies (See, e.g., Birren et al., Genome Analysis: Analyzing DNA, 1, Cold Spring Harbor, N.Y.; herein incorporated by reference in its entirety). In some embodiments, the technology finds use in automated sequencing techniques understood in that art. In some embodiments, the present technology finds use in parallel sequencing of partitioned amplicons (PCT Publication No: WO2006084132 to Kevin McKernan et al., herein incorporated by reference in its entirety). In some embodiments, the technology finds use in DNA sequencing by parallel oligonucleotide extension (See, e.g., U.S. Pat. No. 5,750,341 to Macevicz et al., and U.S. Pat. No. 6,306, 597 to Macevicz et al., both of which are herein incorporated by reference in their entireties). Additional examples of sequencing techniques in which the technology finds use include the Church polony technology (Mitra et al., 2003, Analytical Biochemistry 320, 55-65; Shendure et al., 2005 Science 309, 1728-1732; U.S. Pat. Nos. 6,432,360, 6,485, 944, 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., *Clinical Chem.,* 55: 641-658, 2009; MacLean et al., *Nature Rev. Microbiol.,* 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), Life Technologies/Ion Torrent, the Solexa platform commercialized by Illumina, GnuBio, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In pyrosequencing (Voelkerding et al., *Clinical Chem.,* 55: 641-658, 2009; MacLean et al., *Nature Rev. Microbiol.,* 7: 287-296; U.S. Pat. Nos. 6,210,891; 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., *Clinical Chem.*, 55: 641-658, 2009; MacLean et al., *Nature Rev. Microbiol.*, 7: 287-296; U.S. Pat. Nos. 6,833,246; 7,115,400; 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 250 nucleotides, with overall output exceeding 1 billion nucleotide pairs per analytical run.

Sequencing nucleic acid molecules using SOLiD technology (Voelkerding et al., *Clinical Chem.*, 55: 641-658, 2009; MacLean et al., *Nature Rev. Microbiol.*, 7: 287-296; U.S. Pat. Nos. 5,912,148; 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, the technology finds use in nanopore sequencing (see, e.g., Astier et al., J. Am. Chem. Soc. 2006 Feb. 8; 128(5):1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, the technology finds use in HeliScope by Helicos BioSciences (Voelkerding et al., *Clinical Chem.*, 55: 641-658, 2009; MacLean et al., *Nature Rev. Microbiol.*, 7: 287-296; U.S. Pat. Nos. 7,169,560; 7,282,337; 7,482,120; 7,501,245; 6,818,395; 6,911,345; 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb to 100 Gb generated per run. The read-length is 100-300 base pairs. The accuracy for homopolymer repeats of 5 repeats in length is ~98%. The benefits of ion semiconductor sequencing are rapid sequencing speed and low upfront and operating costs.

The technology finds use in another nucleic acid sequencing approach developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., *Clinical Chem.*, 55: 641-58, 2009; U.S. Pat. No. 7,329,492; U.S. patent application Ser. No. 11/671,956; U.S. patent application Ser. No. 11/781,166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

In some embodiments, detection methods utilize hybridization assays. Illustrative non-limiting examples of nucleic acid hybridization techniques include, but are not limited to, microarrays including, but not limited to: DNA microarrays (e.g., cDNA microarrays and oligonucleotide microarrays). A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes or transcripts by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Attachment of fluorophores to nucleic acid probes is well known in the art and may be accomplished by any available means. Fluorophores can be covalently attached to a particular nucleotide, for example, and the labeled nucleotide incorporated into the probe using standard techniques such as nick translation, random priming, PCR labeling, and the like. Alternatively, the fluorophore can be covalently attached via a linker to the deoxycytidine nucleotides of the probe that have been transaminated. Methods for labeling probes are described in U.S. Pat. No. 5,491,224 and Molecular Cytogenetics: Protocols and Applications (2002), Y.-S. Fan, Ed., Chapter 2, "Labeling Fluorescence In Situ Hybridization Probes for Genomic Targets," L. Morrison et al., p. 21-40, Humana Press, both of which are herein incorporated by reference for their descriptions of labeling probes.

Exemplary fluorophores that can be used for labeling probes include TEXAS RED (Molecular Probes, Inc., Eugene, Oreg.), CASCADE blue aectylazide (Molecular Probes, Inc., Eugene, Oreg.), SPECTRUMORANGE™ (Abbott Molecular, Des Plaines, Ill.) and SPECTRUM-GOLD™ (Abbott Molecular).

Examples of fluorophores that can be used in the methods described herein are: 7-amino-4-methylcoumarin-3-acetic acid (AMCA); 5-(and -6)-carboxy-X-rhodamine, lissamine rhodamine B, 5-(and -6)-carboxyfluorescein; fluorescein-5-isothiocyanate (FITC); 7-diethylaminocoumarin-3-carboxylic acid, tetramethyl-rhodamine-5-(and -6)-isothiocyanate; 5-(and -6)-carboxytetramethylrhodamine; 7-hydroxy-coumarin-3-carboxylic acid; 6-[fluorescein 5-(and -6)-carboxamido]hexanoic acid; N-(4,4-difluoro-5,7-dimethyl-4-bora-3a, 4a diaza-3-indacenepropionic acid; eosin-5-isothiocyanate; erythrosine-5-isothiocyanate; 5-(and -6)-carboxyrhodamine 6G; and Cascades blue aectylazide (Molecular Probes, Inc., Eugene, Oreg.).

Probes can be viewed with a fluorescence microscope and an appropriate filter for each fluorophore, or by using dual or triple band-pass filter sets to observe multiple fluorophores. See, e.g., U.S. Pat. No. 5,776,688 to Bittner, et al., which is incorporated herein by reference. Any suitable microscopic imaging method can be used to visualize the hybridized probes, including automated digital imaging systems, such as those available from MetaSystems or Applied Imaging. Alternatively, techniques such as flow cytometry can be used to examine the hybridization pattern of the chromosomal probes.

Probes can also be labeled indirectly, e.g., with biotin or digoxygenin by means well known in the art. However, secondary detection molecules or further processing are then used to visualize the labeled probes. For example, a probe labeled with biotin can be detected by avidin conjugated to a detectable marker, e.g., a fluorophore. Additionally, avidin can be conjugated to an enzymatic marker such as alkaline phosphatase or horseradish peroxidase. Such enzymatic markers can be detected in standard colorimetric reactions using a substrate for the enzyme. Substrates for alkaline phosphatase include 5-bromo-4-chloro-3-indolylphosphate and nitro blue tetrazolium. Diaminobenzoate can be used as a substrate for horseradish peroxidase. Fluorescence detection of a hybridized biotin or other indirect labeled probe can be achieved by use of the commercially available tyramide amplification system.

Other agents or dyes can be used in lieu of fluorophores as label-containing moieties. Suitable labels that can be attached to probes include, but are not limited to, radioisotopes, fluorophores, chromophores, mass labels, electron dense particles, magnetic particles, spin labels, molecules that emit luminescence, electrochemically active molecules, enzymes, cofactors, and enzyme substrates. Luminescent agents include, for example, radioluminescent, chemiluminescent, bioluminescent, and phosphorescent label containing moieties. Alternatively, detection moieties that are visualized by indirect means can be used. For example, probes can be labeled with biotin or digoxygenin using routine methods known in the art, and then further processed for detection. Visualization of a biotin-containing probe can be achieved via subsequent binding of avidin conjugated to a detectable marker. The detectable marker may be a fluorophore, in which case visualization and discrimination of probes may be achieved as described above for ISH.

In some embodiments, probes are designed to have labels placed at a common interval throughout the nucleic acid (e.g., one label group every 3, 4, 5, 6, 7, 8, 9, 10, 11, or 12).

In some embodiments, a probe library comprises probes with different detectable labels (e.g., different colors of fluorescent signal).

Probes hybridized to target regions may alternatively be visualized by enzymatic reactions of label moieties with suitable substrates for the production of insoluble color products. A biotin-containing probe within a set may be detected via subsequent incubation with avidin conjugated to alkaline phosphatase (AP) or horseradish peroxidase (HRP) and a suitable substrate. 5-bromo-4-chloro-3-indolylphosphate and nitro blue tetrazolium (NBT) serve as substrates for alkaline phosphatase, while diaminobenzidine serves as a substrate for HRP.

In embodiments where fluorophore-labeled probes or probe compositions are used, the detection method can involve fluorescence microscopy, flow cytometry, or other means for determining probe hybridization. Any suitable microscopic imaging method may be used in conjunction with the methods of the present invention for observing multiple fluorophores. In the case where fluorescence microscopy is employed, hybridized samples may be viewed under light suitable for excitation of each fluorophore and with the use of an appropriate filter or filters. Automated digital imaging systems such as the MetaSystems, BioView or Applied Imaging systems may alternatively be used.

In some embodiments, the metal oxides described herein find use in biosensors. For example, in some embodiments, the metal oxides are used to coat electrical sensors that detect nucleic acids. In some embodiments, the metal oxide are used to capture nucleic acids (e.g., as described above). Captured nucleic acids are then detected using a target specific probe. In some embodiments, a target specific capture sequence is attached to the metal oxide and used to capture a specific nucleic acid target. In either case the binding of the nucleic acids to the metal oxide generates a detectible signal.

EXPERIMENTAL

Example 1

This example describes synthesis of CuTi coated particles. Different amounts of copper and/or titanium were compared. Experiments were also conducted to determine if phosphate is needed for the metal precipitation on the particles. NaOH is added first. The neutralization itself should precipitate the metals. The metal oxides are insoluble as well as the metal phosphates. The phosphate may not be precipitating any metals at this point since they are already precipitated.

Reagents

| Common Name | Vendor |
| --- | --- |
| Copper(II) chloride | Sigma-Aldrich |
| HCl 12M | Sigma-Aldrich |
| Iron Oxide-black | Rockwood |
| Potassium phosphate dibasic | Sigma-Aldrich |
| Sodium Hydroxide 50% | Sigma-Aldrich |
| Sodium Hydroxide 5N | Fisher |
| Sodium Phosphate dibasic | Sigma-Aldrich |
| Titanium(III) chloride solution | Sigma-Aldrich |

Twenty ml of 1 M $CuCl_2$ and 1 liter of 10 mM NaOH were prepared.

Particles were made using reagents below.

| | Tube | | | |
| --- | --- | --- | --- | --- |
| | 1 | 2 | 3 | 4 |
| ml Ti | 0.90 | 0.90 | 0.90 | 0.00 |
| ml Cu | 1.4 | 1.4 | 1.4 | 1.4 |
| ml phosphate | 3.6 | 1.8 | 0 | 0 |
| ml NaOH | 1.2 | 1.2 | 1.2 | 1.2 |
| ml 12M HCl | 0 | 0 | 0 | 0.05 |
| mM Ti | 9.45 | 9.45 | 9.45 | 0 |
| mM Cu | 14 | 14 | 14 | 14 |
| mM phosphate | 18 | 9 | 0 | 0 |
| mM NaOH | 229.2 | 229.2 | 229.2 | 229.2 |
| mM HCl | 0 | 0 | 0 | 6 |

Four aliquots of 10 g particles (Rockwood BK5000AP) were dispensed each into a 125 ml PETG bottle. 100 ml water was added to each bottle and bottles were placed on rotator to mix. Cu and Ti solutions were added to each bottle, shaken vigorously and put on rotator. All the particle suspensions were filtered through a 100 micron nylon filter. (Spectramesh #146488 (Spectrum Labs)). Fifty ml water was added to bottle after pouring over filter, shaken, and poured over filter to combine. NaOH was added to bottles. Phosphate was added to bottles #1 and #2, particles were washed, and captured particles magnetically.

Particles were washed 5 times with 100 ml water and resuspended up to total volume of 100 ml with 10 mM NaOH. Particles were diluted to 1% with 10 mM NaOH.

Test Particles for RNA Extraction.

The below table shows particles that were tested.

| mM Ti | mM Cu | NaOH | PO4 | total CuTi | cu/ti | Cu mixed | filtered |
| --- | --- | --- | --- | --- | --- | --- | --- |
| 6.615 | 10.5 | 169.75 | 12.6 | 17.1 | 1.59 | yes | yes |
| 12.6 | 18 | 291 | 24 | 30.6 | 1.43 | yes | yes |
| 9.45 | 14 | 232.8 | 18 | 23.5 | 1.48 | yes | yes |
| 9.45 | 14 | 232.8 | 9 | 23.5 | 1.48 | yes | yes |
| 9.45 | 14 | 232.8 | 0 | 23.5 | 1.48 | yes | yes |
| 0 | 14 | 232.8 | 0 | 14.0 | * | yes | yes |

CSC extraction was performed. Elution buffer was diluted to 5 mM phosphate, 10 ml elution buffer and 30 ml water. IC was added to lysis buffer—800 µl IC added to 70 ml LB. Particles were washed using LB without IC. Reagents were prepared by diluting elution buffer to 5 mM phosphate, 10 ml elution buffer and 30 ml water. Samples were prepared (HCV and Negative control) to a final dilution of 30 IU/ml.

Particle set up is shown below—each CSC run has multiple particle types (42 total samples).
Set Up Extraction Cartridges. Six Sets of 7

| Loading | Lysis Buffer + IC | MMP as listed below | Sample | LB as Wash1 | Wash2 | Elution 5 mM phosphate | temp |
|---|---|---|---|---|---|---|---|
| Well 1-lysis | 1.5 ml | 100 µl | 0.5 ml | | | | 50 C. |
| Well 2 | | | | | | | |
| Well 3 | | | | | | | |
| Well 4-Wash1 | | | | 0.7 ml | | | |
| Well 5-Wash2A | | | | | 0.8 ml | | |
| Well 6-Wash2B | | | | | 0.8 ml | | |
| Elution-5 mM phosphate | | | | | | 44 µl | 73 C. |

After amplification, the data was analyzed using Multi-Analyze. Results are shown in FIGS. 1A-D. Further statistical analysis was performed using JMP. Results are shown in FIGS. 2-3. Statistical analysis (oneway analysis of FAM-MR by mmp, oneway Analysis of FAM-Ct by mmp, oneway analysis of VIC-Ct by mmp, oneway analysis of VIC-MR by mmp) are shown in FIGS. 2A-D.

Figure 2A:
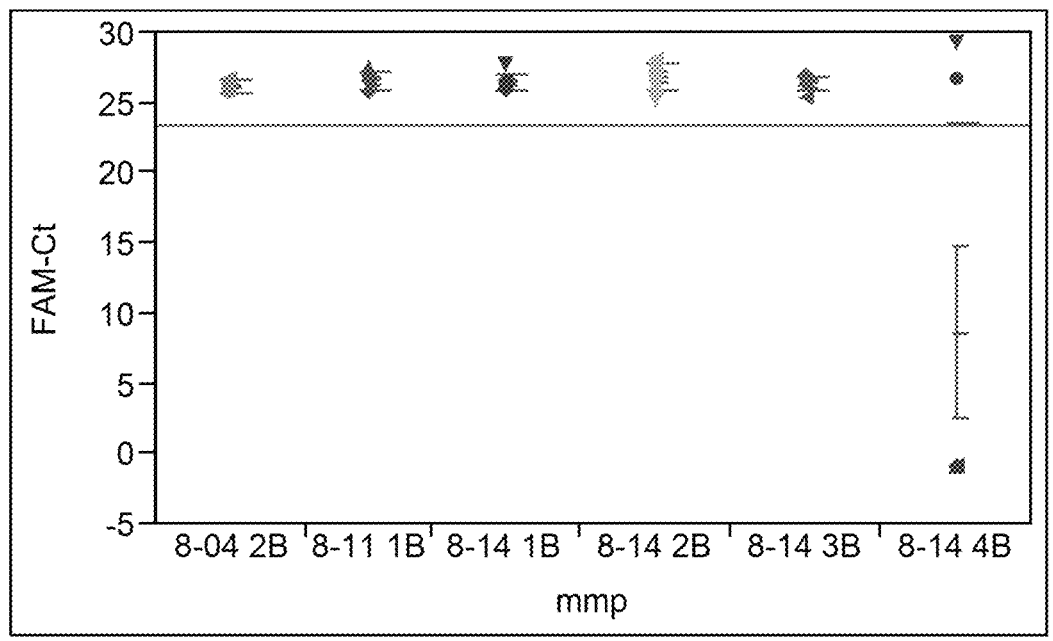
FIG. 2A-H shows signal from RNA binding by CuTi particles.
Figure 2B:
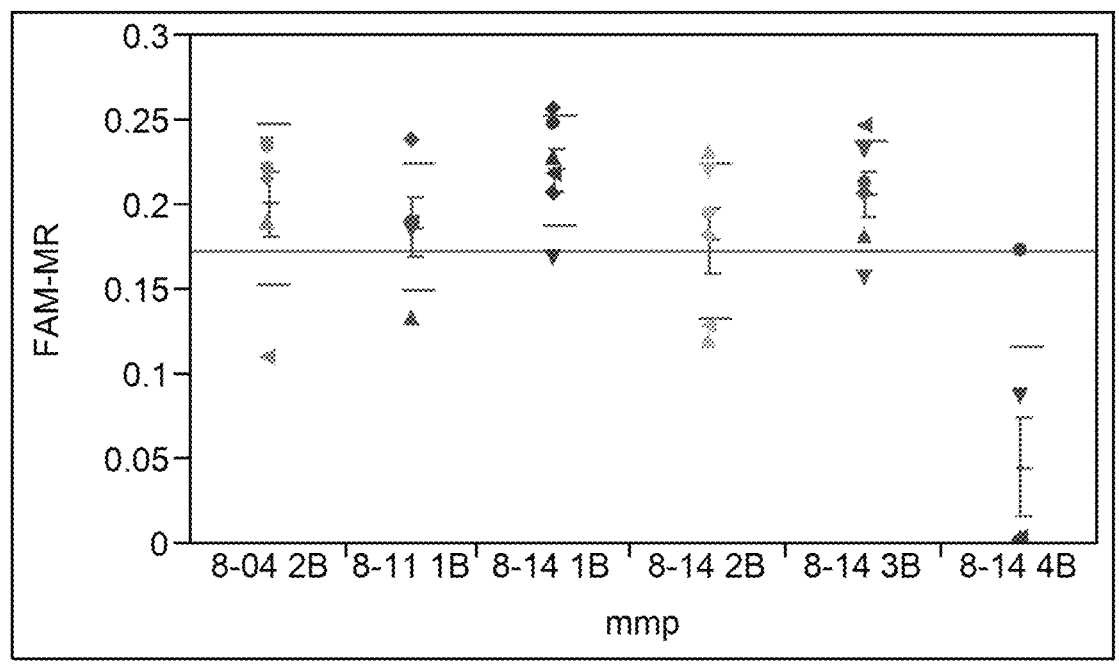
Figure 2C:
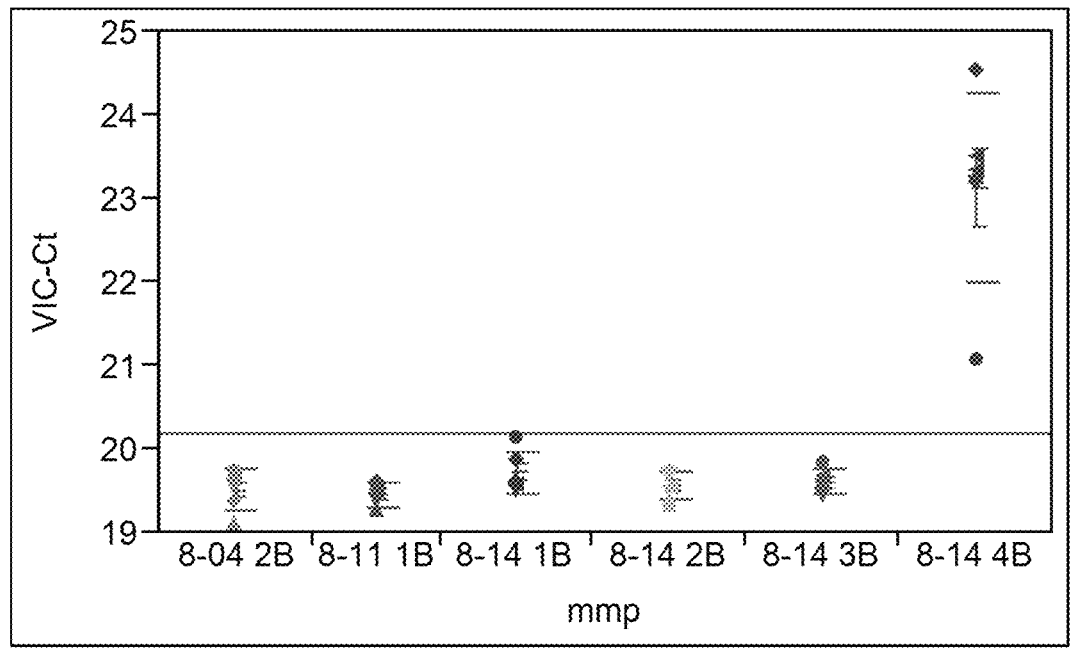
Figure 2D:
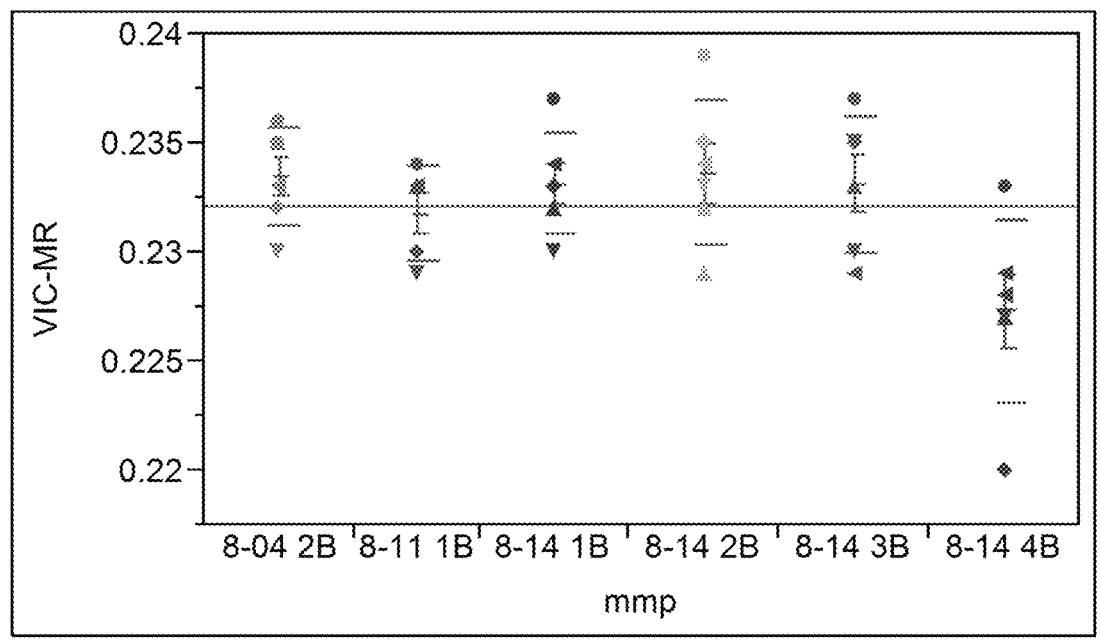
Figure 2E:
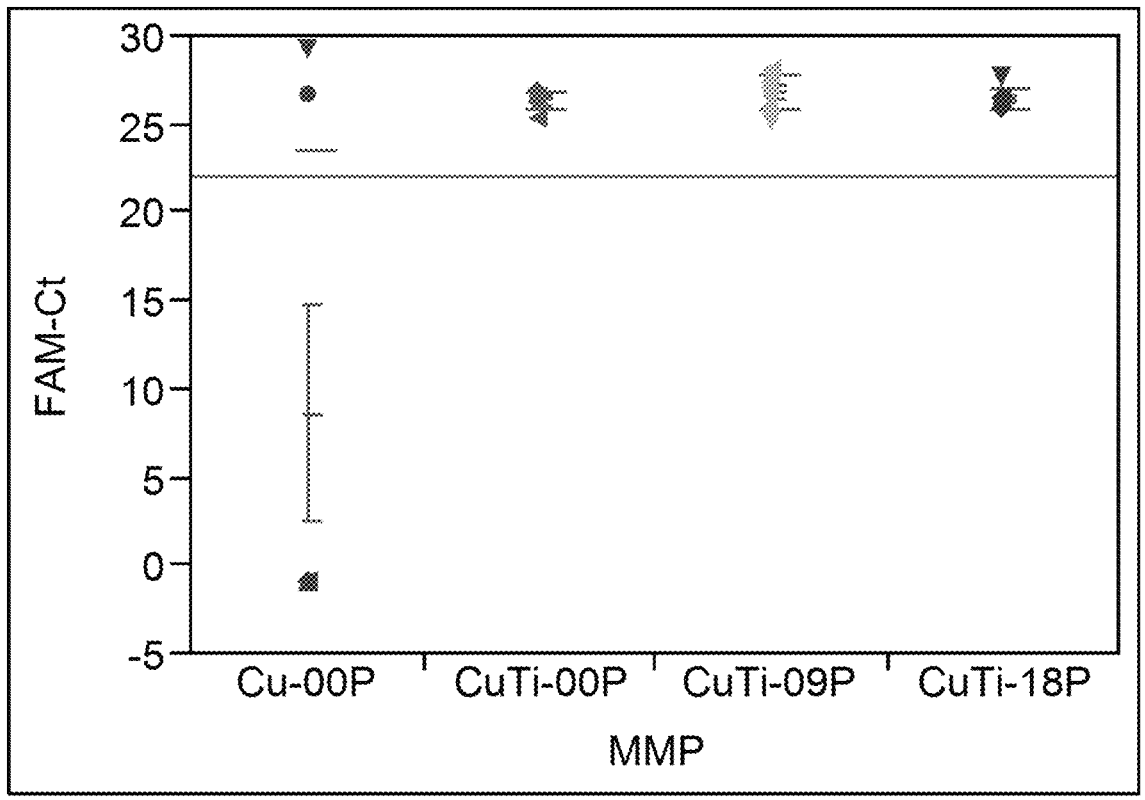
Figure 2F:
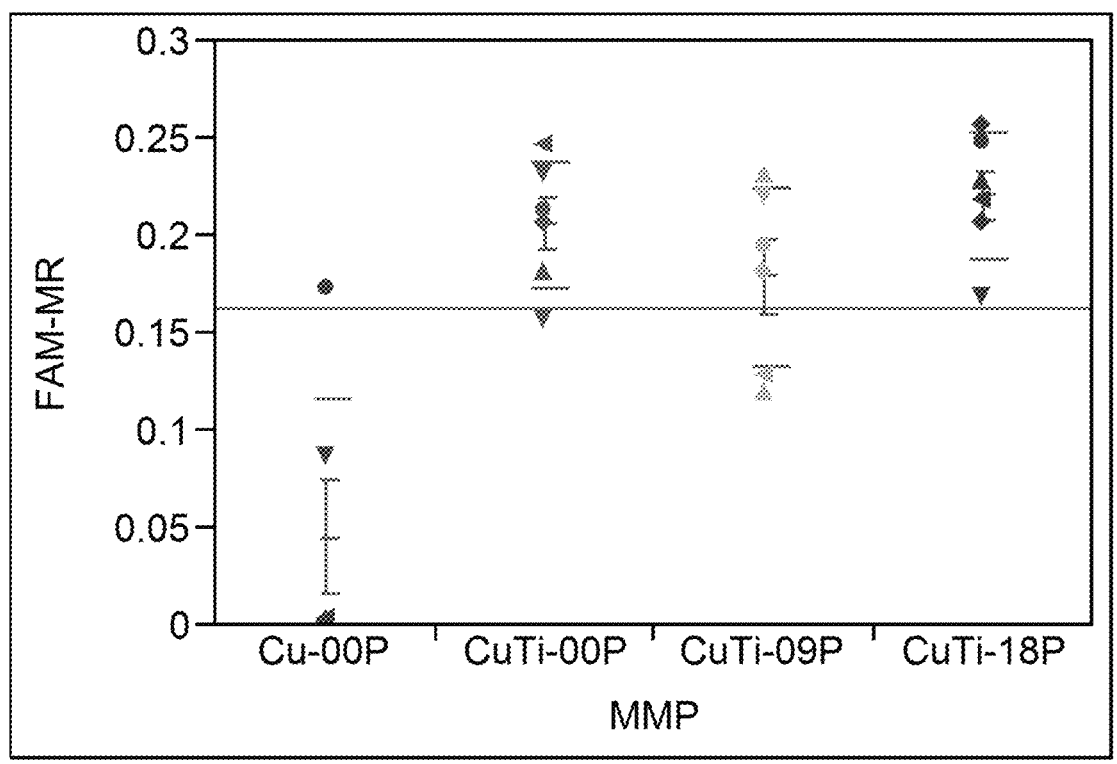
Figure 2G:
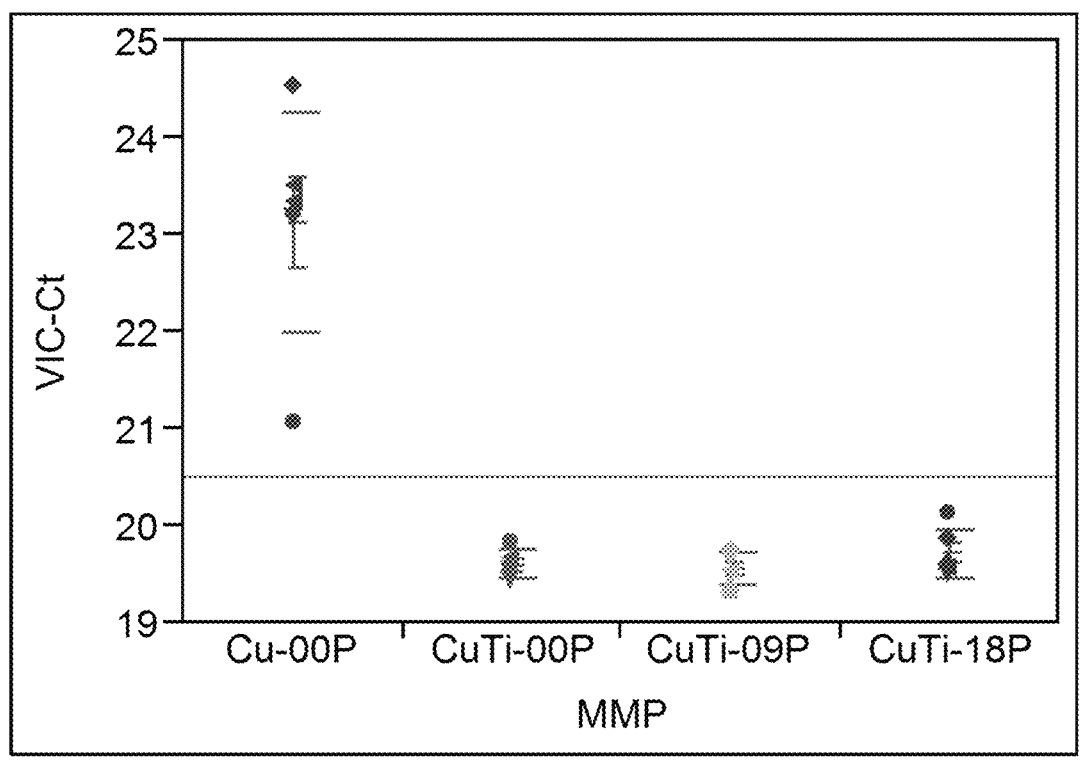
Figure 2H:
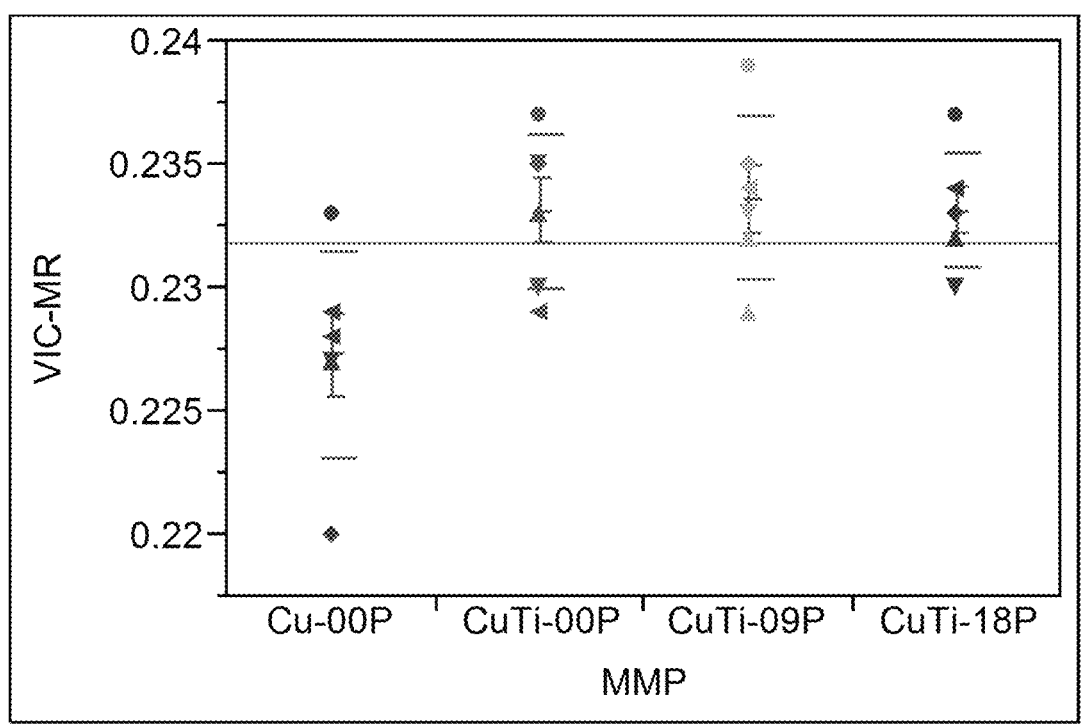

Further data on additional particles (oneway analysis of FAM-Ct by MMP, oneway analysis of FAM-MR by MMP, and oneway analysis of VIC-MR by MMP) is shown in FIGS. 2E-F.

Results indicated that the particles made without titanium and only copper oxide did not perform as well as the other types. They did not pick up HCV well and the internal control signal is off by ~3 CT (10 fold difference).

Figure 3A:
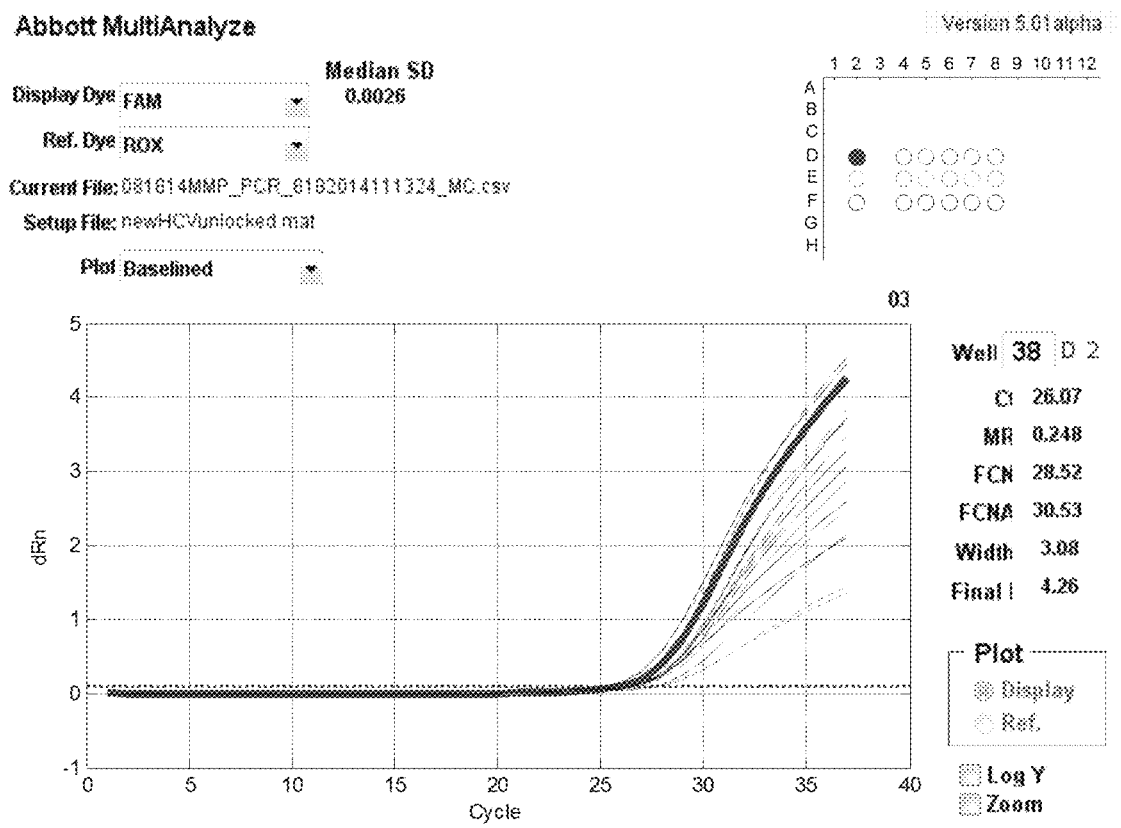
FIG. 3A-D shows RNA binding by Cu and CuTi particles.
Figure 3B:
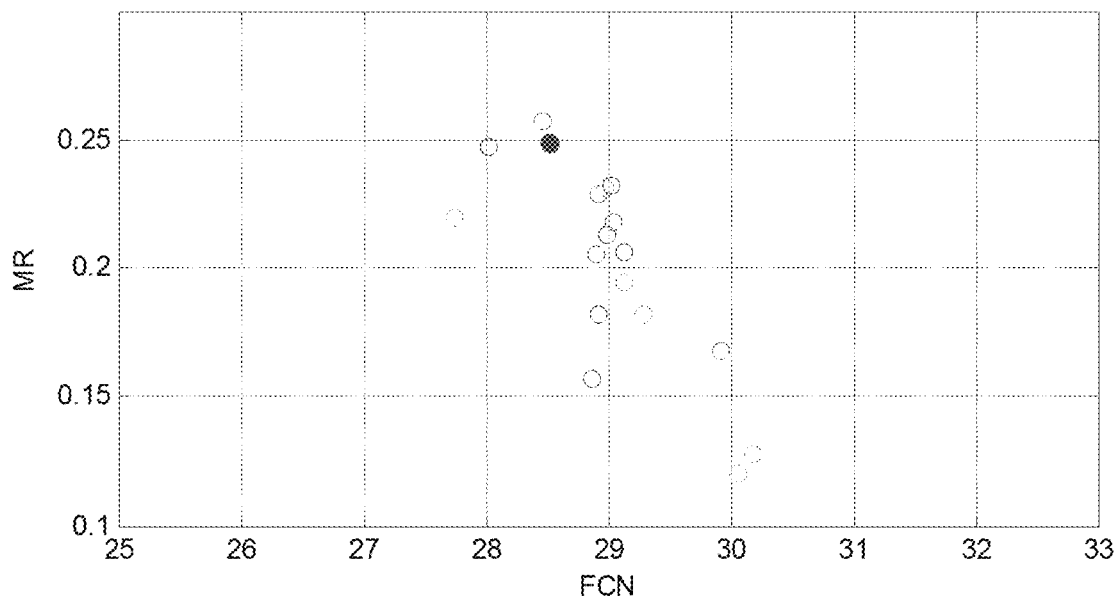
Figure 3C:
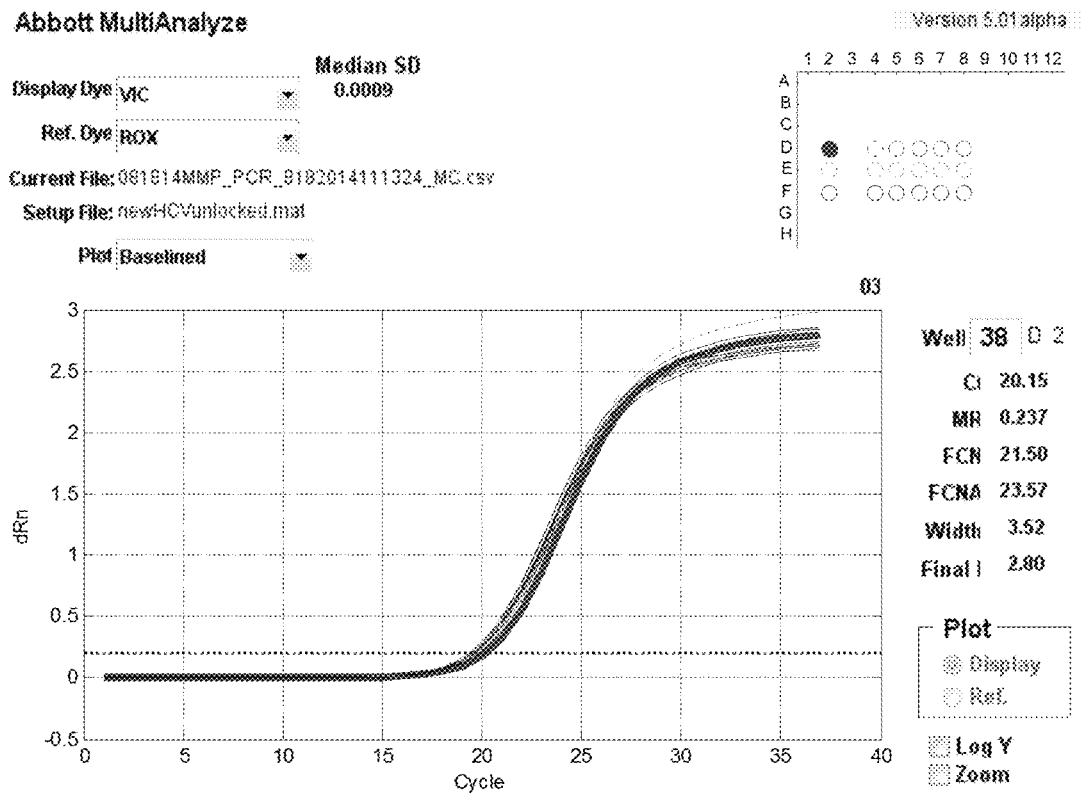
Figure 3D:
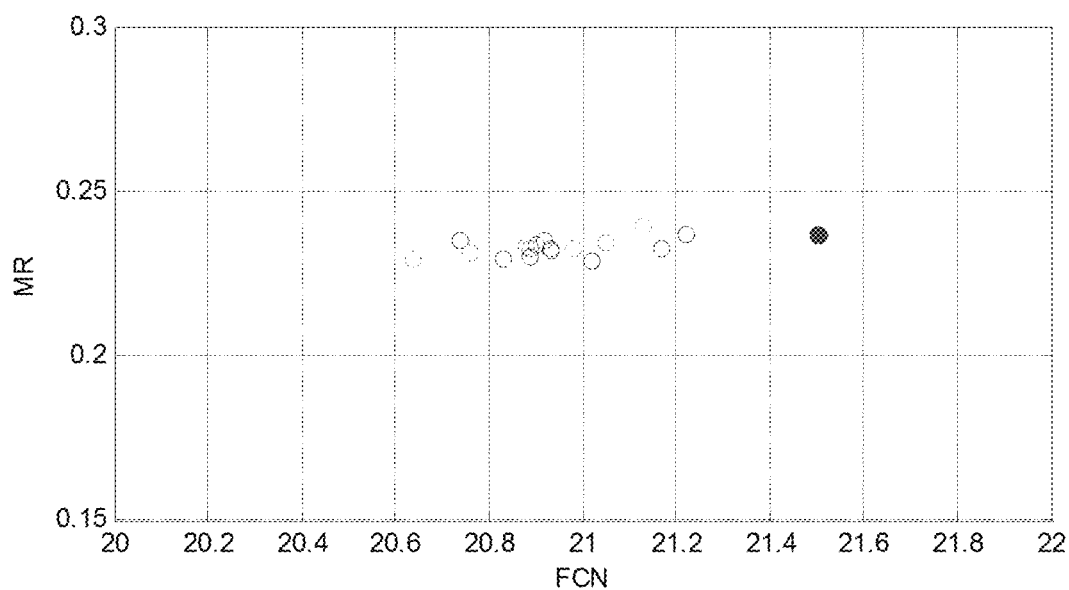
Figure 4A:
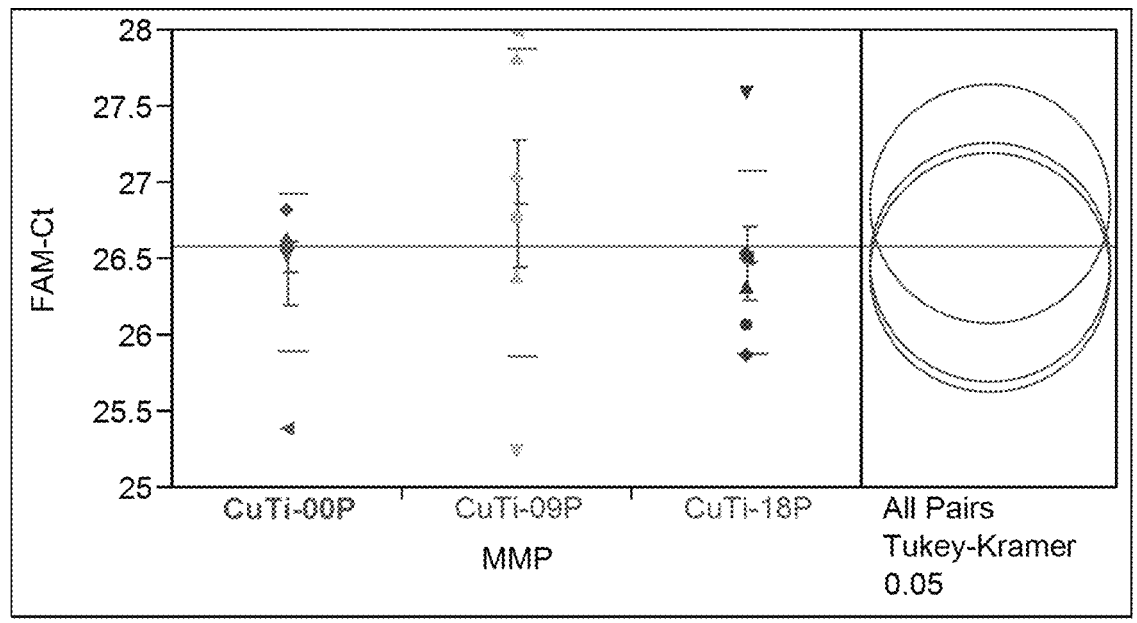
FIG. 4A-D shows signal from RNA binding by CuTi particles.
Figure 4B:
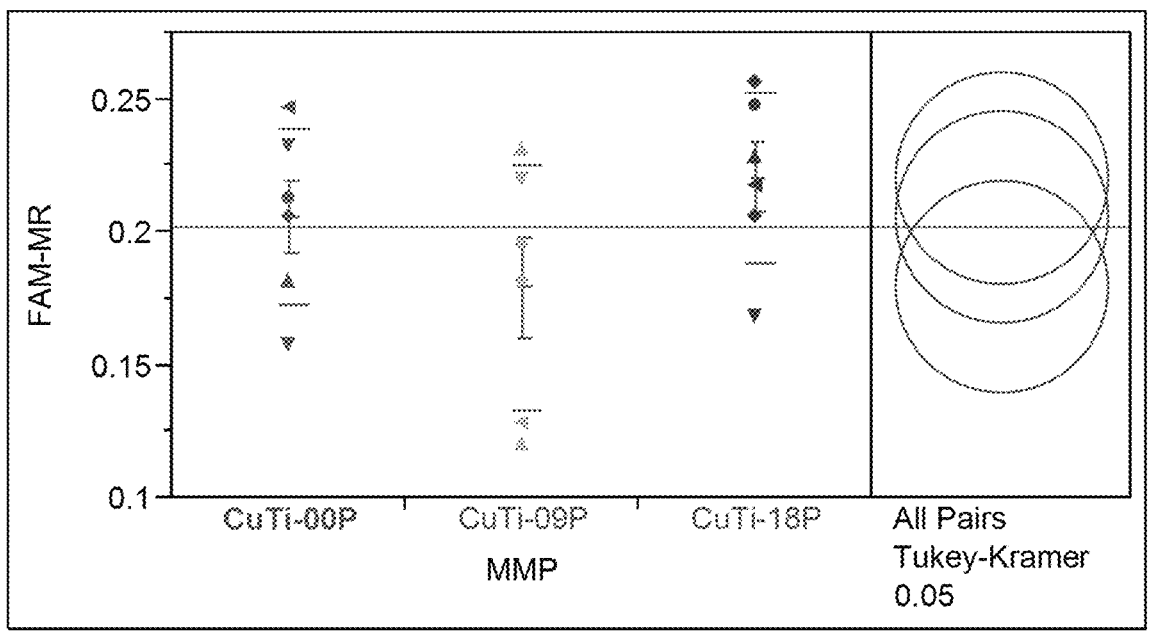
Figure 4C:
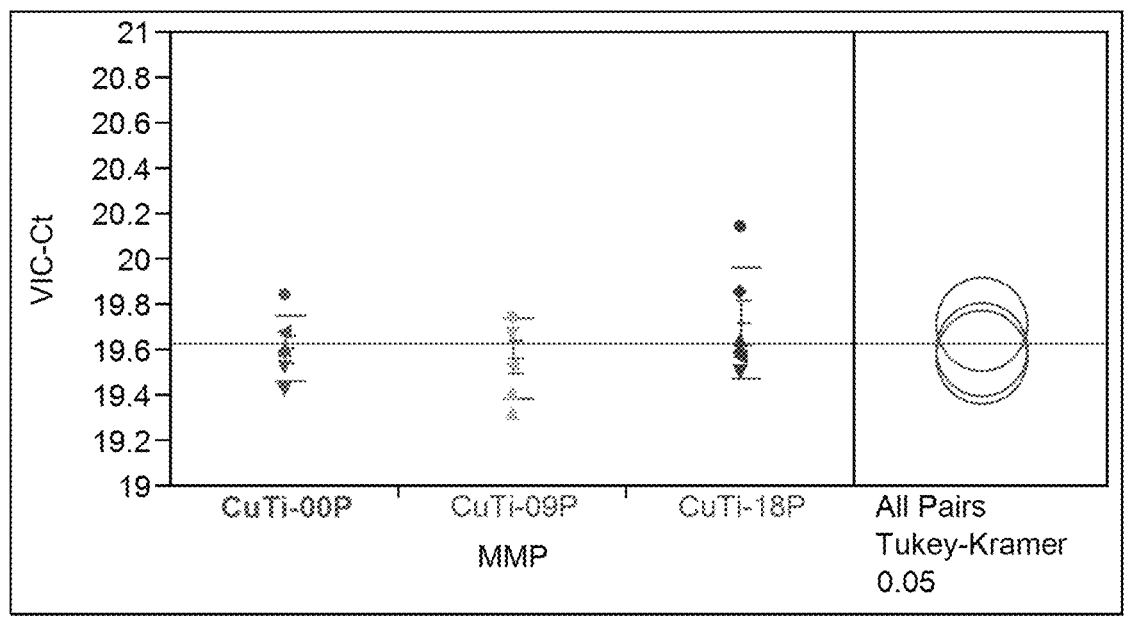
Figure 4D:
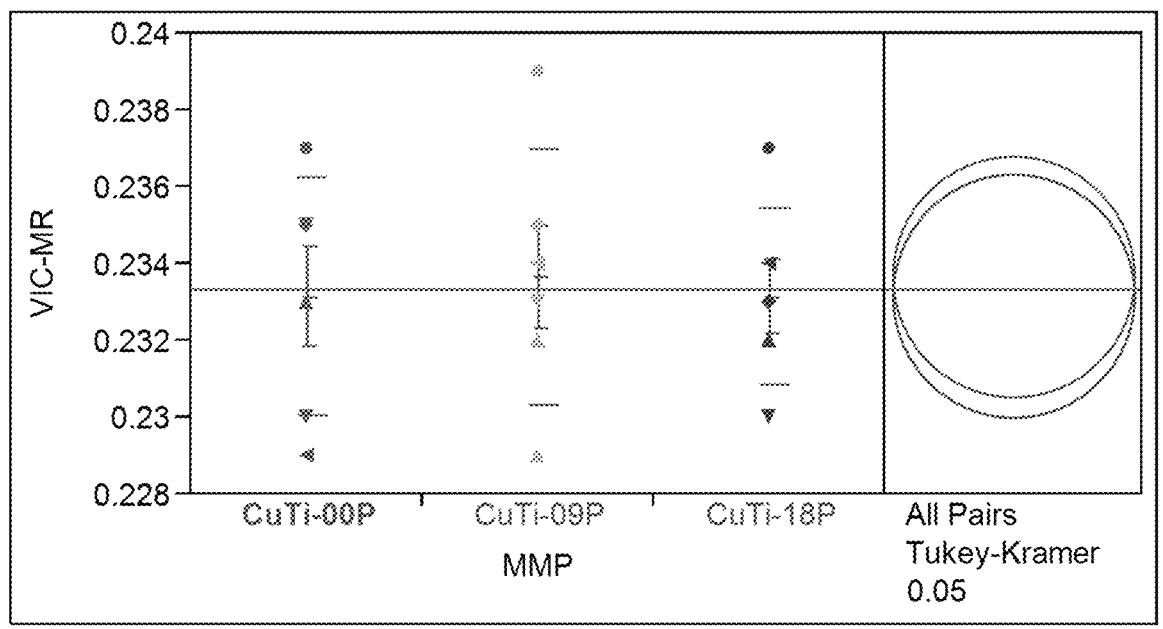

A comparison of only the CuTi particles is shown in FIGS. 3A and B. VIC MR is shown in FIG. 3C-D.

Further analysis (oneway analysis of FAM-Ct by MMP, oneway analysis of FAM-MR by MMP, oneway analysis of VIC-Ct by MMP, and oneway analysis of VIC-MR by MMP) is shown in FIGS. 4A-D.

Results show that the particles made without phosphate are not different in their performance than the ones made with phosphate. Phosphate is not needed in the production of these particles.

Example 2

This example describes an analysis of the ratio of Ti and Cu in metal oxide coatings of particles.

Reagents

| Common Name | Vendor |
|---|---|
| Copper(II) chloride | Sigma-Aldrich |
| HCl 12M | Sigma-Aldrich |
| Iron Oxide-black | Rockwood |
| Potassium phosphate dibasic | Sigma-Aldrich |
| Sodium Hydroxide 50% | Sigma-Aldrich |
| Sodium Hydroxide 5N | Fisher |
| Sodium Phosphate dibasic | Sigma-Aldrich |

-continued

| Common Name | Vendor |
|---|---|
| Titanium(III) chloride solution | Sigma-Aldrich |

$CuCl_2$ prepared with HCl similar to the $TiCl_3$. One liter of 10 mM NaOH, 1 liter of water, and 2 ml of 5N NaOH were prepared. The total concentration of Cu+Ti=24 mM. Ti was varied from 24 mM to 0 mM and Cu was varied from 0 to 24 mM respectively.

The below tables shows the concentrations of Cu and Ti in the different particles generated.

| Bottle | 1 | 2 | 3 | 4 | 5 | 6 | 7 |
|---|---|---|---|---|---|---|---|
| ml Ti | 2.29 | 1.90 | 1.52 | 1.14 | 0.76 | 0.38 | 0.00 |
| ml Cu | 0 | 0.4 | 0.8 | 1.2 | 1.6 | 2 | 2.4 |
| ml NaOH | 3 | 3 | 3 | 3 | 3 | 3 | 3 |
| mM Ti | 24 | 20 | 16 | 12 | 8 | 4 | 0 |
| mM Cu | 0 | 4 | 8 | 12 | 16 | 20 | 24 |
| mM NaOH | 582 | 582 | 582 | 582 | 582 | 582 | 582 |

Seven aliquots of 10 g particles (Rockwood BK5000AP) were dispensed into an a 125 ml PETG bottle and 100 ml water was added to each bottle. Cu and Ti solutions were added to each bottle, shaken vigorously and put on rotator. No pre-mixing before adding metals was performed. All the particle suspensions were filtered through a 100 micron nylon filter (Spectramesh #146488 (Spectrum Labs)). Fifty ml water was added to bottle after pouring over filter, shaken, and poured over filter to combine. NaOH was added to bottles. The particles were washed with 10 mM NaOH prior to resuspending to 10% in 10 mM NaOH. This makes the final concentration closer to 10 mM NaOH for storage. Particles were captured magnetically, fluid was decanted, and ~100 ml water added (this step was repeated 5-8 times).

Particles were re-suspended up to total volume of 100 ml with 10 mM NaOH and then diluted to 1% with 10 mM NaOH.

Test Particles for RNA Extraction.

Extraction testing was performed using elution with 0, 2.5 and 5 mM phosphate. CSC extraction was performed using elution buffer diluted to 5 mM phosphate, 5 ml elution buffer and 15 ml water; elution buffer diluted to 2.5 mM phosphate, 2.5 ml elution buffer and 17.5 ml water, and elution buffer 0 mM phosphate-water. IC was added to lysis buffer (800 µl IC added to 70 ml LB). Wash 1 was conducted using LB without IC.

Samples were prepared using HCV at a final concentration of 45 IU/ml and a negative control.

Each CSC run has multiple particle types as shown in the Table below.

| Loading | Lysis Buffer + IC | MMP as listed below | Sample | LB as Wash1 | Wash2 | Elution 5 mM phosphate | temp |
|---|---|---|---|---|---|---|---|
| Well 1-lysis | 1.5 ml | 100 µl | 0.5 ml | | | | 50 C. |
| Well 2 | | | | | | | |
| Well 3 | | | | | | | |
| Well 4-Wash1 | | | | 0.7 ml | | | |
| Well 5-Wash2A | | | | | 0.8 ml | | |
| Well 6-Wash2B | | | | | 0.8 ml | | |
| Elution-increased to 45 | | | | | | 45 µl | 73 C. |

After extraction, HCV purification assays were performed using 30 µl sample 30 µl master mix to reflect desired sample input volume.

Figure 5A:
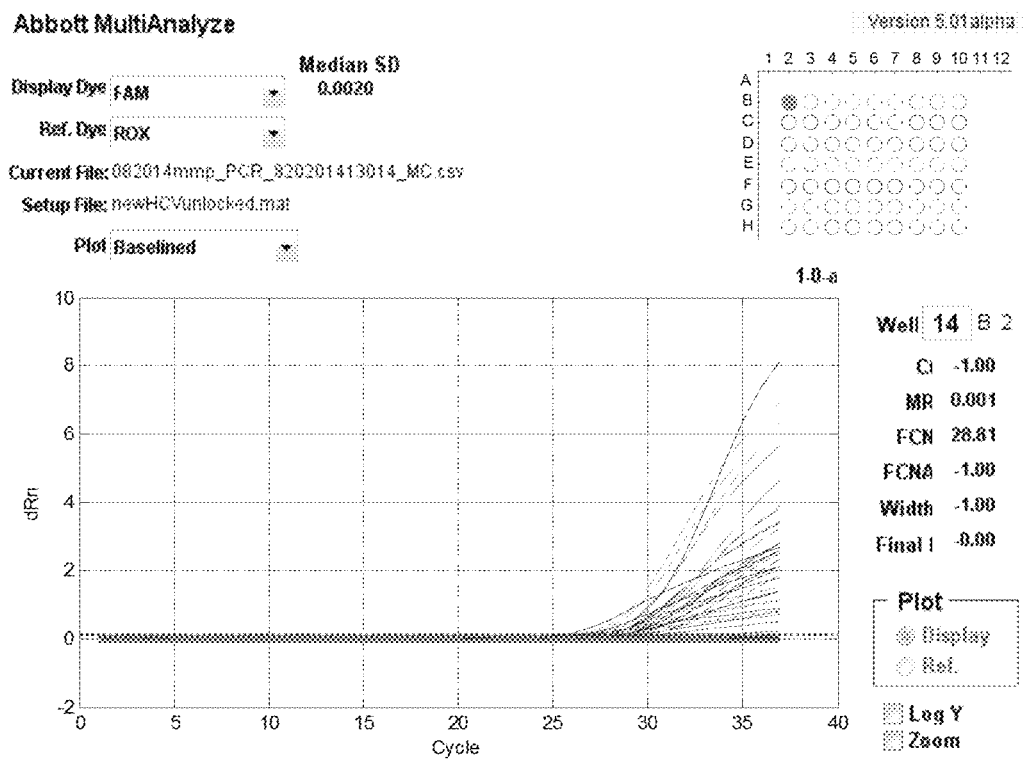
FIG. 5A-B shows the binding of RNA to CuTi coated particles.
Figure 5B:
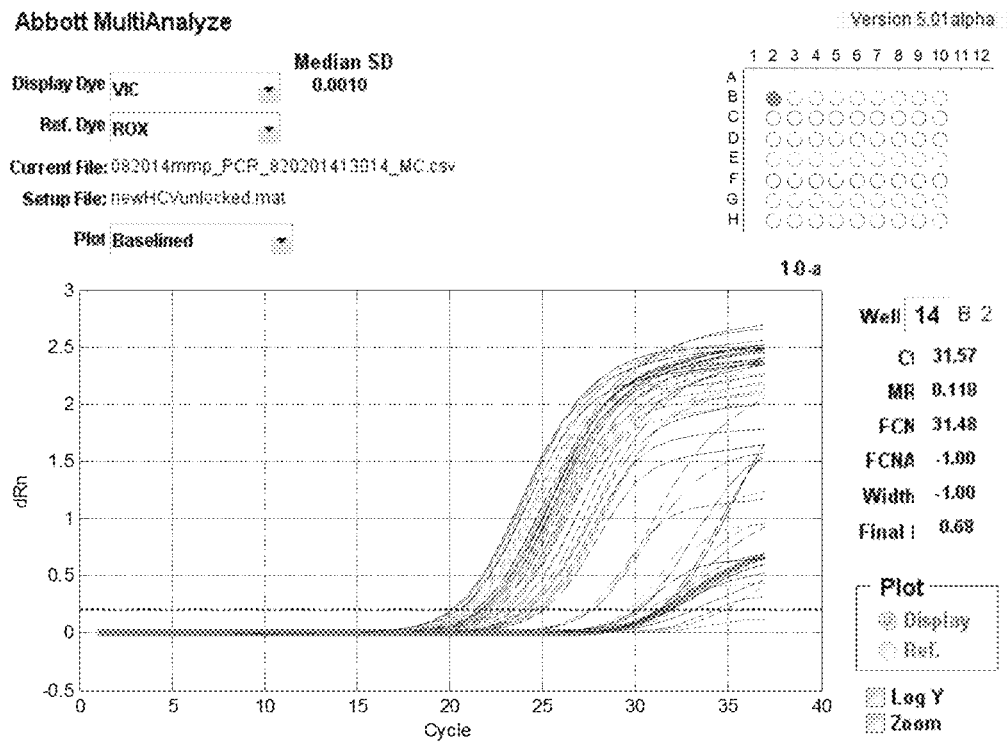
Figure 6A:
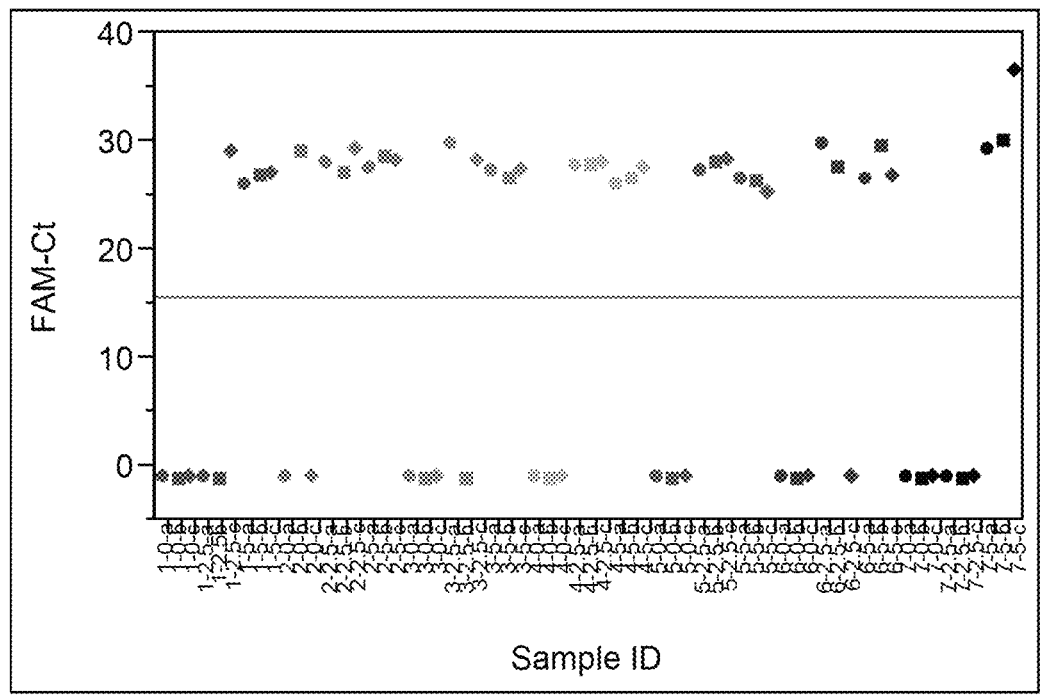
FIG. 6A-D shows the results of one way analysis of binding of RNA to CuTi coated particles with buffers of different phosphate concentrations.
Figure 6B:
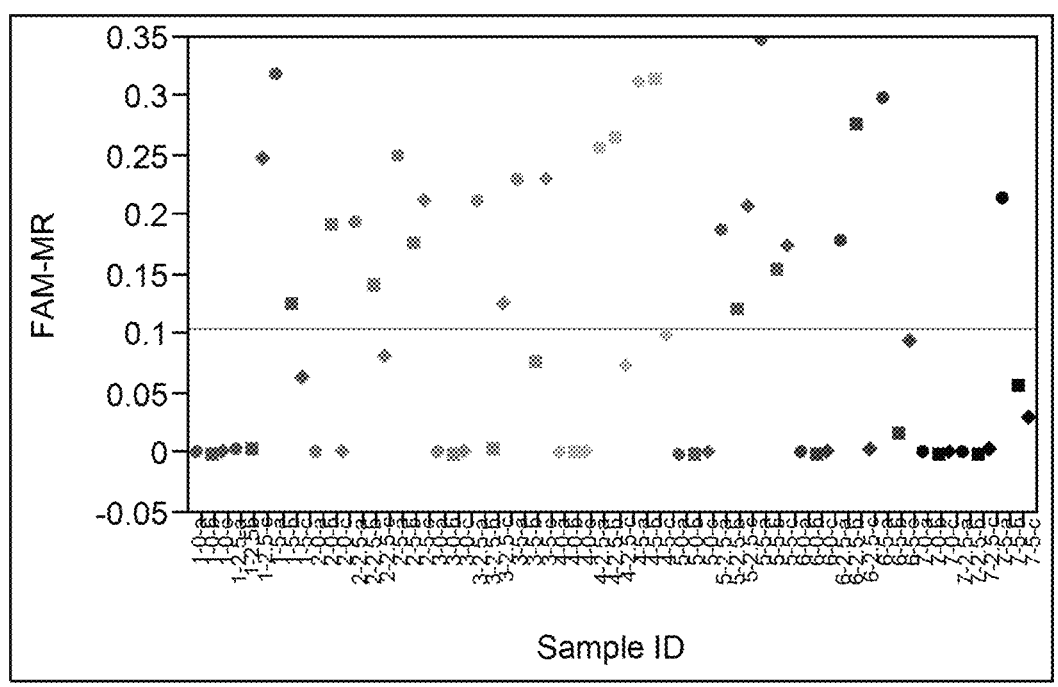
Figure 6C:
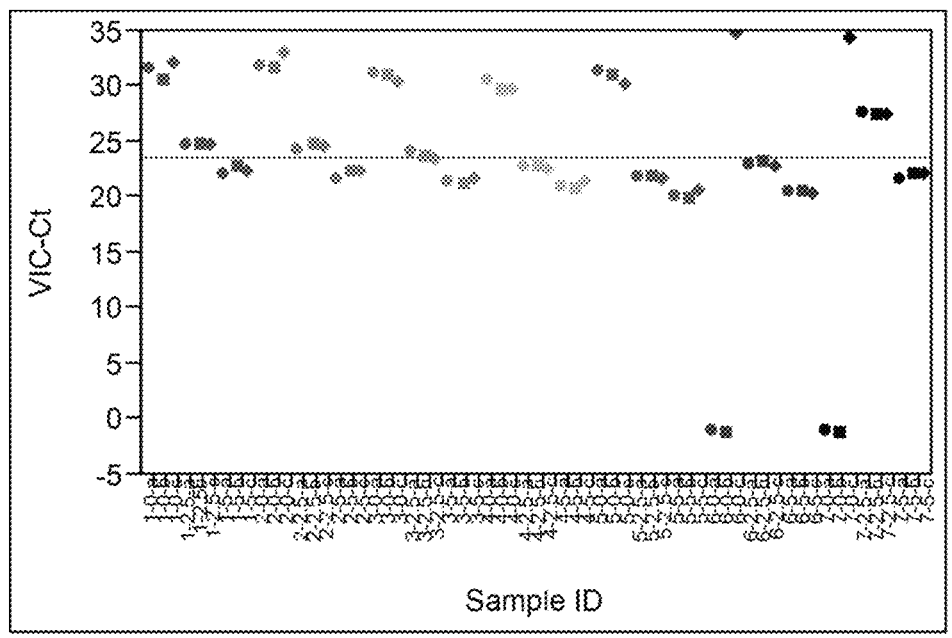
Figure 6D:
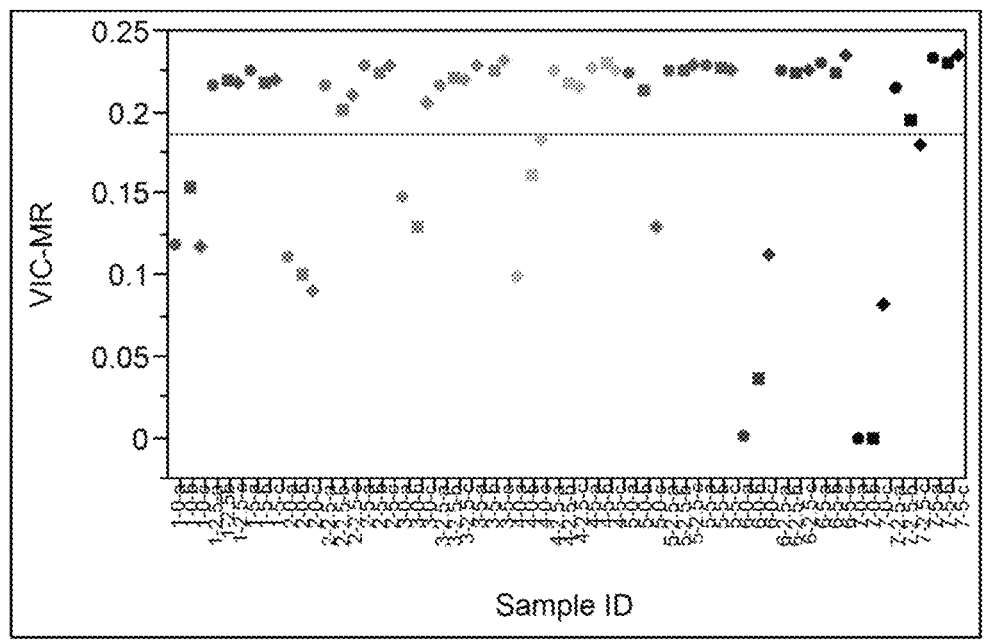

After amplification, the data was analyzed using Multi-Analyze. Results are shown in FIGS. 5A-B. Further statistical analysis was performed using JMP. Results of oneway Analysis of FAM-Ct by Sample ID (FIG. 6A), FAM-MR By Sample ID (FIG. 6B), VIC-Ct By Sample ID (FIG. 6C), and VIC-MR By Sample ID (FIG. 6D) are shown.

The 0 mM phosphate had poor recovery for all the particles. Results show that the phosphate is needed to elute the RNA. In conclusion, these data demonstrate that phosphate is needed for optimum elution of RNA from CuTi particles.

Titanium Level and Phosphate Elution Concentration

Figure 7A:
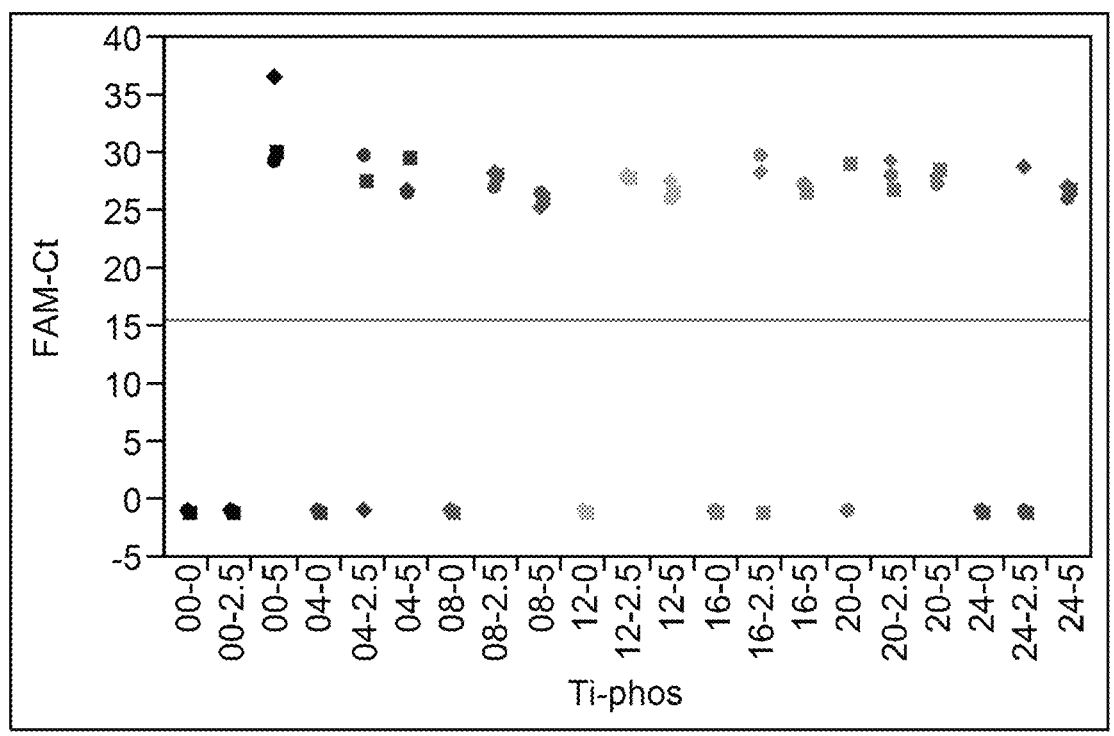
FIG. 7A-D shows the results of one way analysis of binding of RNA to CuTi coated particles with buffers of different phosphate concentrations.
Figure 7B:
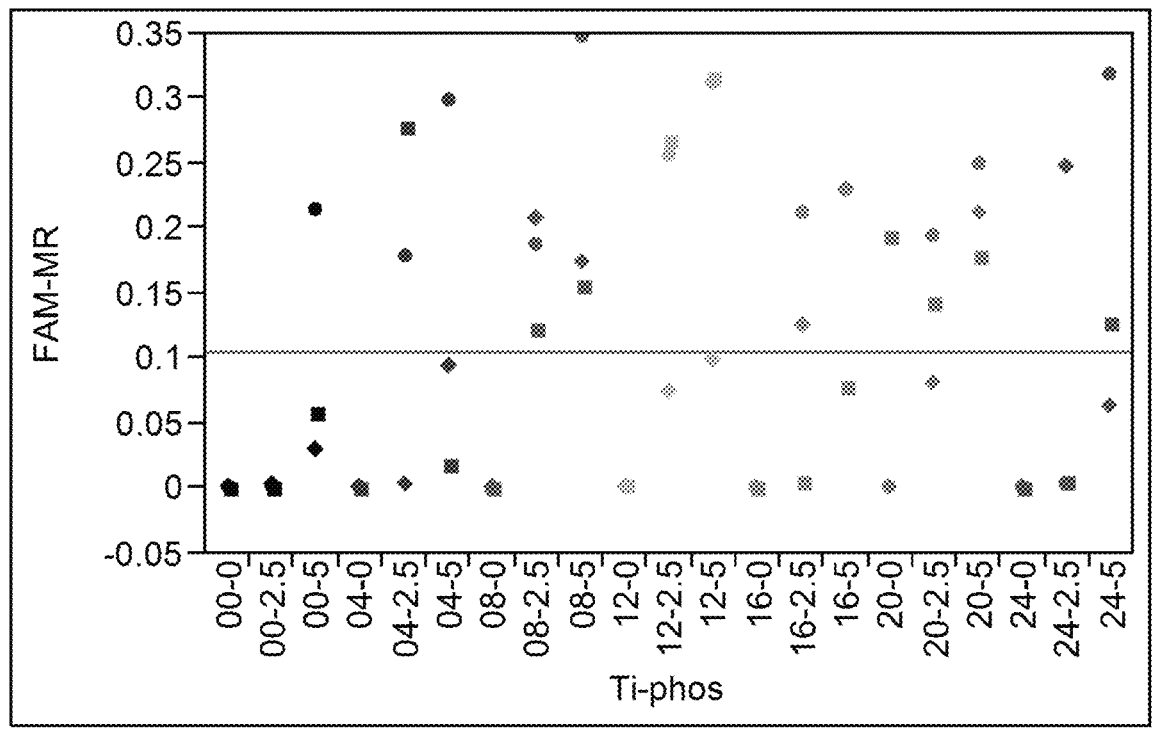
Figure 7C:
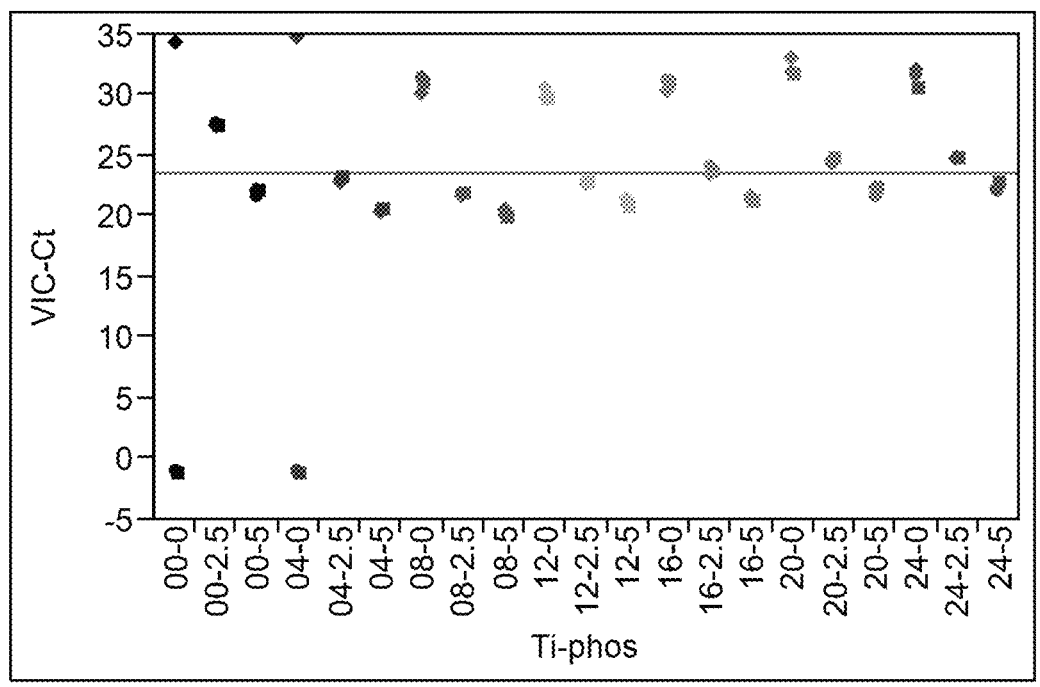
Figure 7D:
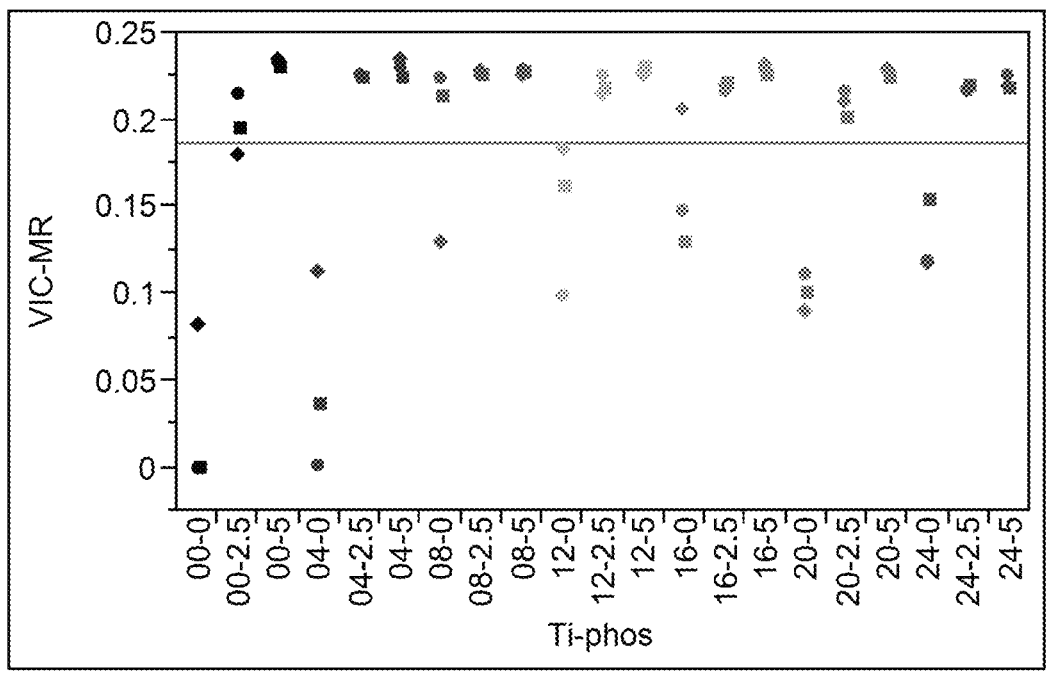

No target signal with 0 mM phosphate. Results of oneway Analysis of FAM-Ct By Ti-phos (FIG. 7A), FAM-MR By Ti-phos (FIG. 7B), VIC-Ct By Ti-phos (FIG. 7C), and VIC-MR By Ti-phos (FIG. 7D) are shown.

Results show that the 2.5 mM does not elute as well as the 5 mM phosphate

Figure 8A:
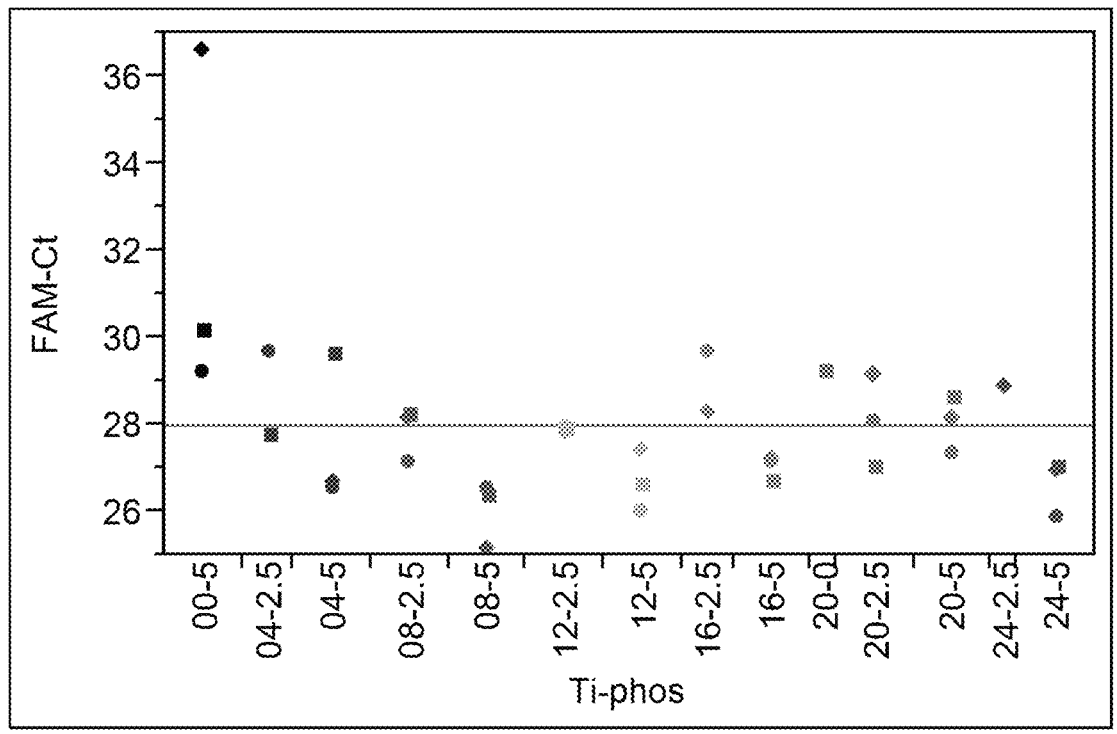
FIG. 8A-D shows the results of one way analysis of binding of RNA to CuTi coated particles with buffers of different phosphate concentrations.
Figure 8B:
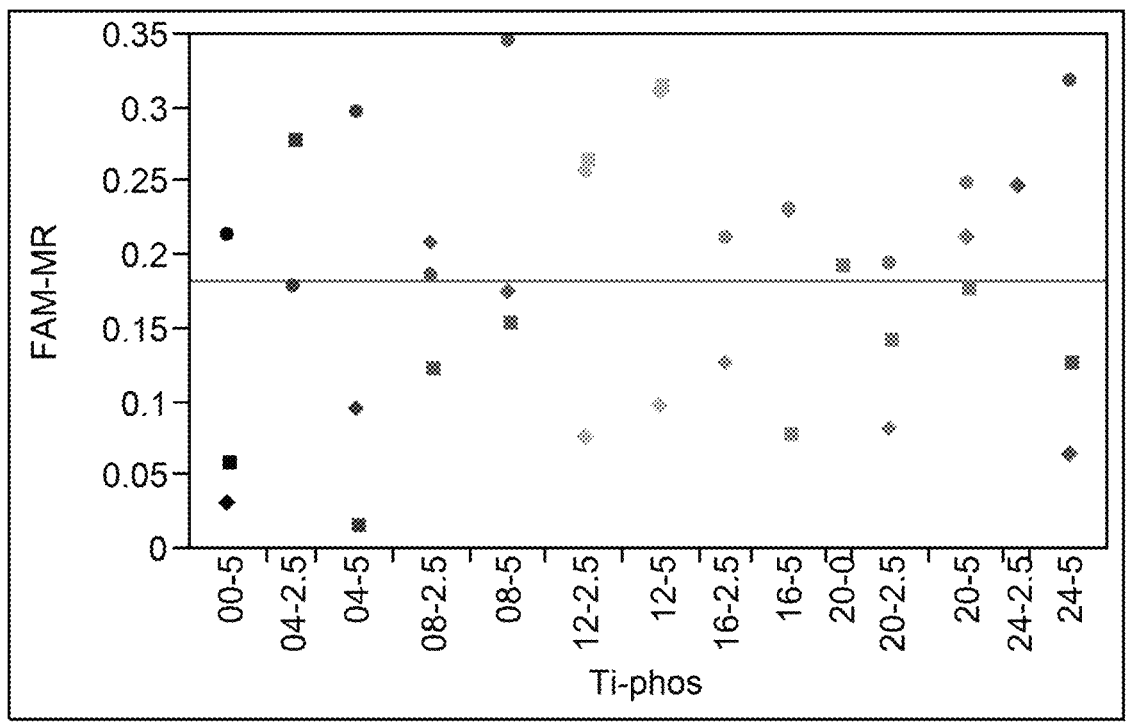
Figure 8C:
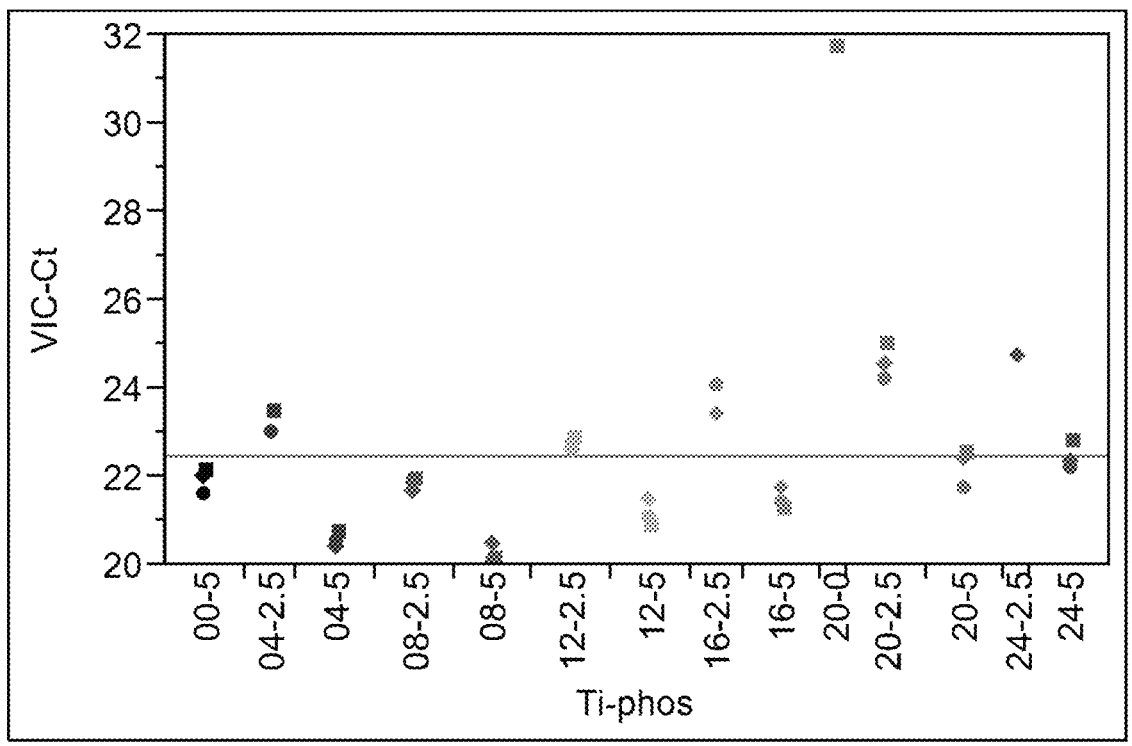
Figure 8D:
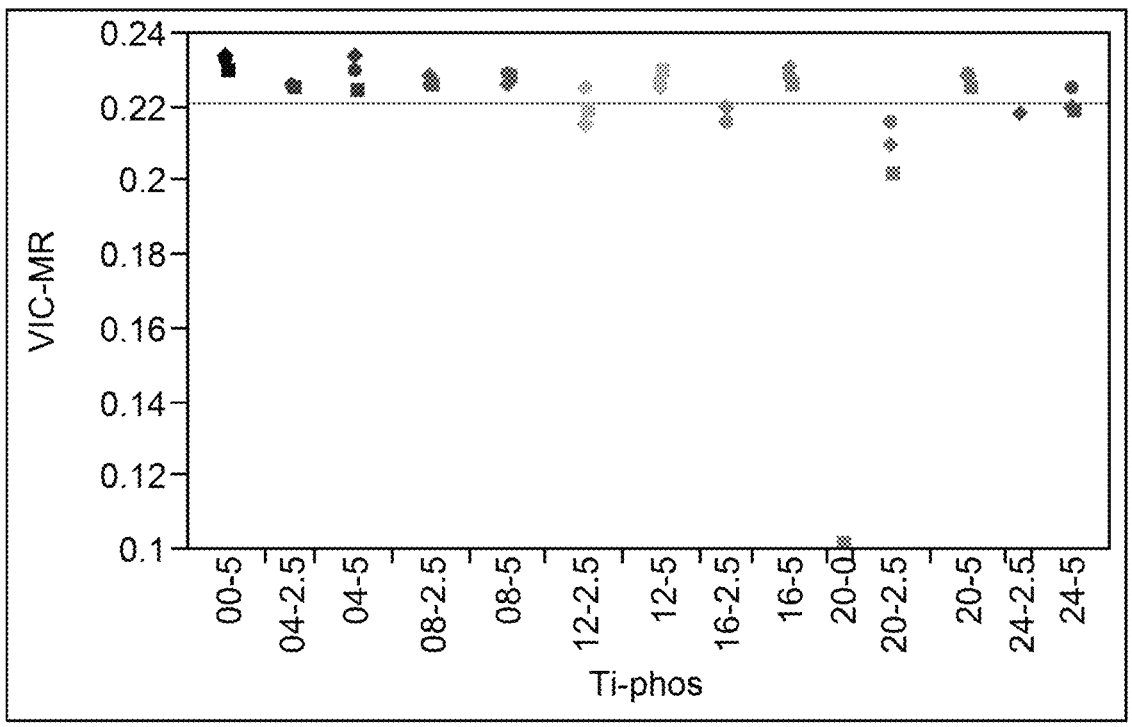
Figure 9A:
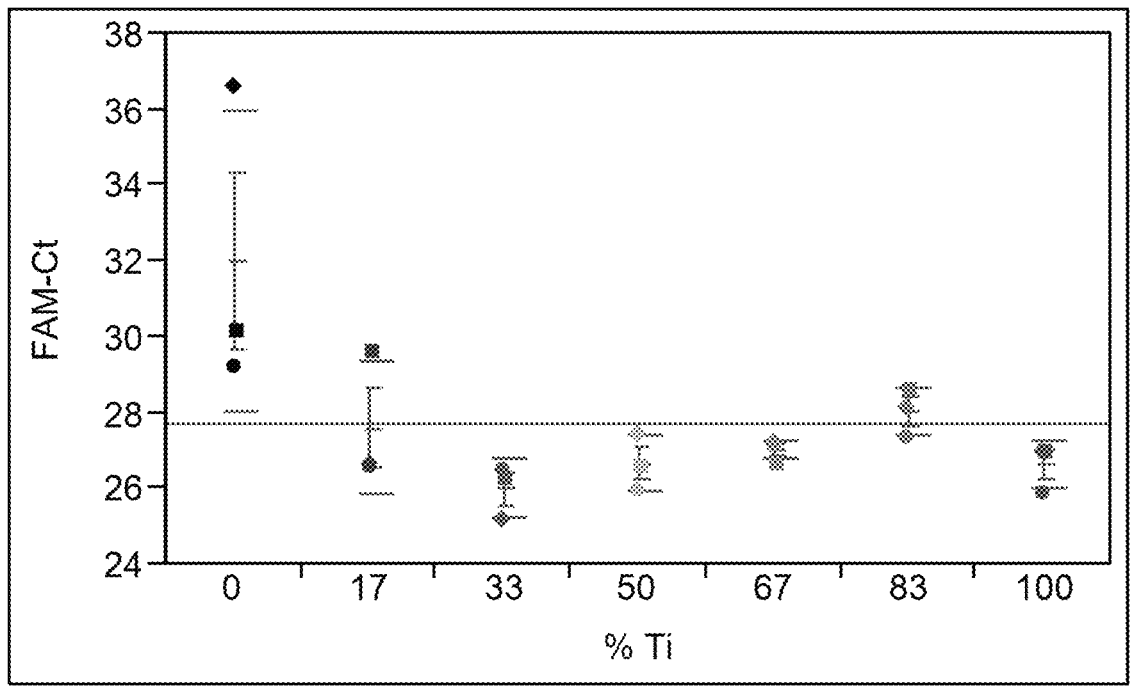
FIG. 9A-D shows the results of one way analysis of binding of RNA to CuTi coated particles with buffers of different phosphate concentrations and ratios of Cu to Ti.
Figure 9B:
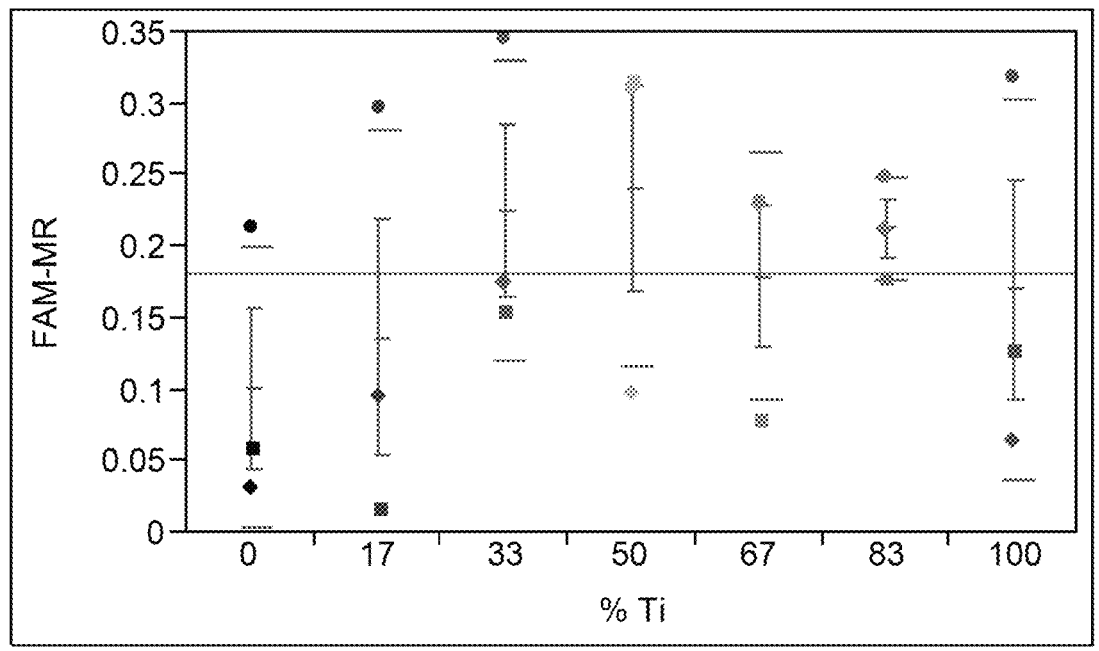
Figure 9C:
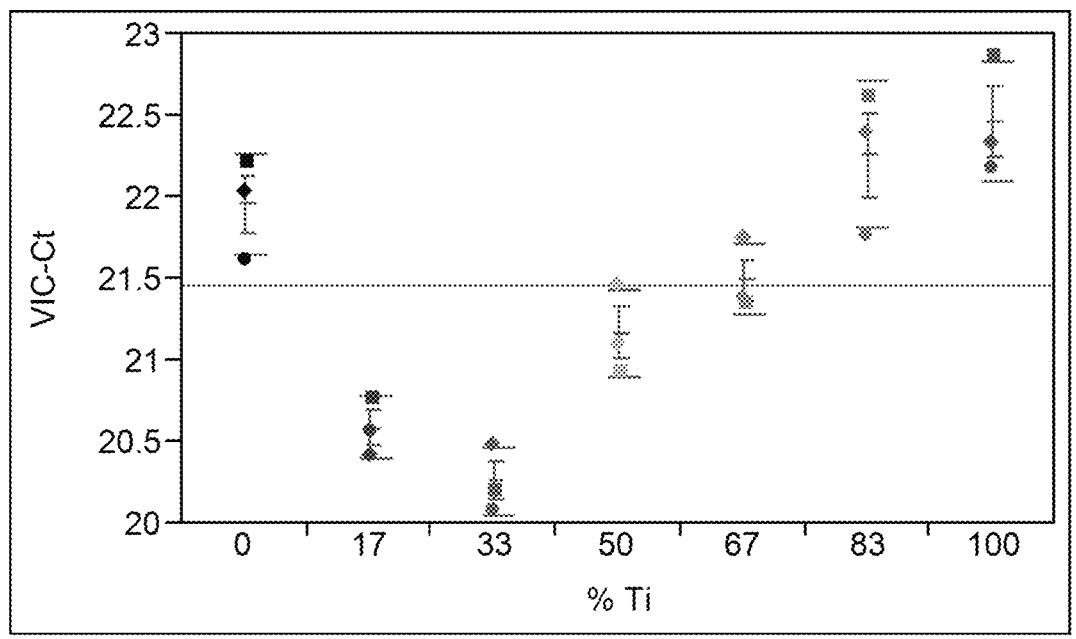
Figure 9D:
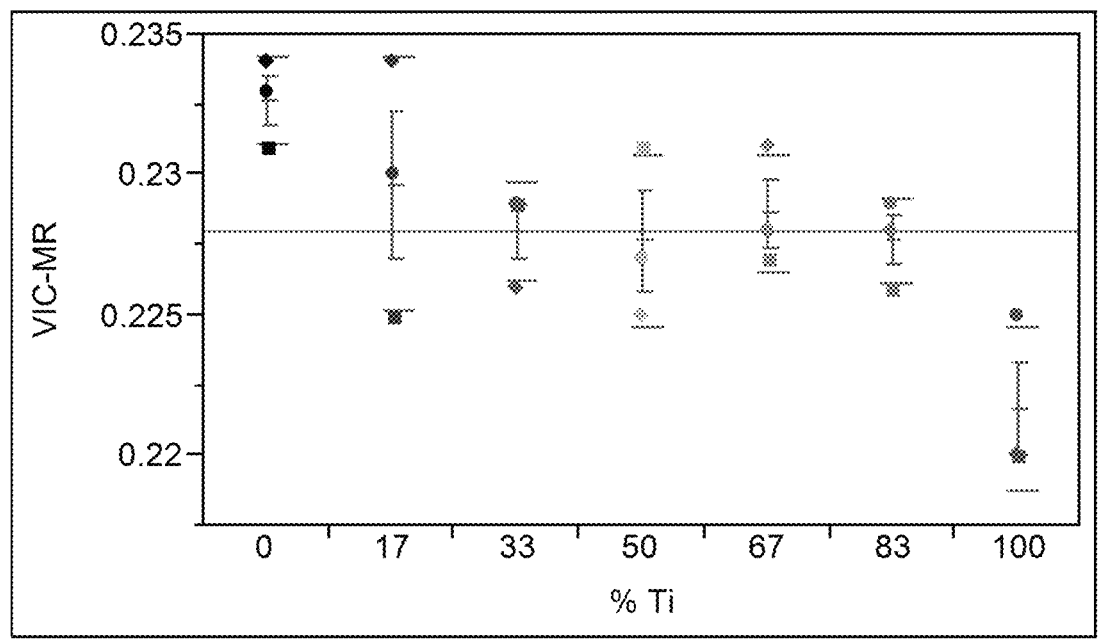

Results of oneway Analysis of FAM-Ct By Ti-phos (FIG. 8A), FAM-MR By Ti-phos (FIG. 8B), VIC-Ct By Ti-phos (FIG. 8C), and VIC-MR By Ti-phos (FIG. 8D) are shown. Results indicate that the 5 mM phosphate elution showed the Cu—Ti combination works better than the 100% Cu or the 100% Ti.

Results of oneway analysis of FAM-Ct by % Ti, oneway analysis of FAM-MR by % Ti, oneway analysis of VIC-Ct by % Ti, and oneway analysis of VIC-MR by % Ti are shown in FIGS. 9A-D.

The 5 mM phosphate elution showed that the Cu—Ti combination works better than the 100% Cu or the 100% Ti. The 33% Ti, 66% Cu works the best, most notably seen with the internal control.

Example 3

This example describes further analysis of Cu—Ti ratios.

The total concentration of Cu+Ti was 24 mM. Ti was varied from 11 mM to 5 mM and Cu was varied from 13 to 19 mM, respectively.

Reagents

| Common Name | Vendor |
|---|---|
| Copper(II) chloride | Sigma-Aldrich |
| HCl 12M | Sigma-Aldrich |
| Iron Oxide-black | Rockwood |
| Potassium phosphate dibasic | Sigma-Aldrich |
| Sodium Hydroxide 50% | Sigma-Aldrich |

-continued

| Common Name | Vendor |
|---|---|
| Sodium Hydroxide 5N | Fisher |
| Sodium Phosphate dibasic | Sigma-Aldrich |
| Titanium(III) chloride solution | Sigma-Aldrich |

$CuCl_2$ was prepared with HCl similar to the $TiCl_3$. One liter of 10 mM NaOH was prepared. Cu—Ti solutions were prepared by mixing $CuCl_2$ and $TiCl_3$ into single tubes prior to adding to particles. NaOH was added after particles are filtered. The below table shows the concentration of Cu and Ti in the different samples tested.

| Bottle | 1 | 2 | 3 | 4 | 5 | 6 |
|---|---|---|---|---|---|---|
| ml Ti | 1.05 | 0.95 | 0.86 | 0.67 | 0.57 | 0.48 |
| ml Cu | 1.3 | 1.4 | 1.5 | 1.7 | 1.8 | 1.9 |
| ml NaOH | 3 | 3 | 3 | 3 | 3 | 3 |
| mM Ti | 11 | 10 | 9 | 7 | 6 | 5 |
| mM Cu | 13 | 14 | 15 | 17 | 18 | 19 |
| mM NaOH | 582 | 582 | 582 | 582 | 582 | 582 |

Particles were prepared by weighing out 6 aliquots of 10 g particles (Rockwood BK5000AP), dispensing each into a 125 ml PETG bottle, and adding 100 ml water to each bottle. The Cu—Ti solution was added to each bottle, shaken vigorously and put on rotator. All the particle suspensions were filtered through a 100 micron nylon filter (Spectramesh #146488 (Spectrum Labs)). Fifty ml water was added to each bottle after pouring over filter, shaking, and poured over filter to combine. Particles were returned to a clean PETG bottle. Three ml of 50% NaOH was added to each bottle of particles and bottles were placed on the rotator. Particles were captured magnetically, the fluid was decanted, and particle were washed 5 time with 100 ml water. A 6th Wash was performed with ~100 ml of 10 mM NaOH. The fluid was decanted and particles were re-suspended to total volume of 100 ml 10 mM NaOH.

The particles were tested for RNA binding. Four mM phosphate was used for elution. IC was in the lysis buffer. Samples were prepared at ~3xLOD (final concentration of HCV was 45 IU/ml)

Extractions were performed as described in the below table.

| Loading | Lysis Buffer + IC | MMP as listed below | Sample | LB as Wash1 | Wash2 | Elution 4 mM phosphate | temp |
|---|---|---|---|---|---|---|---|
| Well 1-lysis | 1.5 ml | 100 ul | 0.5 ml | | | | 50 C. |
| Well 2 | | | | | | | |
| Well 3 | | | | | | | |
| Well 4-Wash1 | | | | 0.7 ml | | | |
| Well 5-Wash2A | | | | | 0.8 ml | | |
| Well 6-Wash2B | | | | | 0.8 ml | | |
| Elution-43 ul | | | | | | 43 ul | 73 C. |

Figure 10A:
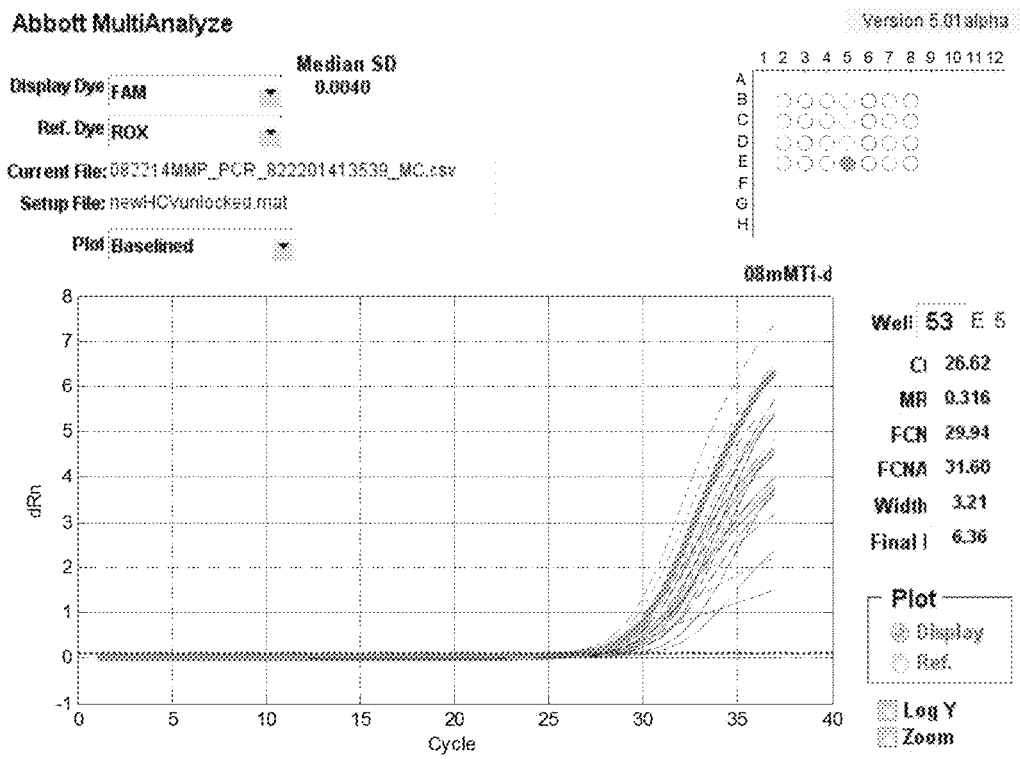
FIG. 10A-B shows the binding of RNA to CuTi coated particles.
Figure 10B:
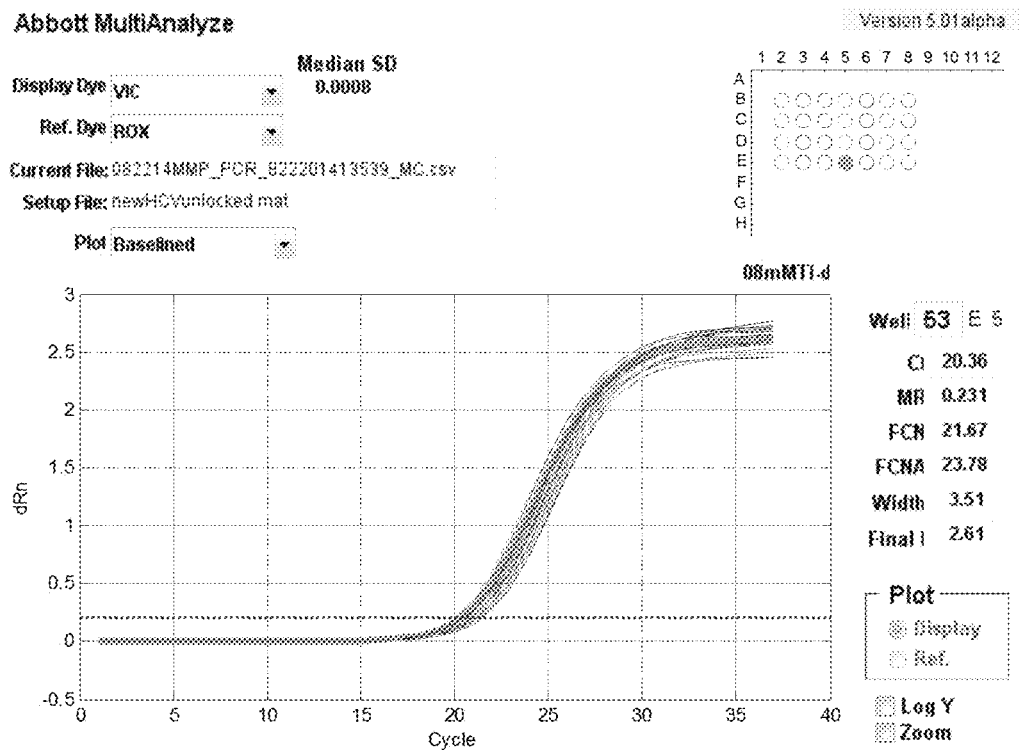
Figure 11A:
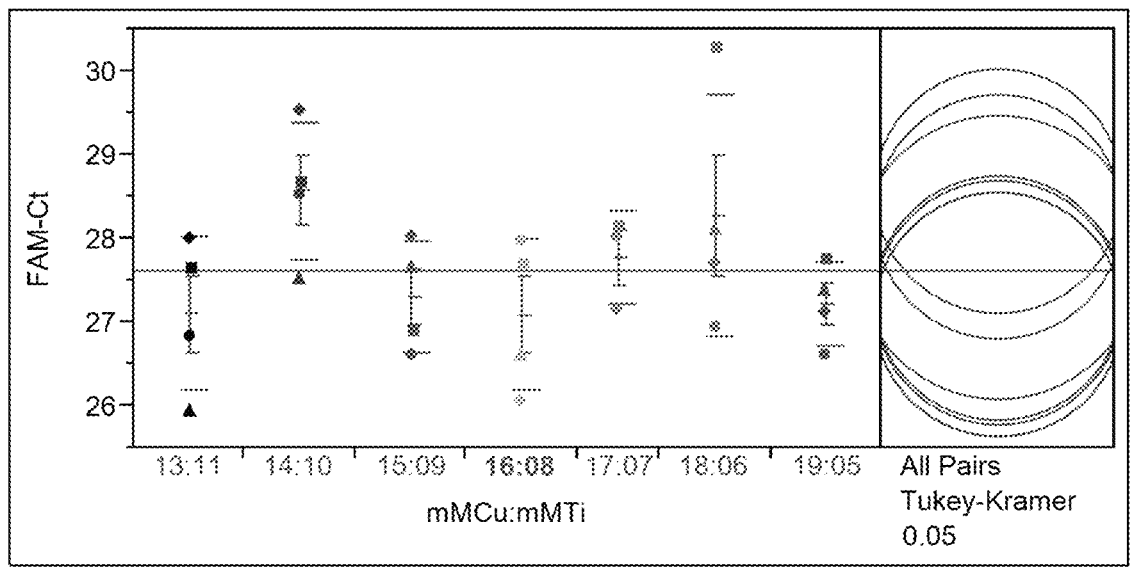
FIG. 11A-D shows the results of one way analysis of binding of RNA to CuTi coated particles with different ratios of Cu to Ti.
Figure 11B:
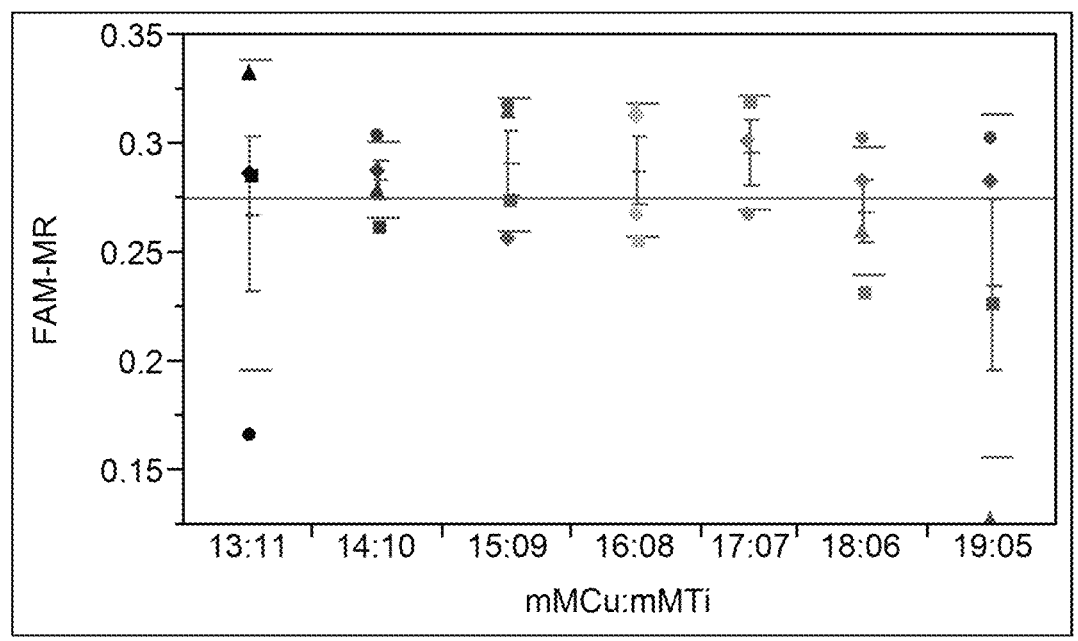
Figure 11C:
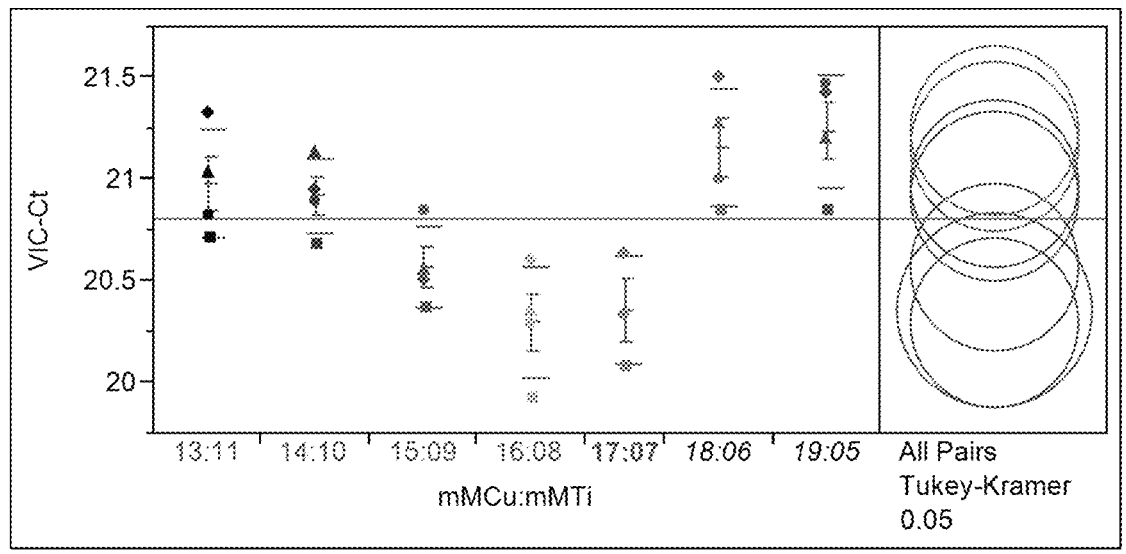
Figure 11D:
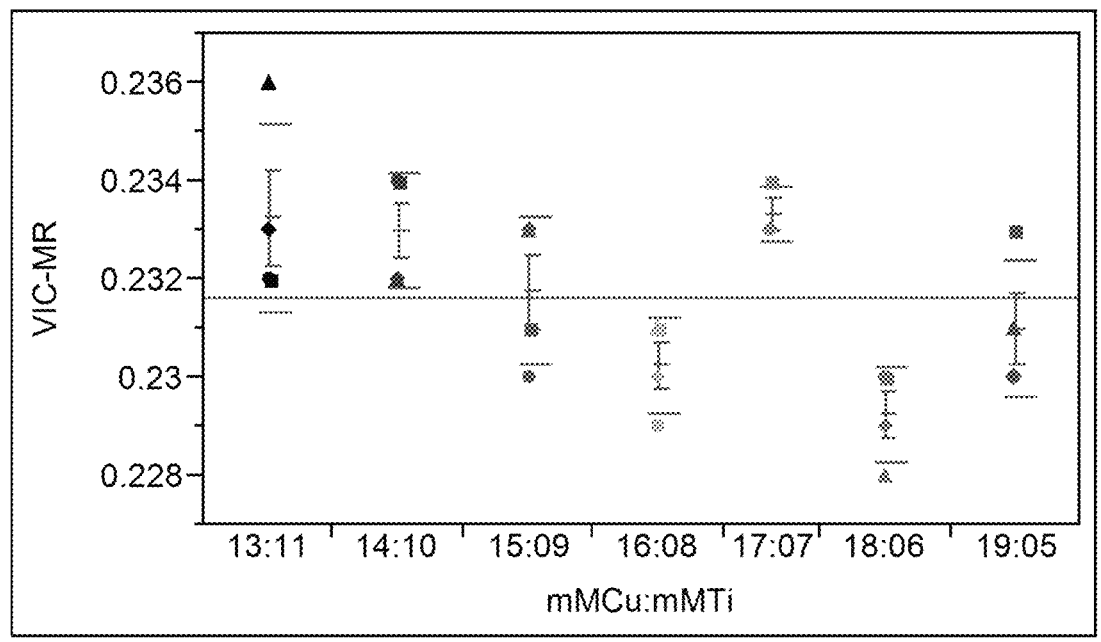

After amplification, data was analyzed by MultiAnalyze (FIGS. 10A-B) and JMP. Oneway analysis of FAM-Ct by mMCu:mMTi, oneway analysis of FAM-MR by mMCu:mMTi, oneway analysis of VIC-Ct by mMCu:mMTi, and oneway analysis of VIC-MR by mMCu:mMTi is shown in FIGS. 11A-D.

The FAM signals are not significantly different, which is due to the low titer of the samples and the variability of the assay at that level. The lowest overall CT value is at the Cu:Ti ratio of 16 mM Cu to 8 mM Ti or 2:1. These particles also show the lowest CT value for the internal control.

Example 4

This example describes an analysis of the overall amount of precipitate using the 16:08 Cu:Ti ratio.

Reagents

| Common Name | Vendor |
|---|---|
| Copper(II) chloride | Sigma-Aldrich |
| HCl 12M | Sigma-Aldrich |
| Iron Oxide-black | Rockwood |
| Potassium phosphate dibasic | Sigma-Aldrich |
| Sodium Hydroxide 50% | Sigma-Aldrich |
| Sodium Hydroxide 5N | Fisher |
| Sodium Phosphate dibasic | Sigma-Aldrich |
| Titanium(III) chloride solution | Sigma-Aldrich |

$CuCl_2$ was prepared with HCl similar to the $TiCl_3$. Eight ml of the $CuCl_2$ and 3.8 ml $TiCl_3$ solution were prepared. The below Table shows the amount of Cu and Ti in each sample.

Particles were prepared by weighing out 6 aliquots of 10 g particles (Rockwood BK5000AP), dispensing each into a 125 ml PETG bottle, and adding 100 ml water to each bottle. Cu—Ti solution was added to each bottle, shaken vigorously, and put on rotator. All the particle suspensions were filtered through a 100 micron nylon filter (Spectramesh #146488 (Spectrum Labs). Fifty ml water to was added to bottle after pouring over filter, shaking, and pouring over filter to combine. Particles were returned to a clean PETG bottle. The calculated amount of 50% NaOH was added to each bottle of particles. Bottles were place all on rotator. Particles were magnetically captured, the fluid was decanted, and particles were washed 5 times with 100 ml water. A $6^{th}$ Wash with ~100 ml of 10 mM NaOH was performed. The fluid was decanted and particles were resuspended to a total volume of 100 ml in 10 mM NaOH The particles were tested for RNA elution using 5 mM phosphate for elution. Reagents were prepared as described above. IC was in the lysis buffer. Samples were prepared at ~3xLOD (final concentration of HCV was 45 IU/ml).

Extractions were performed as described in the Table below.

| Bottle | 1 | 2 | 3 | 4 | 5 | 6 | |
|---|---|---|---|---|---|---|---|
| ml Cu—Ti | 2.12 | 1.89 | 1.65 | 1.42 | 1.18 | 0.95 | |
| ml NaOH | 2.7 | 2.4 | 2.1 | 1.8 | 1.5 | 1.2 | |
| mM Ti | 7.170518 | 6.392585 | 5.590975 | 4.792747 | 3.99452 | 3.196292 | |
| mM Cu | 14.15948 | 12.62331 | 11.04039 | 9.464143 | 7.887899 | 6.311655 | |
| mM NaOH | 523.8 | 465.6 | 407.4 | 349.2 | 291 | 232.8 | |
| mM CuTi | 21.33 | 19.01589 | 16.63136 | 14.25689 | 11.88242 | 9.507947 | |
| 100% | 90% | 80% | 70% | 60% | 50% | 40% | % original |
| 24 | 21.6 | 19.2 | 16.8 | 14.4 | 12 | 9.6 | mM Cu |

| Loading | Lysis Buffer + IC | MMP as listed below | Sample | LB as Wash1 | Wash2 | Elution 5 mM phosphate | temp |
|---|---|---|---|---|---|---|---|
| Well 1-lysis | 1.5 ml | 100 ul | 0.5 ml | | | | 50 C. |
| Well 2 | | | | | | | |
| Well 3 | | | | | | | |
| Well 4-Wash1 | | | | 0.7 ml | | | |
| Well 5-Wash2A | | | | | 0.8 ml | | |
| Well 6-Wash2B | | | | | 0.8 ml | | |
| Elution-45 ul | | | | | | 45 ul | 73 C. |

Figure 12A:
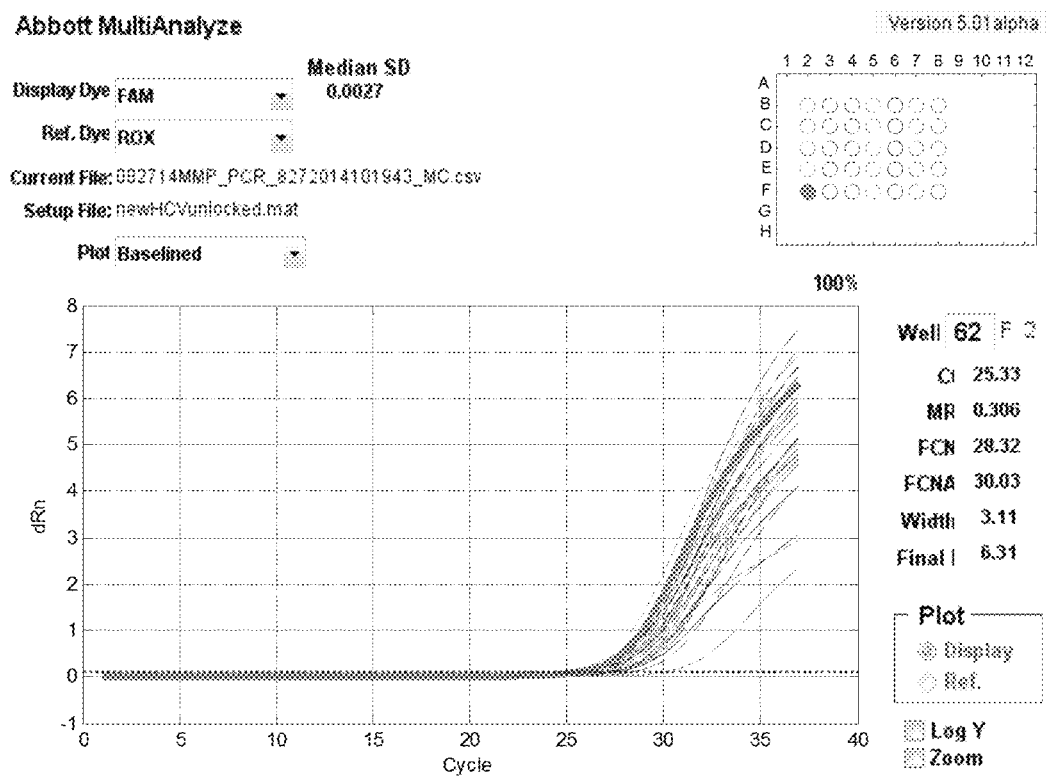
FIG. 12A-B shows the binding of RNA to CuTi coated particles.
Figure 12B:
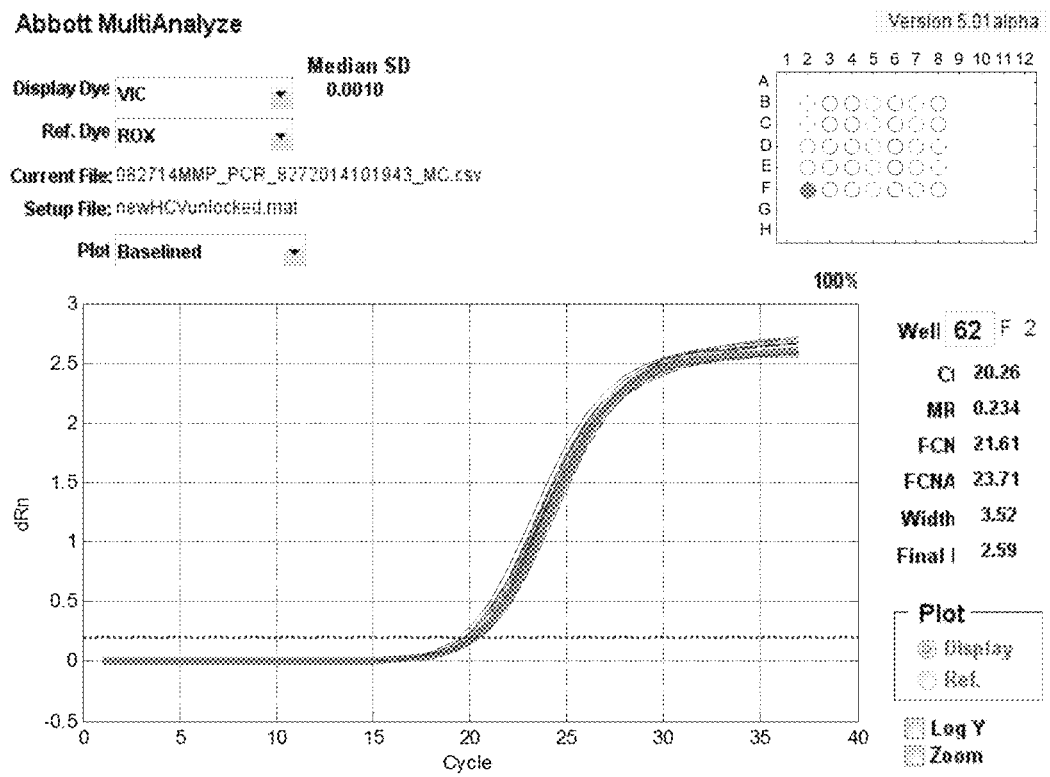
Figure 13A:
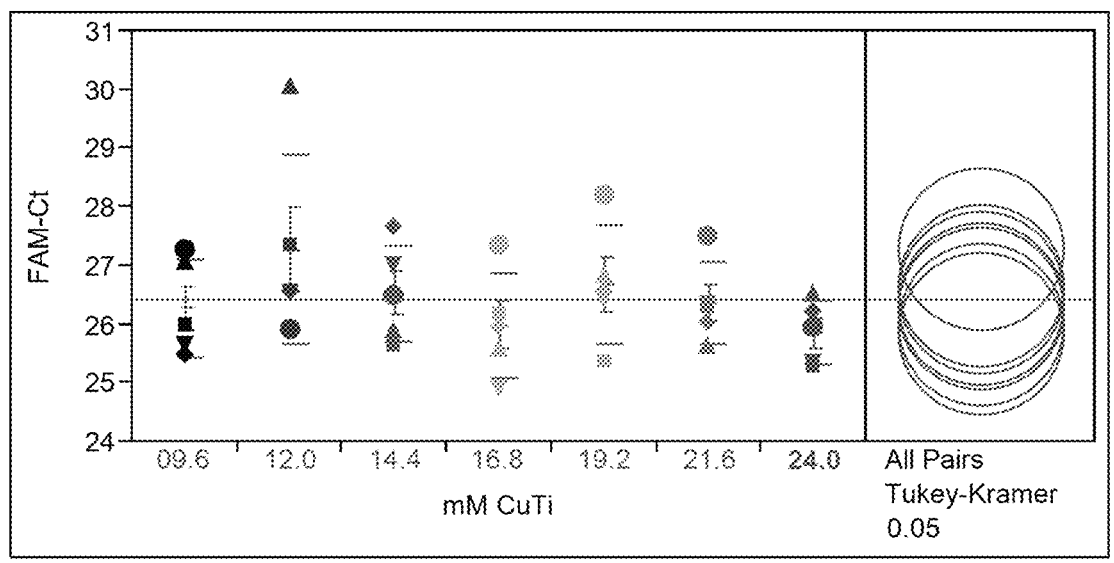
FIG. 13A-D shows the results of one way analysis of binding of RNA to CuTi coated particles with different ratios of Cu to Ti.
Figure 13B:
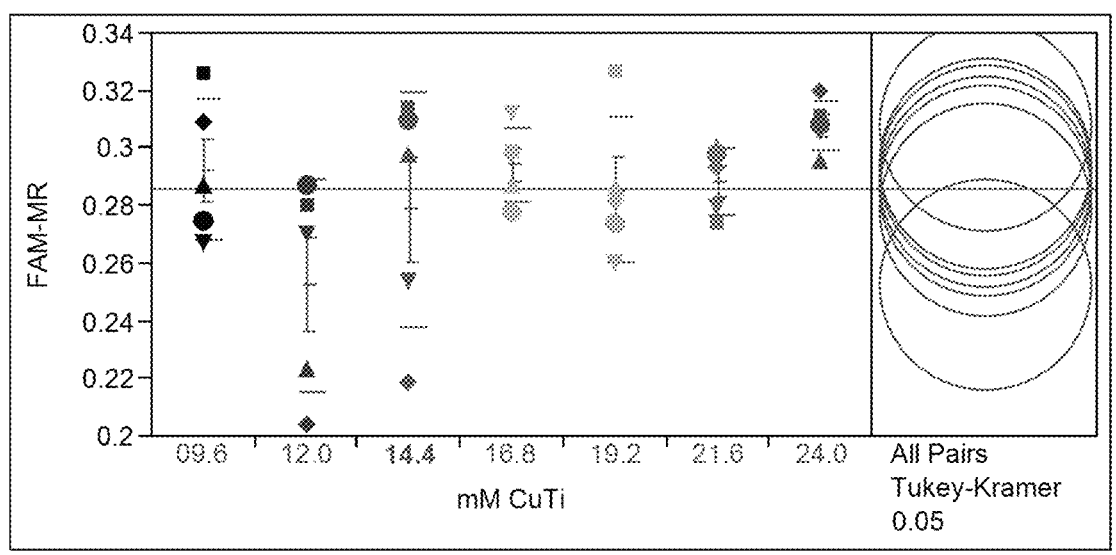
Figure 13C:
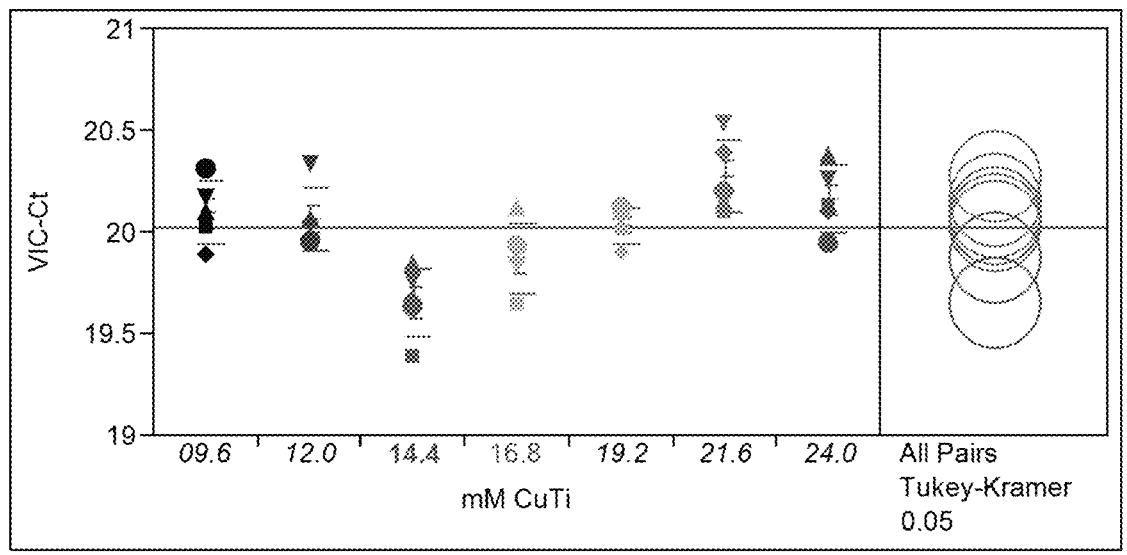
Figure 13D:
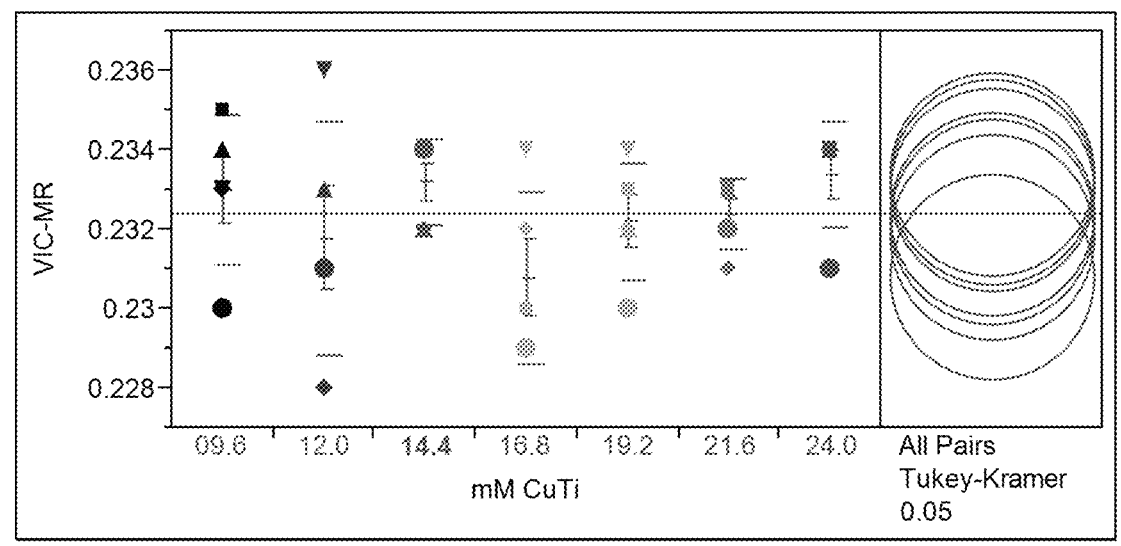

After amplification, data was analyzed using MultiAnalyze. (FIGS. 12A-B) and JMP. Oneway analysis of FAM-Ct by mM CuTi, oneway analysis of FAM-MR by mM CuTi, oneway analysis of VIC-Ct by mM CuTi, and oneway analysis of VIC-MR by mM CuTi is shown in FIGS. 13A-D.

Results showed that the FAM signals were not significantly different, which is due to the low titer of the samples and the variability of the assay at that level. The optimum IC value was with particles with 14.4 mM CuTi.

Example 5

This example describes an analysis of particles made with 17 mM and 14 mM CuTi against particles made with 24 mM CuTi. The Table below shows samples tested.

| Loading | Lysis Buffer + IC | MMP as listed below | Sample | LB as Wash1 | Wash2 | Elution 5 mM phospha | temp |
|---|---|---|---|---|---|---|---|
| Well 1-lysis | 1.5 ml | 100 ul | 0.5 ml | | | | 50 C. |
| Well 2 | | | | | | | |
| Well 3 | | | | | | | |
| Well 4-Wash1 | | | | 0.7 ml | | | |
| Well 5-Wash2A | | | | | 0.8 ml | | |
| Well 6-Wash2B | | | | | 0.8 ml | | |
| Elution-45 ul | | | | | | 45 ul | 73 C. |

Figure 14A:
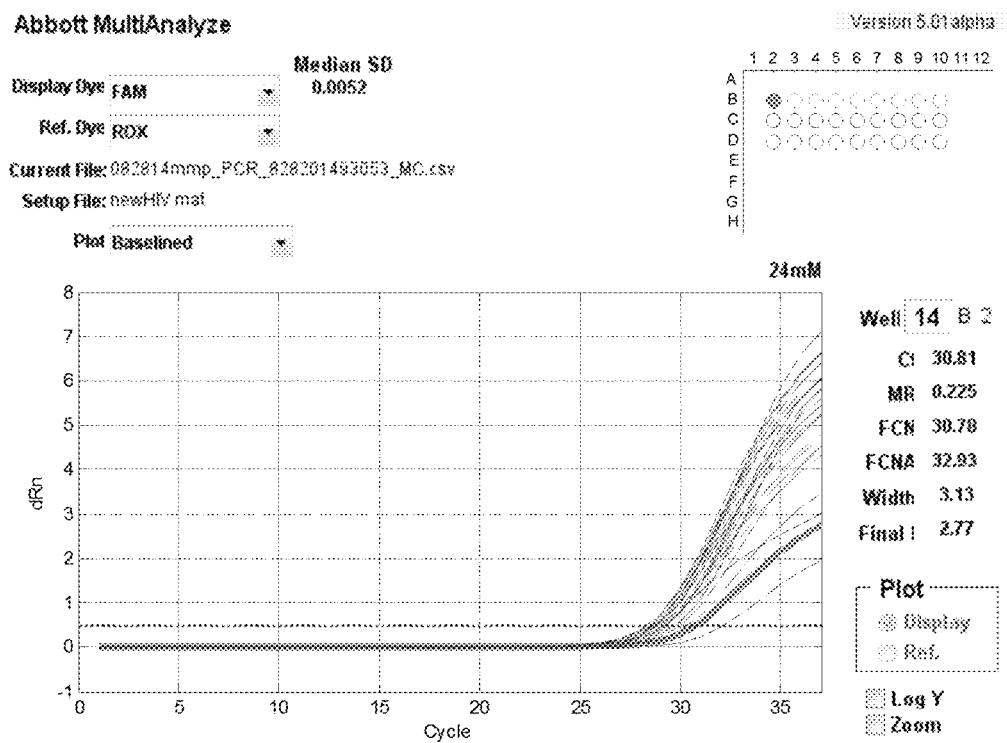
FIG. 14A-B shows the binding of RNA to CuTi coated particles.
Figure 14B:
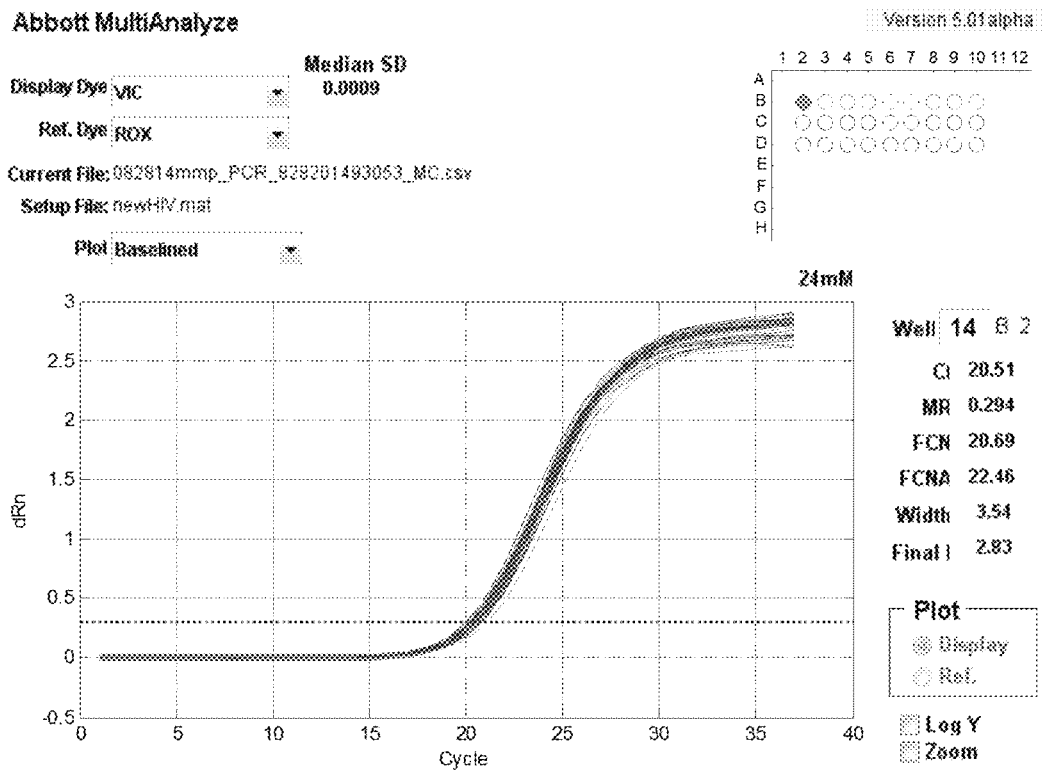
Figure 15A:
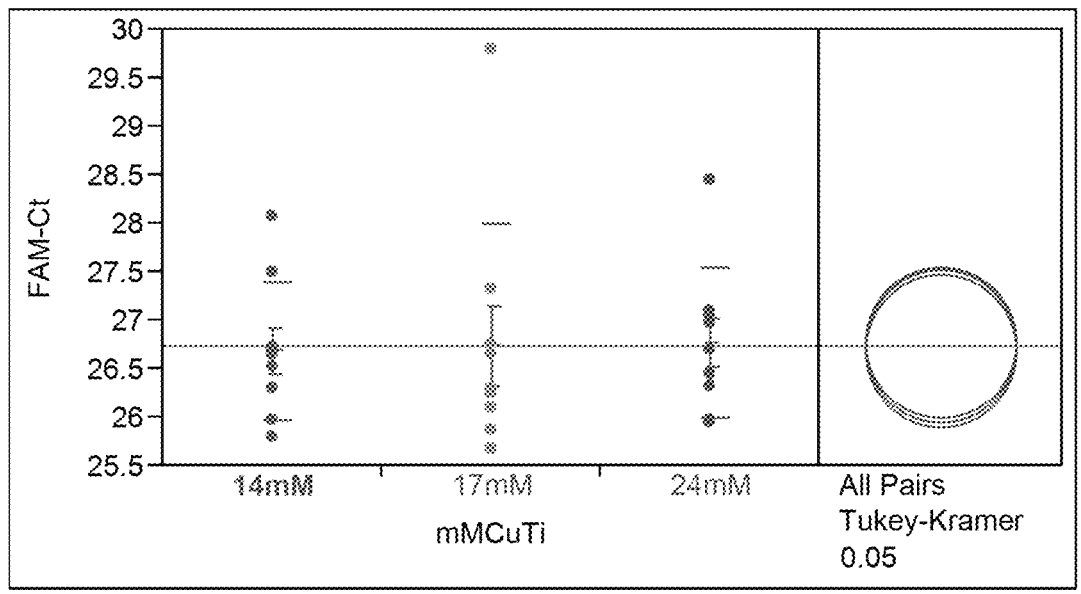
FIG. 15A-D shows the results of one way analysis of binding of RNA to CuTi coated particles with different sized particles.
Figure 15B:
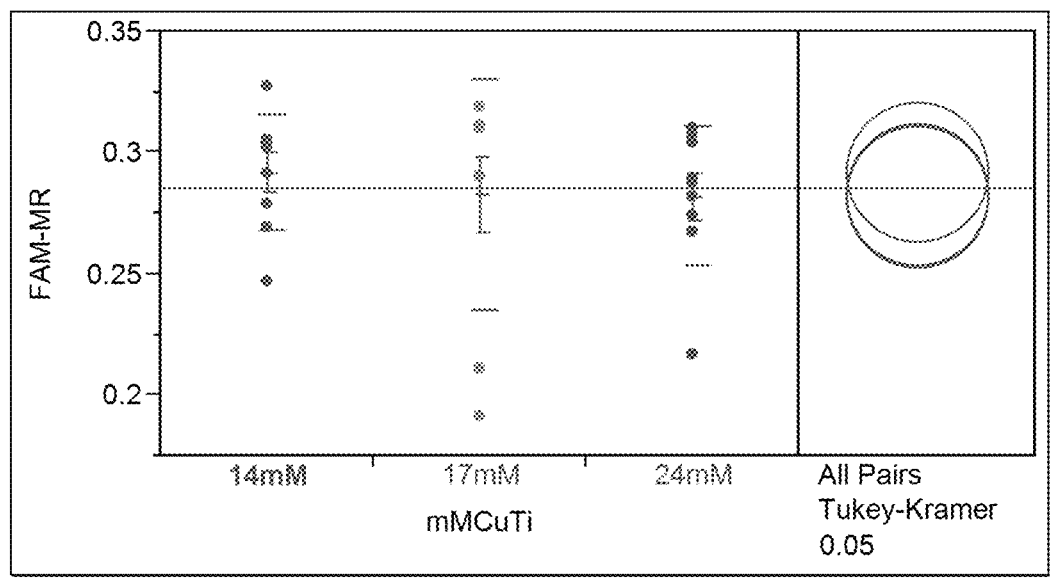
Figure 15C:
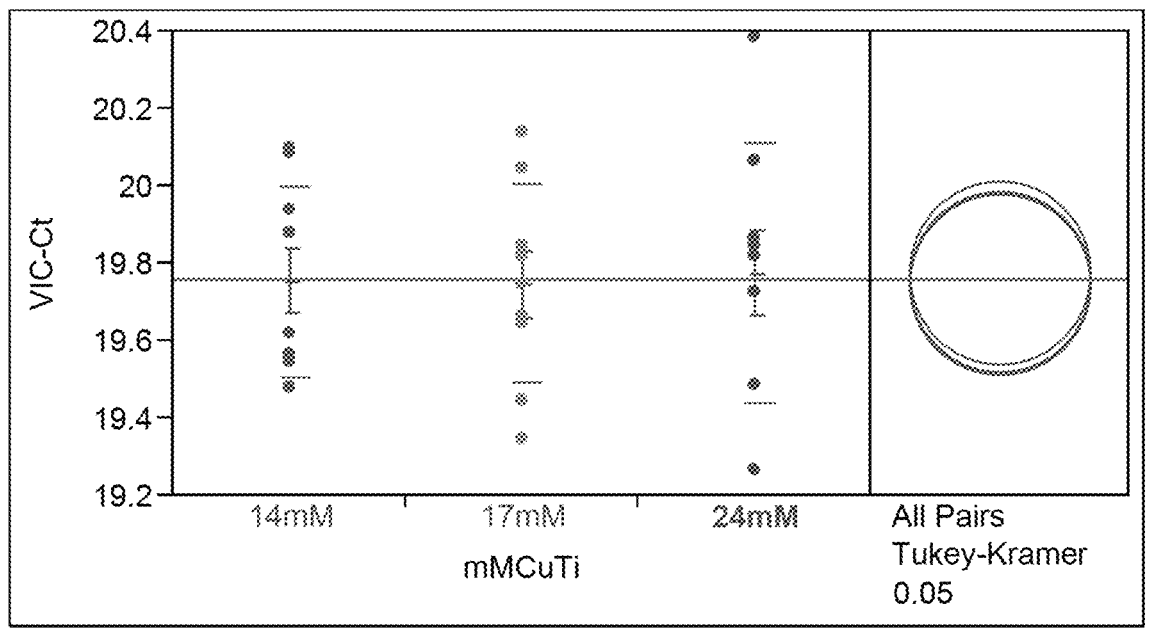
Figure 15D:
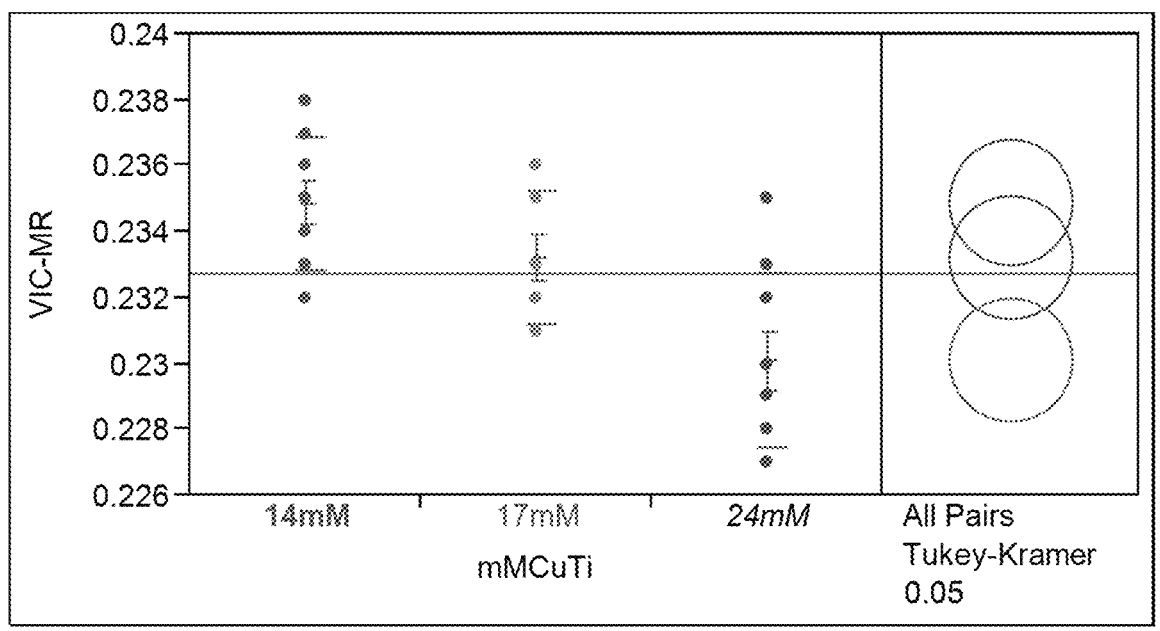

HCV capture was performed. After amplification, data was analyzed using MultiAnalyze (FIG. 14A-B) and JMP. Oneway analysis of FAM-Ct by mMCuTi, oneway analysis of FAM-MR by mMCuTi, oneway analysis of VIC-Ct by mMCuTi, and oneway analysis of VIC-MR by mMCuTi is shown in FIGS. 15A-D.

For the FAM signal, there was no significant difference between the three particle batches. For the VIC signal, there was no significant difference between the three particle batches for the VIC CT but the 14 and 17 mM CuTi particles have a higher MR than the 24 mM CuTi particles.

Phosphate Concentration and Elution.

Figure 16A:
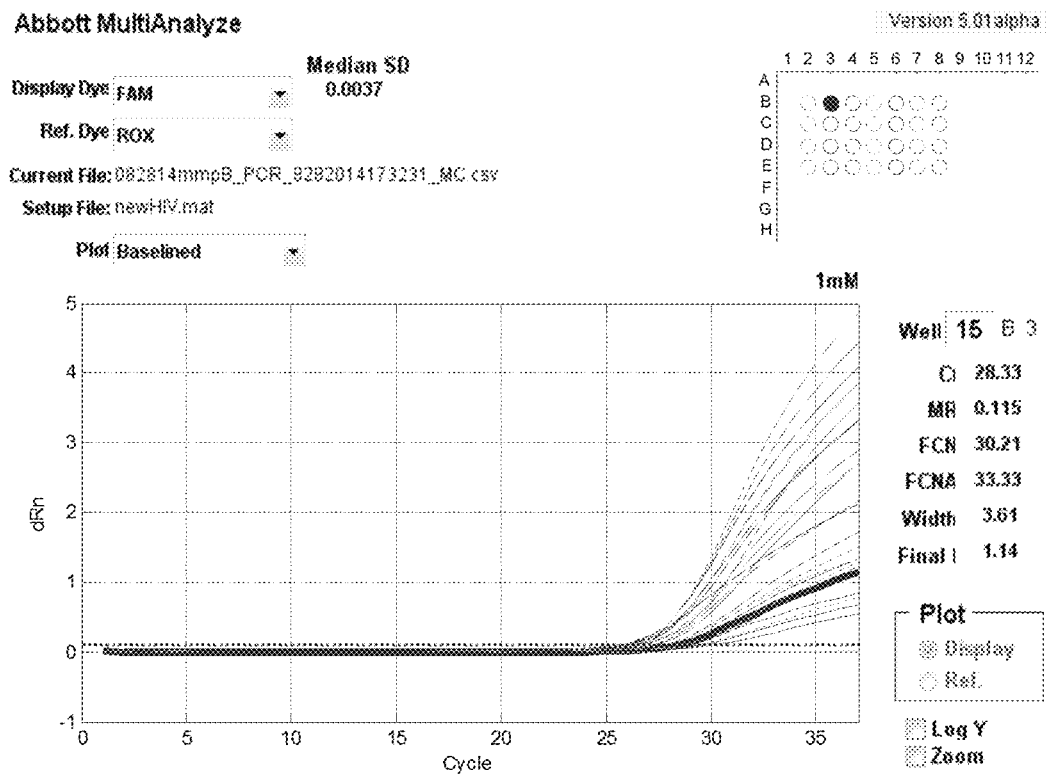
FIG. 16A-B shows the binding of RNA to CuTi coated particles.
Figure 16B:
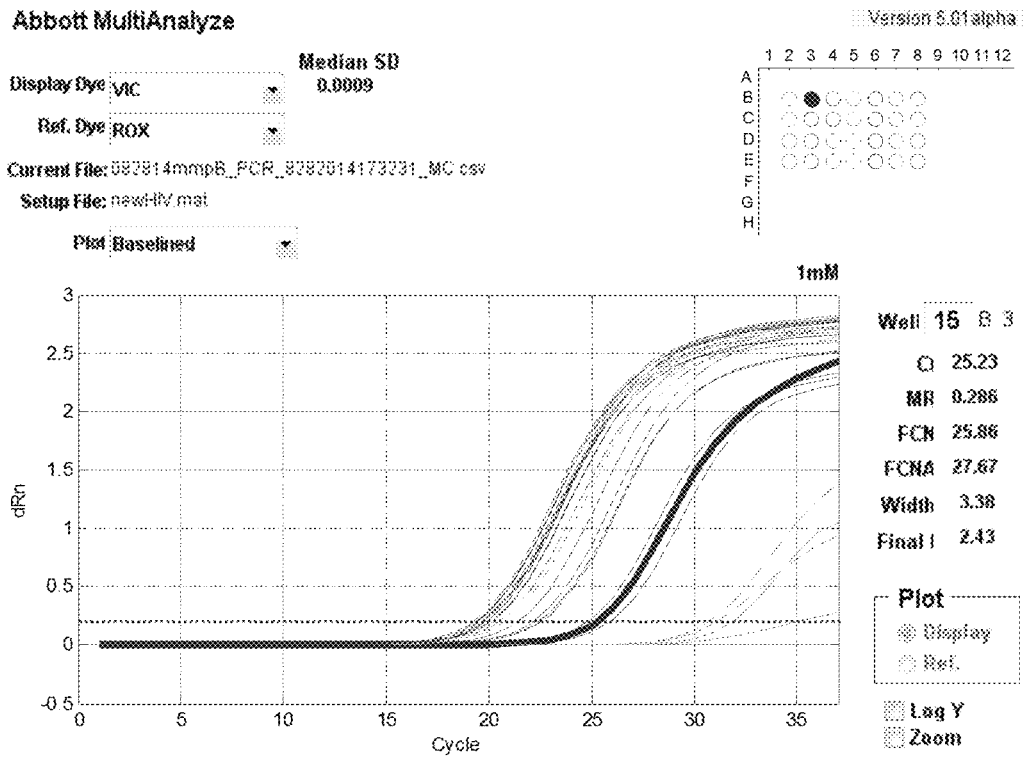
Figure 17A:
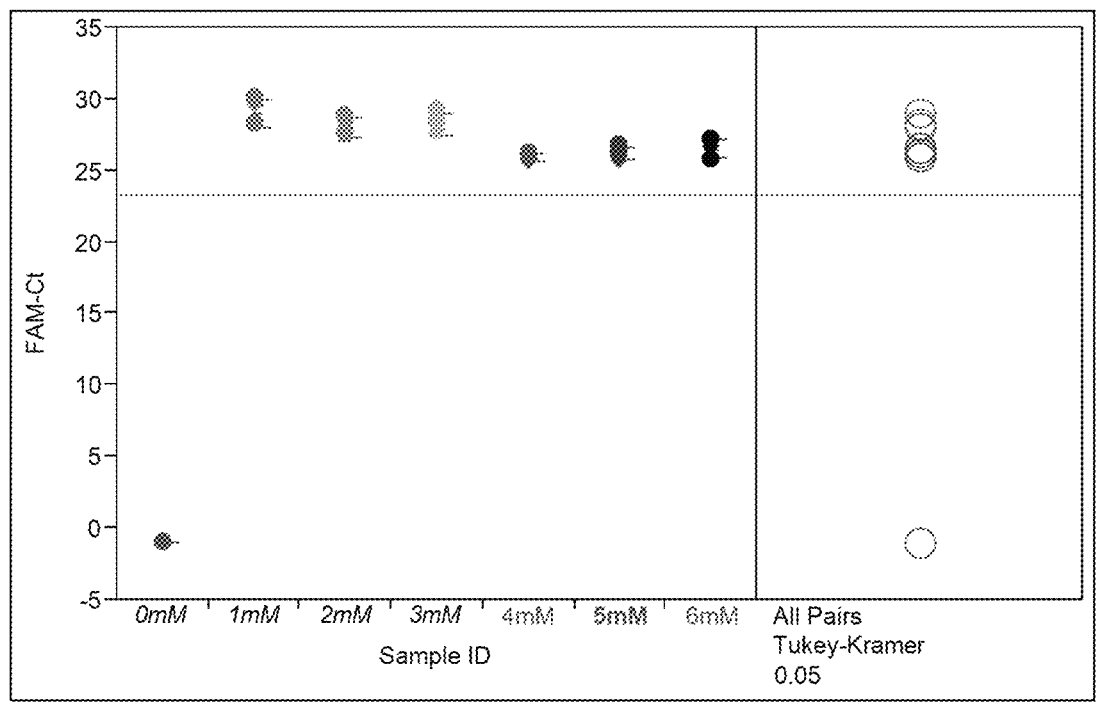
FIG. 17A-D shows the results of one way analysis of elution of RNA from CuTi coated particles with buffers of different phosphate concentrations.
Figure 17B:
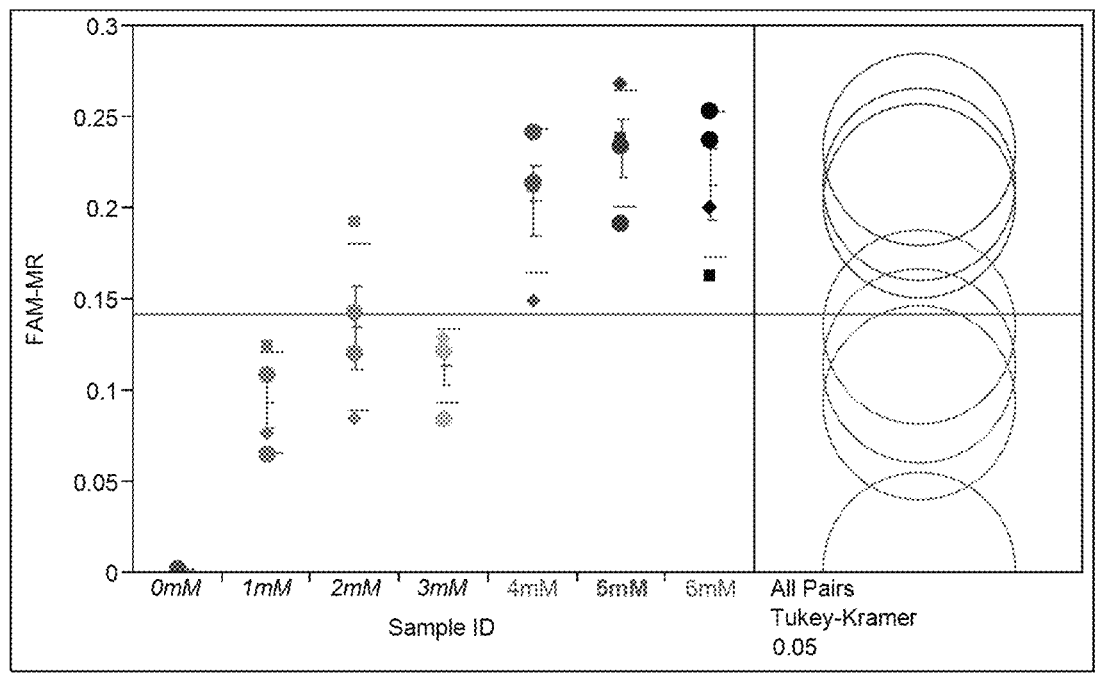
Figure 17C:
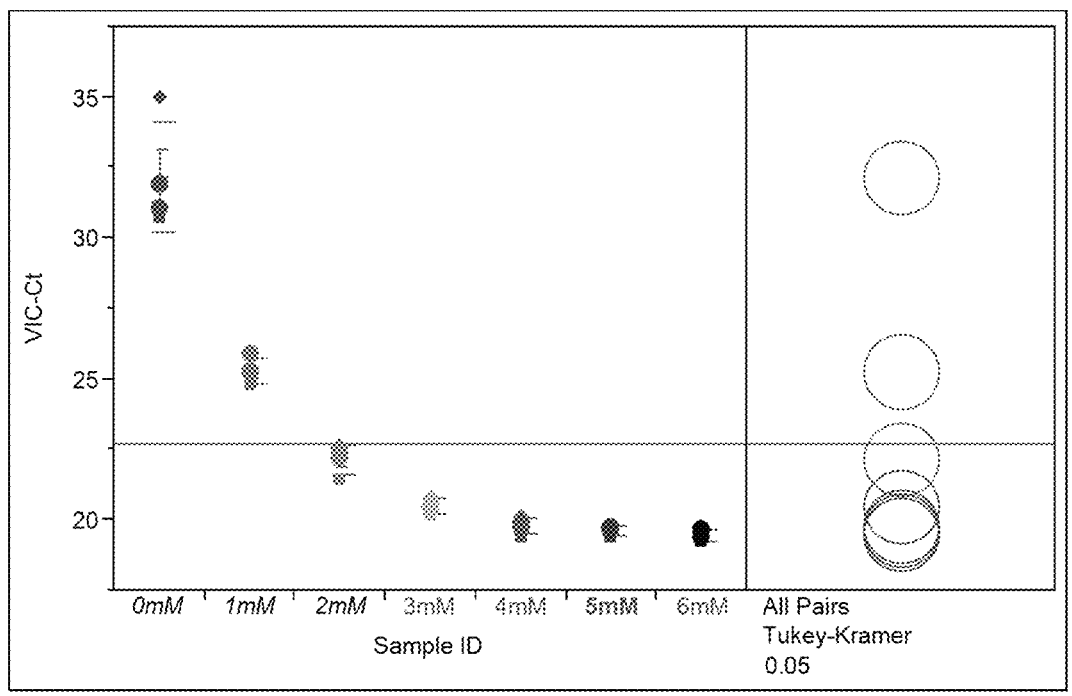
Figure 17D:
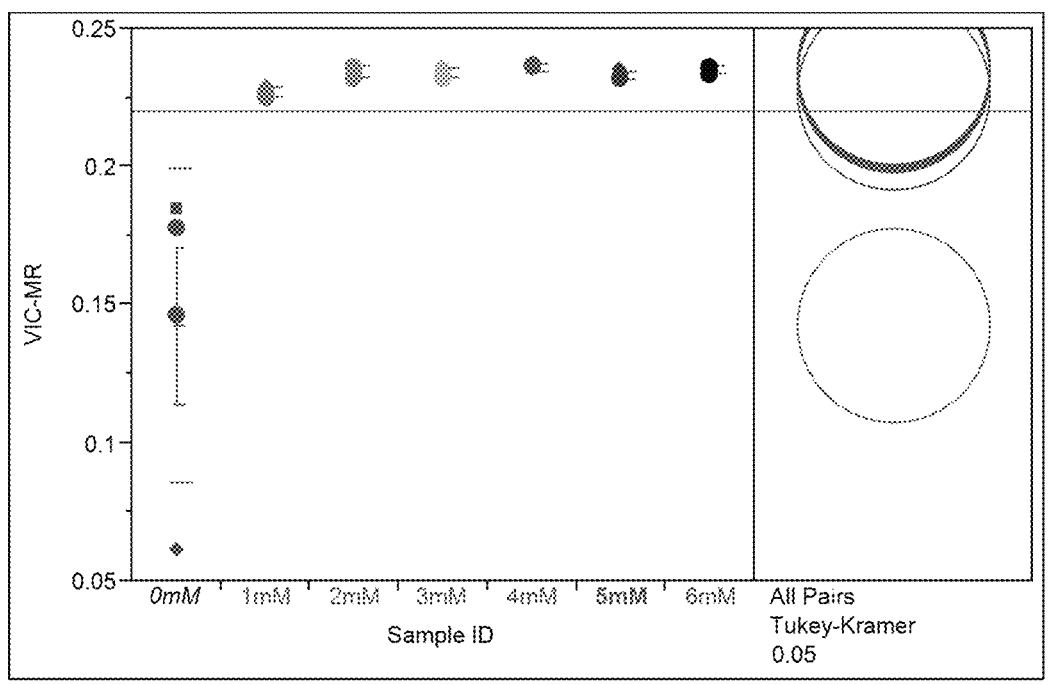

Experiments were performed to test the amount of phosphate needed to elute target from particles. Dilutions of elution buffer were made using water. Extractions and HCV capture assays were performed as described above. Data was analyzed using Multianalyze (FIG. 16A-B) and JMP. Oneway analysis of FAM-Ct by Sample ID, oneway analysis of FAM-MR by Sample ID, oneway analysis of VIC-Ct by Sample ID, and oneway analysis of VIC-MR by Sample ID is shown in FIGS. 17A-D.

Results shown that the FAM and VIC CT and MR are identical at 4, 5, and 6 mM phosphate.

Example 6

This example describes analysis of how well the CuTi coated particles bind DNA and RNA. HBV DNA and HCV RNA were used as the targets. Results were compared with iron oxide and silica particles. All samples were eluted using 5.7 mM phosphate buffer.

HBV Extraction and Assay

Target HBV CalB 6.6 log IU/ml and IC at 36 µl per sample (10× concentration) were used. Extractions were done with a 58° C. lysis temperature.

Figure 18A:
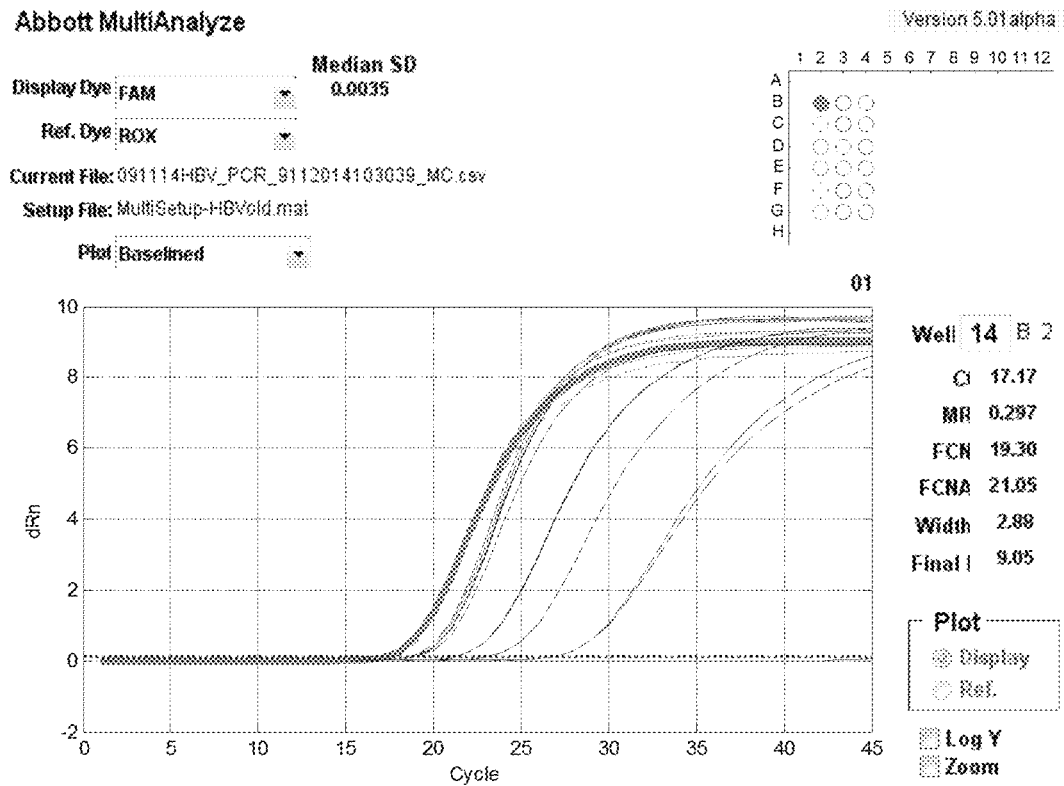
FIG. 18A-B shows the binding of RNA to CuTi coated particles.
Figure 18B:
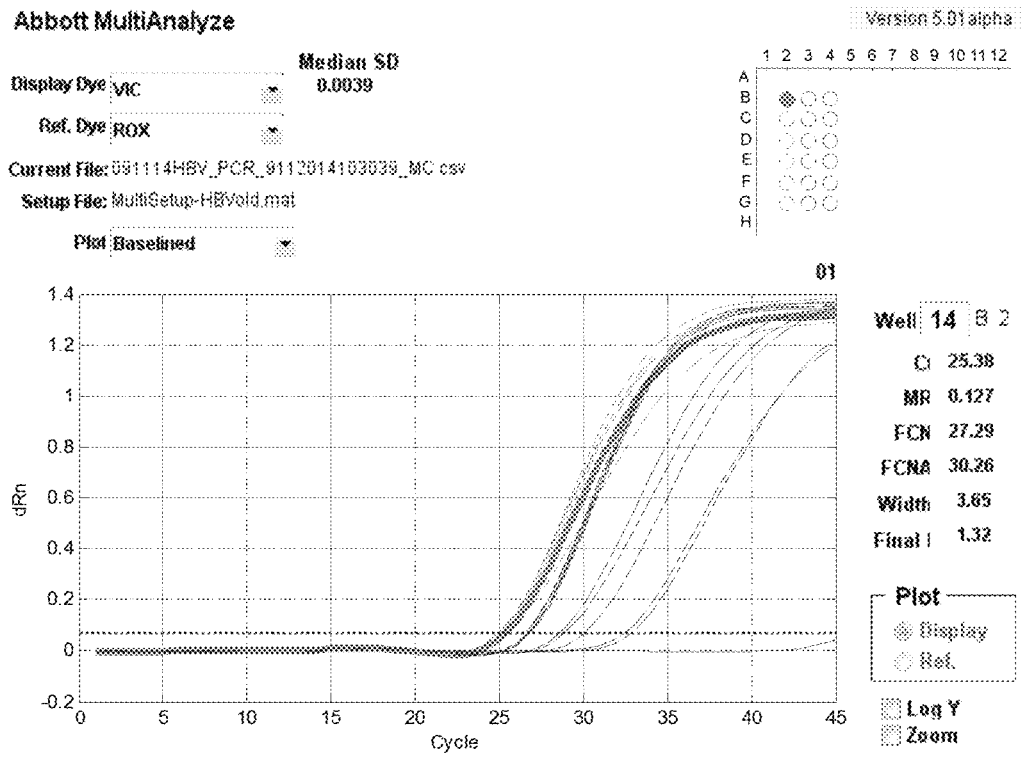
Figure 19A:
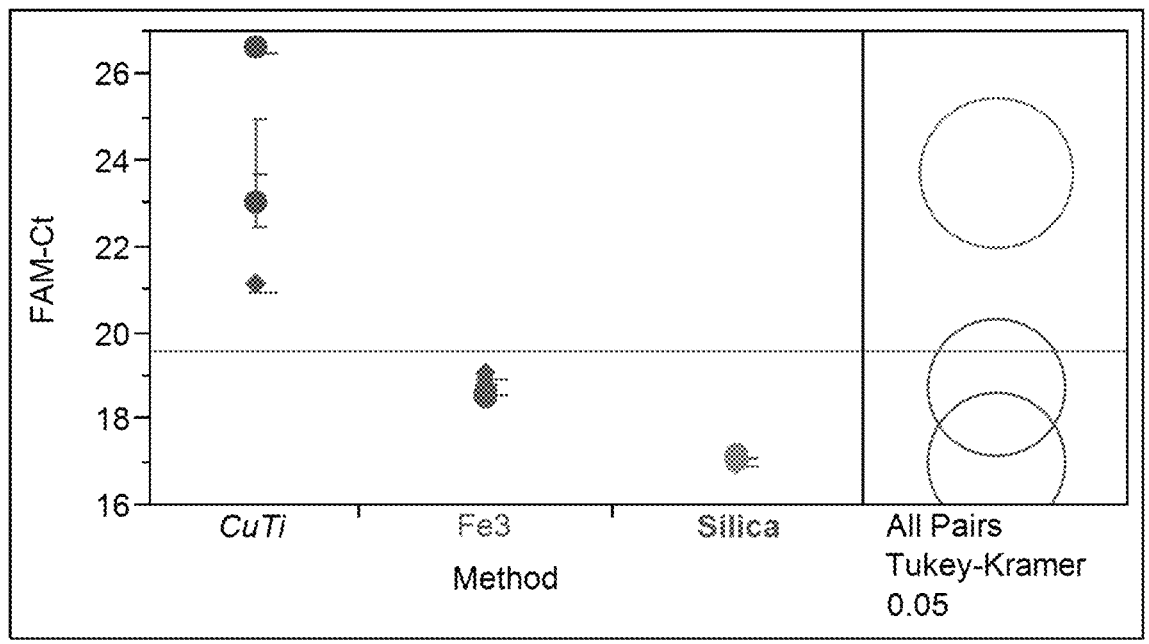
FIG. 19A-D shows a comparison of the binding of RNA and DNA to CuTi coated particles, FeO$_3$ particles, and silica particles.
Figure 19B:
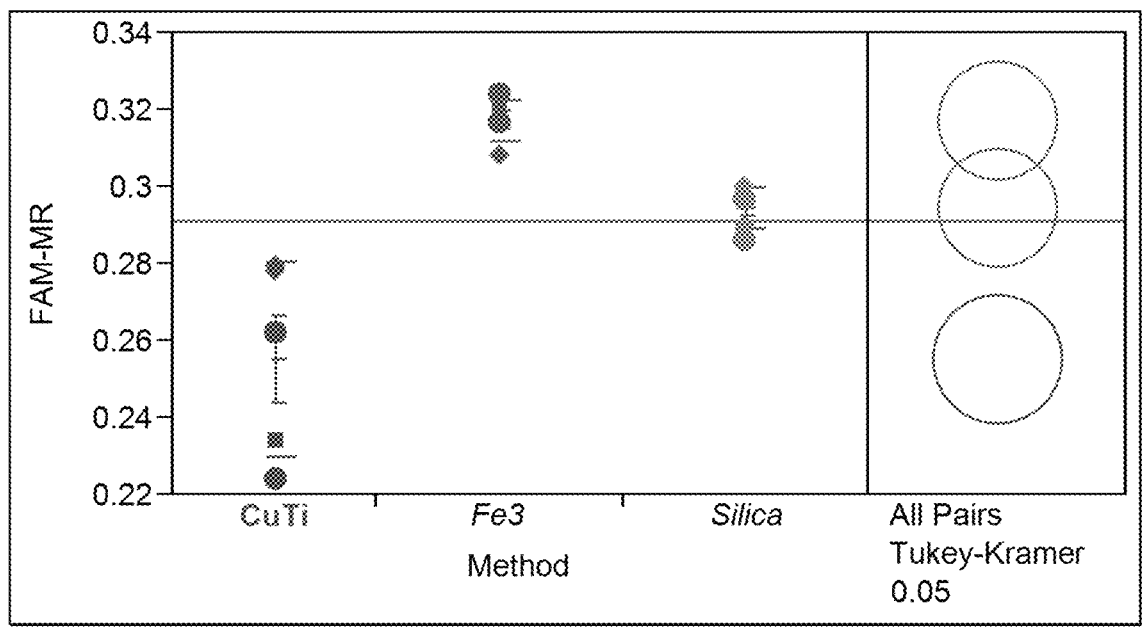
Figure 19C:
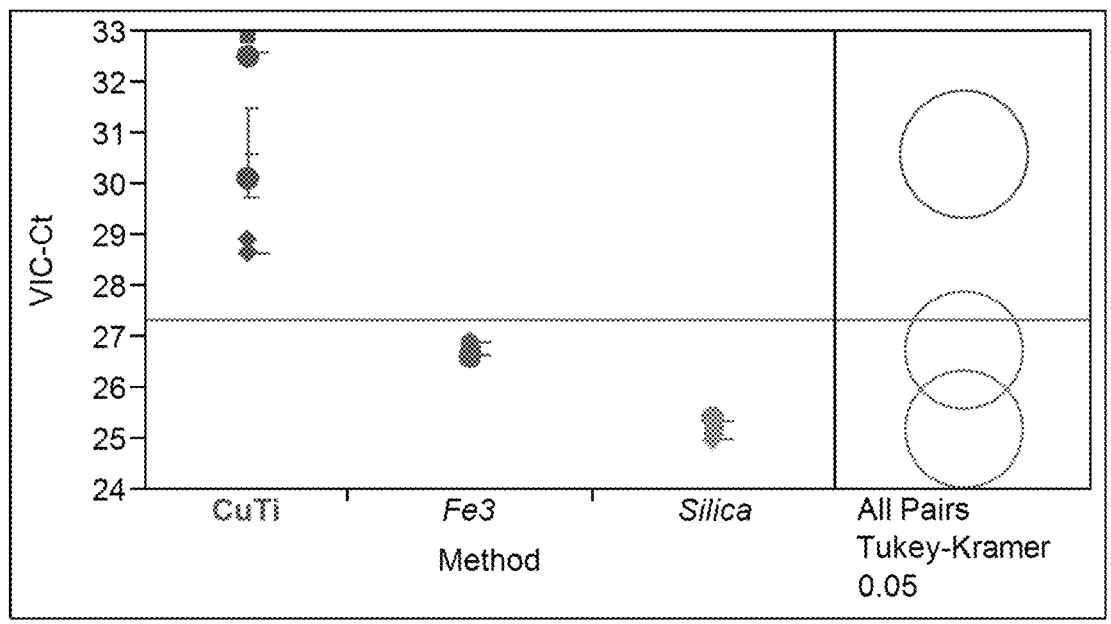
Figure 19D:
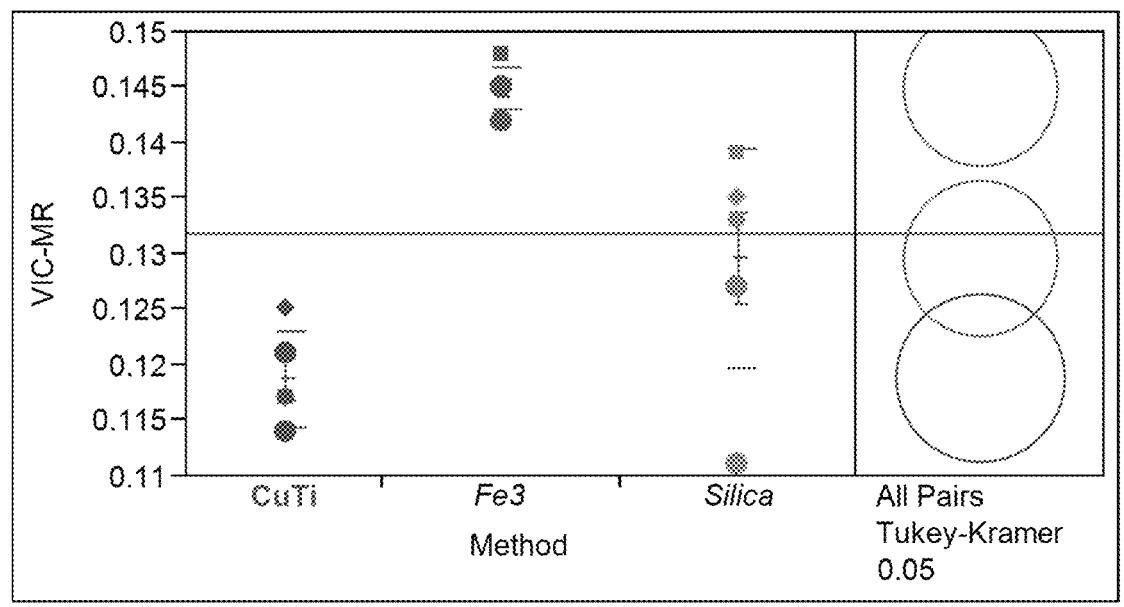

After amplification, data was analyzed using MultiAnalyze (FIG. 18A-B) and JMP for analysis. Oneway analysis of FAM-Ct by method, oneway analysis of FAM-MR by method, oneway analysis of VIC-Ct by method, and oneway analysis of VIC-MR by method is shown in FIGS. 19A-D.

Results show that the HBV DNA from the CuTi particles has a CT value that is almost 7 CTs higher than the silica method. This represents approximately a 100 fold difference (=2^6.7). Each CT represents a 2 fold difference.

The $Fe_2O_3$ method has a 1.7 CT difference which represents over a 3 fold difference. The $Fe_2O_3$ captures 33% of the DNA compared to the Silica method and the CuTi captures 1% of the HBV DNA.

For the internal control, the CuTi method has a CT value that is 5.5 CT higher than the silica method. This represents approximately a 50 fold difference (=2^5.5). Again, one sample had no reading and essentially no recovery, so the recovery is even less than 2%.

The $Fe_2O_3$ method has a 1.5 CT difference which again represents over a 3 fold difference. The $Fe_2O_3$ captures 33% of the DNA compared to the Silica method and the CuTi captures less than 2% of the internal control DNA.

The extractions were repeated as above except that an HCV sample was processed at 100 IU/ml along with a standard amount of HCV internal control.

HCV AT was diluted to first to 1000 IU/ml and then to 100 IU/ml using negative diluent. Setup was as above except that 17.1 µl of HCV internal control was added to each lyis chamber.

Figure 20A:
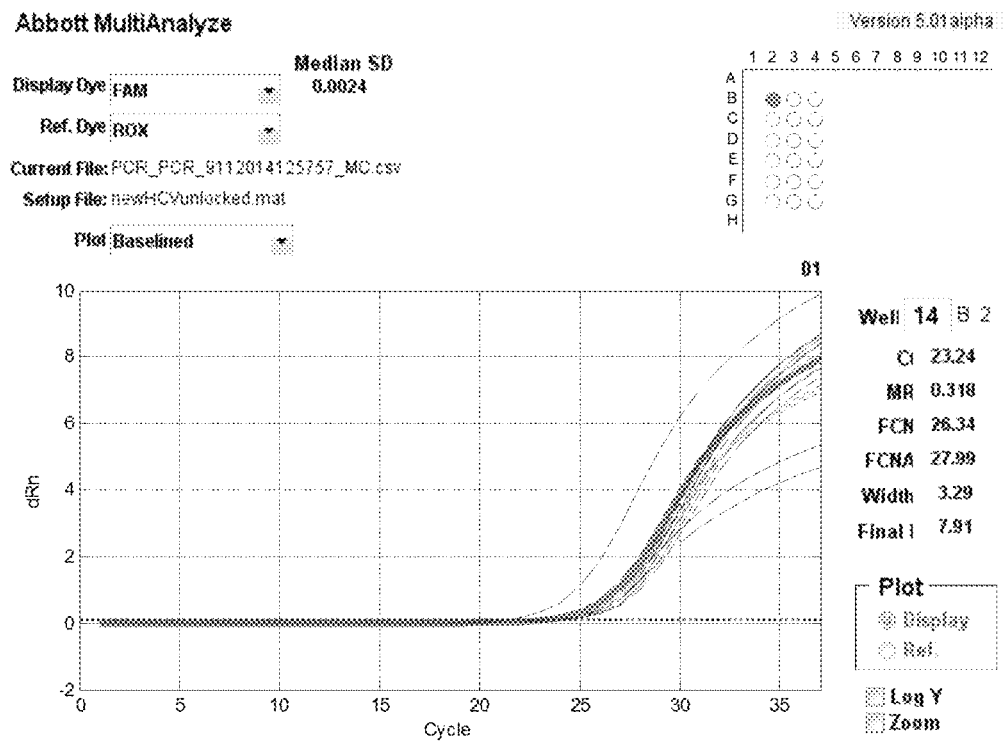
FIG. 20A-B shows the binding of RNA to CuTi coated particles.
Figure 20B:
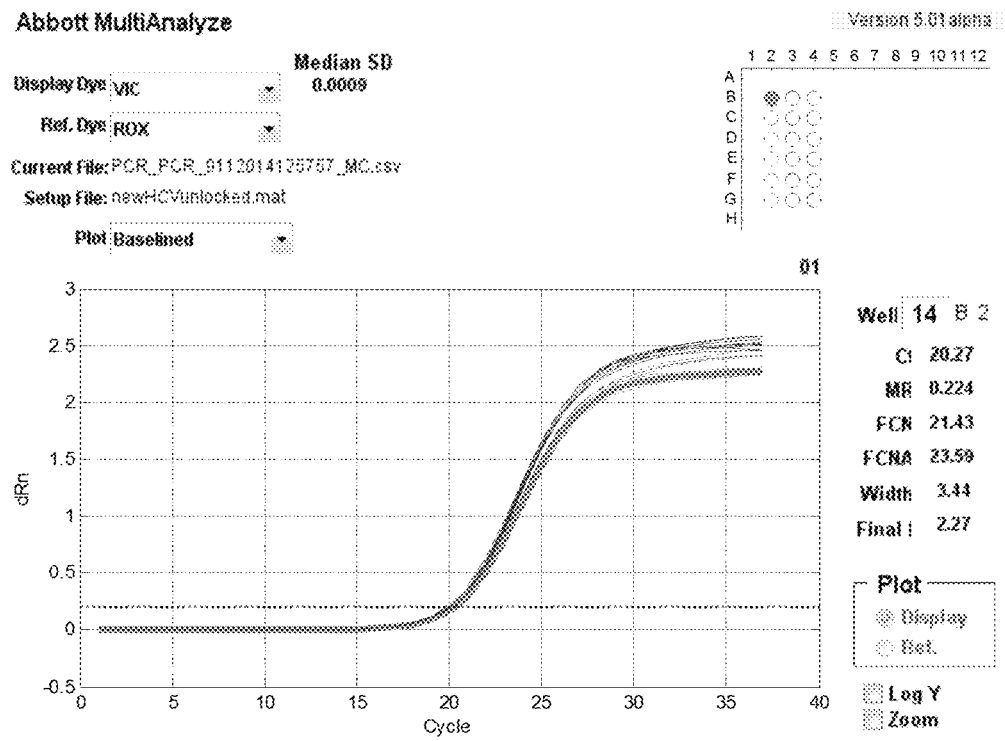
Figure 21A:
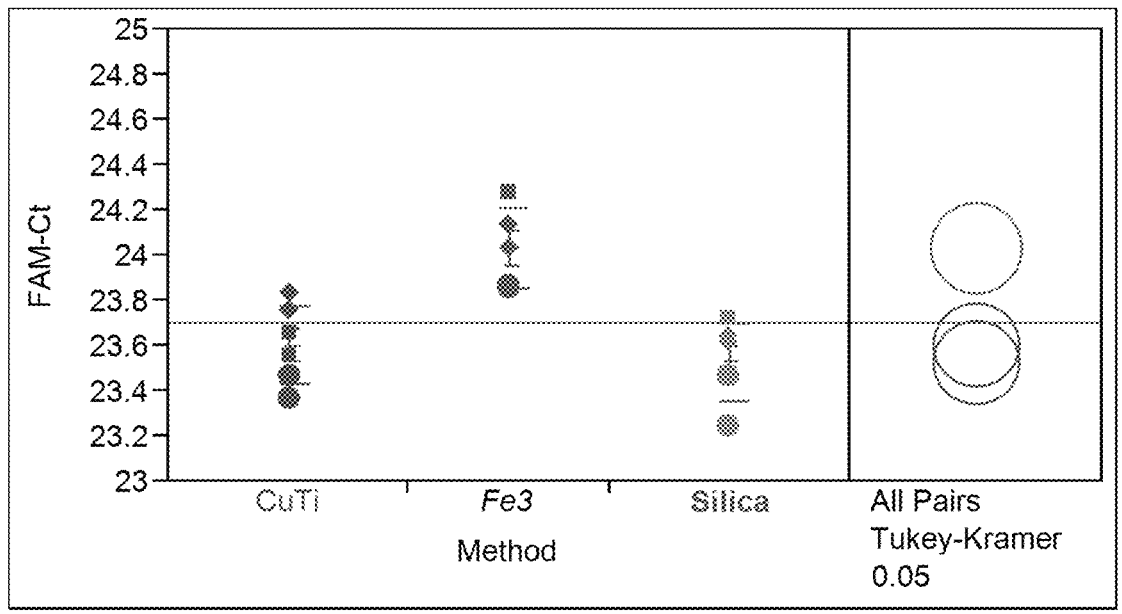
FIG. 21A-D shows a comparison of the binding of RNA and viral DNA to CuTi coated particles, FeO$_3$ particles, and silica particles.
Figure 21B:
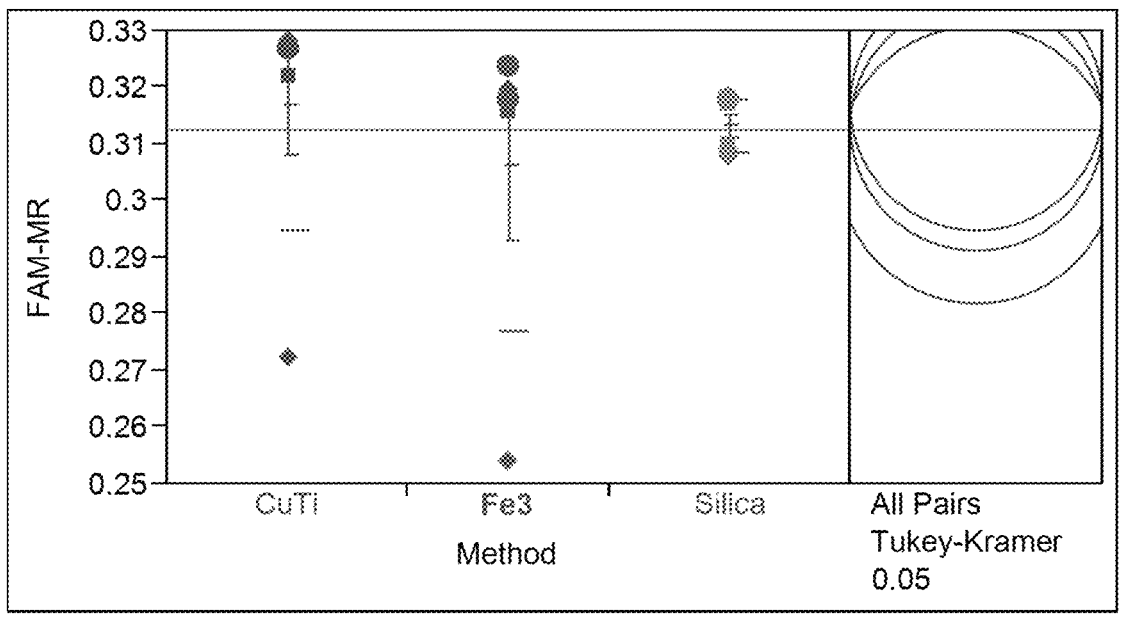
Figure 21C:
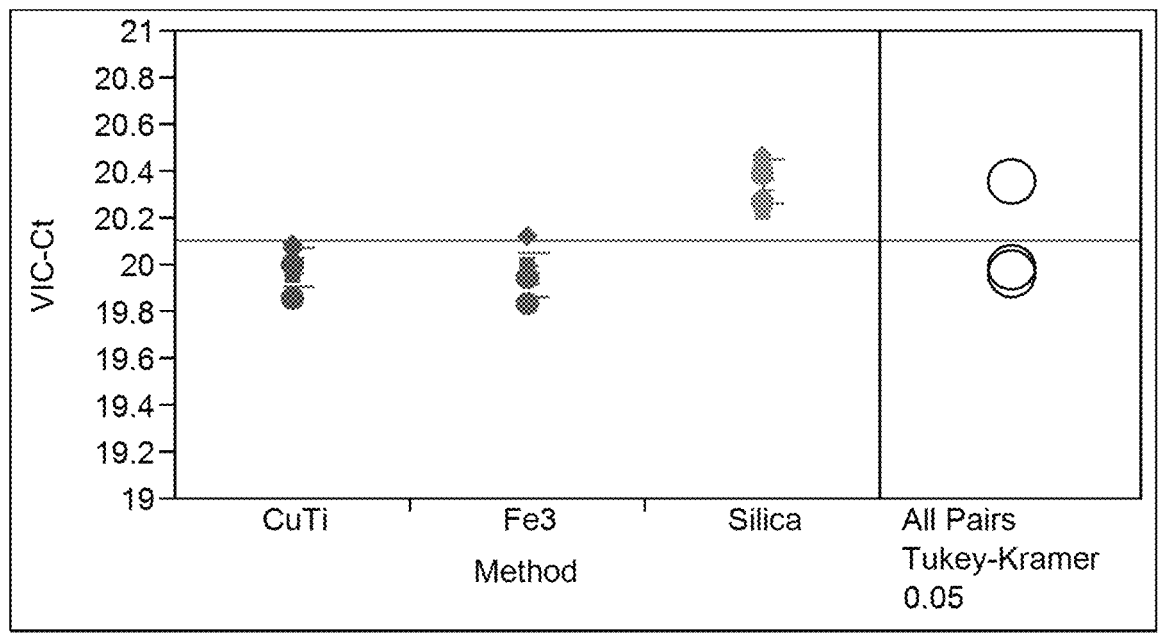
Figure 21D:
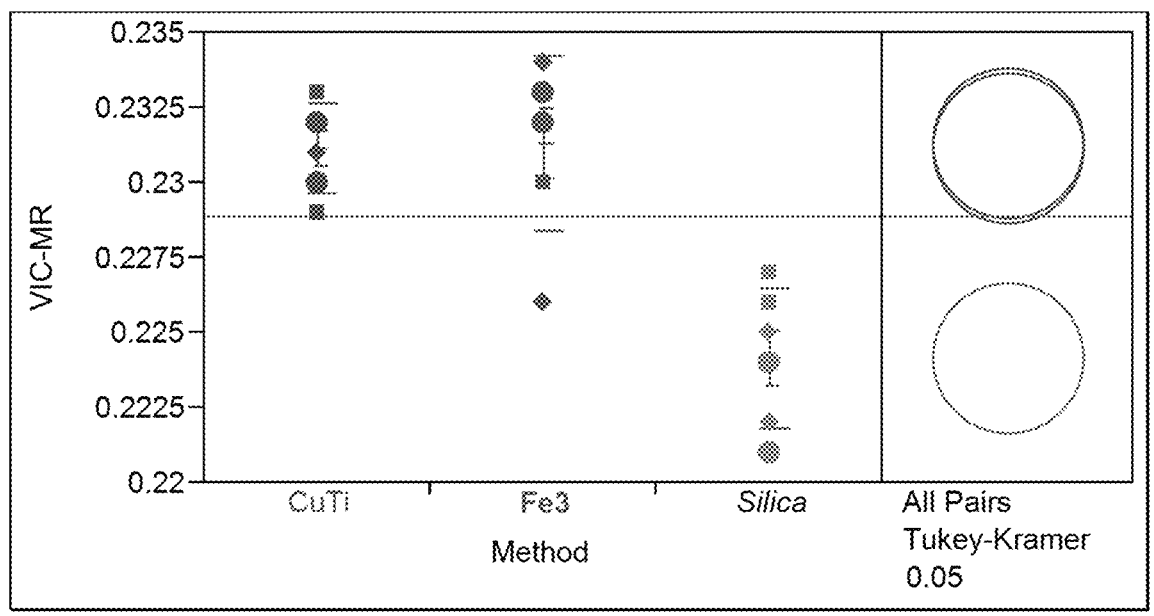

Results of FAM analysis are shown in FIGS. 20A-B. Oneway Analysis of FAM-Ct by method, oneway analysis of FAM-MR by method, oneway analysis of VIC-Ct by method, and oneway analysis of VIC-MR by method is shown in FIGS. 21A-D.

For the HCV FAM signal, the CuTi particles and the silica particles had essentially identical CT and MR values. The $Fe_2O_3$ particles had a CT value just slightly above the other conditions that would be 40% less than the other signals. The MR values are not significantly different for all three conditions.

For the Internal control signal, the CuTi particles and the $Fe_2O_3$ particles matched CT values and the silica particles had a slightly elevated CT value which would be less than a 30% difference.

The CuTI particles demonstrate RNA recovery at least as good as the $Fe_2O_3$ and the silica particles for both HCV RNA and the internal control RNA (pumpkin).

Overall Summary:

The CuTi particles capture RNA as well as other methods but do not capture DNA as well as the other methods. This means that the CuTi particles can selectively capture RNA. This is important in the measure method of RNA viruses. It is not desirable to capture DNA because the presence of pro-viral DNA in the extraction could give an inaccurate determination of the amount of viral particles.

Figure 22:
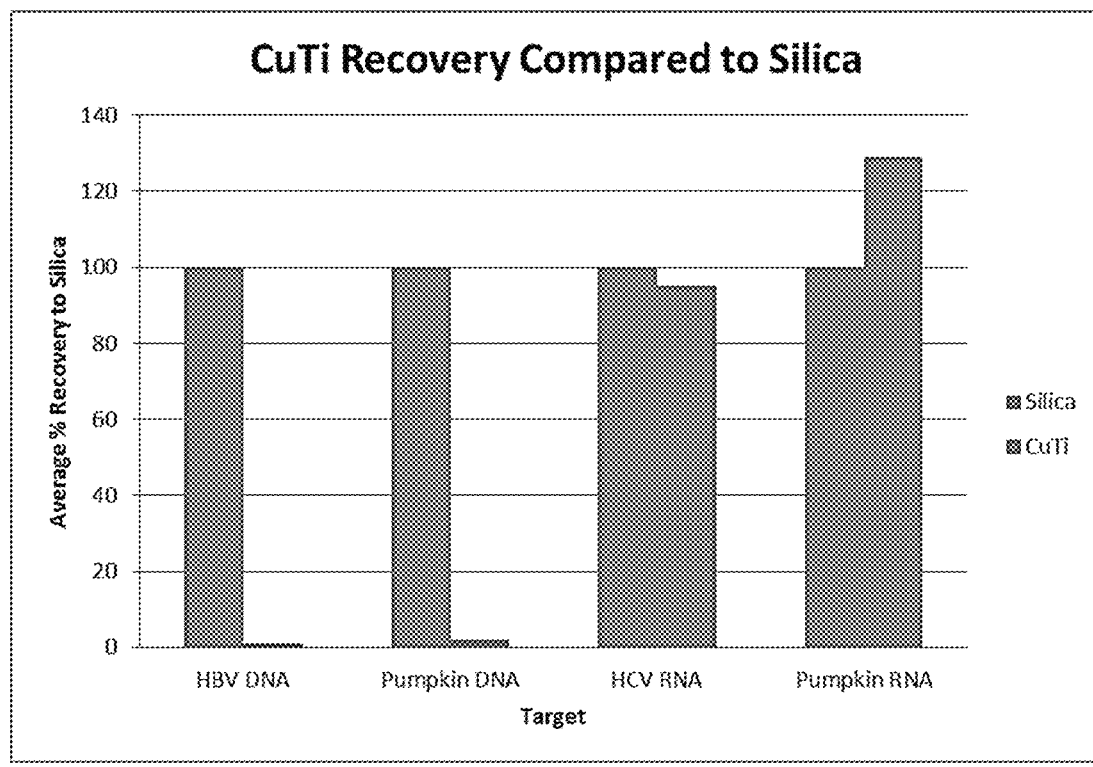
FIG. 22 shows recovery of RNA and DNA from CuTi coated particles compared to silica particles.

FIG. 22 and the Table below shows CuTi recovery compared to silica.

| Target | % Recovery | |
|---|---|---|
| | Silica | CuTi |
| HBV DNA | 100 | 1 |
| Pumpkin DNA | 100 | 2 |
| HCV RNA | 100 | 95 |
| Pumpkin RNA | 100 | 129 |

Example 7

This example describes analysis of how well the CuTi particles bind genomic DNA. Genomic DNA, HBV DNA and HCV RNA were used as the targets. Results were compared with the iron oxide and total nucleic acid method (silica particles).

Some samples were re-eluted to test a heated wash step. Samples were eluted with water (heated wash simulation) and then eluted with phosphate for the $Fe_2O_3$ and CuTi method. No $2^{nd}$ elution was performed for the TNA-Silica method.

Targets were made using HBV CalB, HCV CalB, and genomic DNA. The first extraction was CuTi particles, the elution tubes were removed and replaced with blanks), the particles were manually captured and returned to the automated sample preparation instrument. The second elution was performed and particles were resuspended particles by pipetting. They were placed back in the heater block, incubated 10 minutes and then particles were manually captured. All extraction were done with 176 μl elution and run with the 3 assays, HCV, HBV, and MYD88 genomic DNA.

Extraction from $Fe_2O_3$ particles was performed as above except that the elution is a two stage elution with 50 μl 20 mM phosphate followed by 126 μl water.

Silica TNA extraction was performed using a single stage 176 μl water elution. No second elution was performed.

Figure 23A:
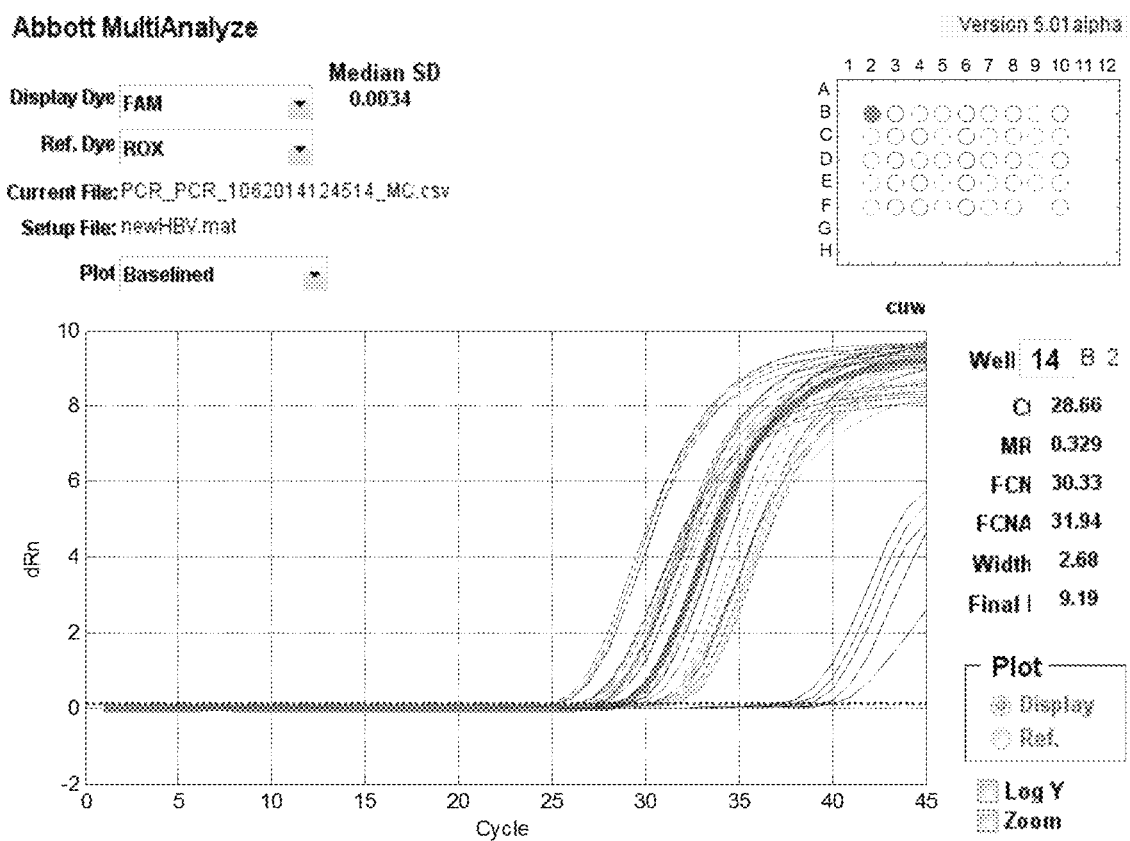
FIG. 23A-B shows the binding of RNA to CuTi coated particles.
Figure 23B:
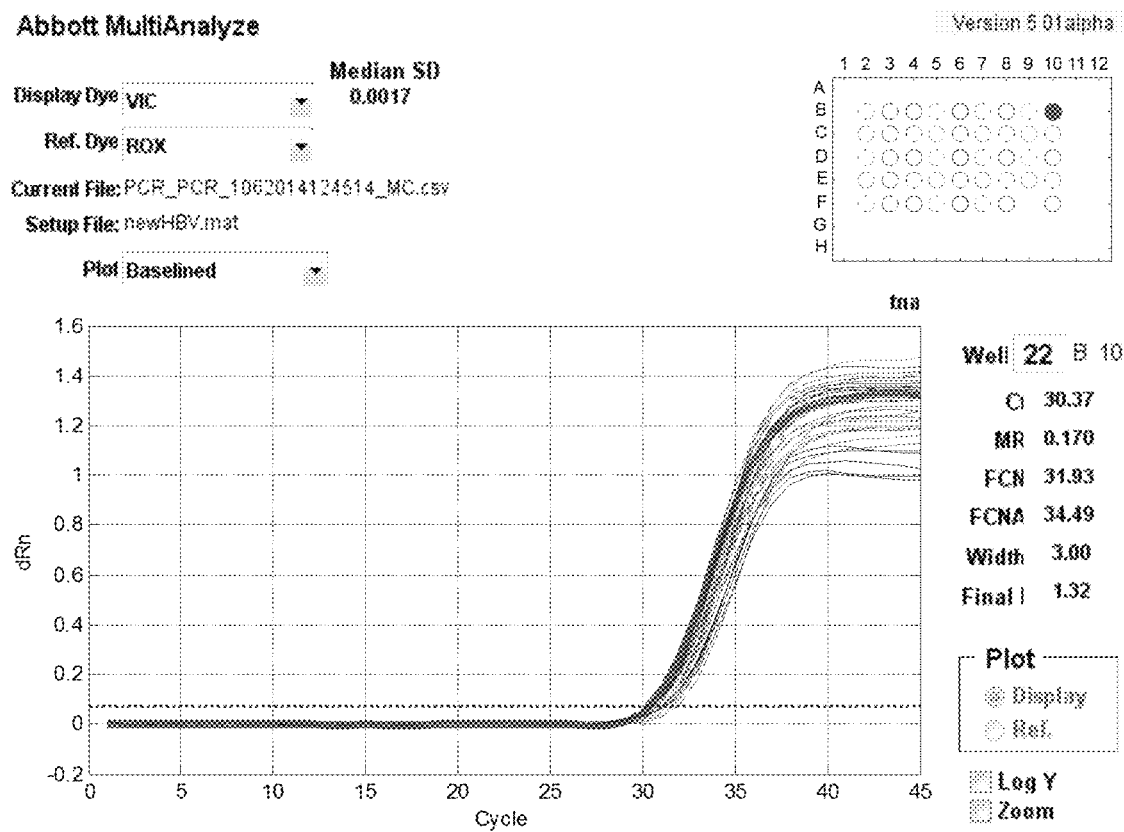
Figure 24A:
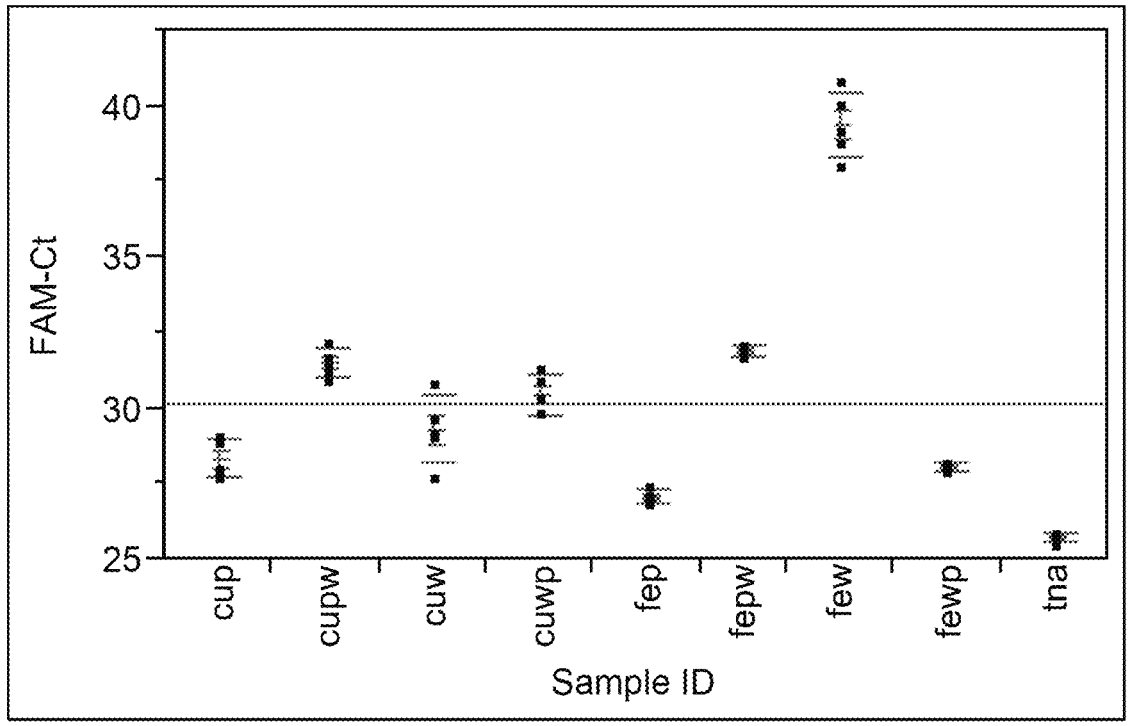
FIG. 24A-B shows a comparison of the binding of RNA and genomic DNA from CuTi coated particles, FeO$_3$ particles, and silica particles.
Figure 24B:
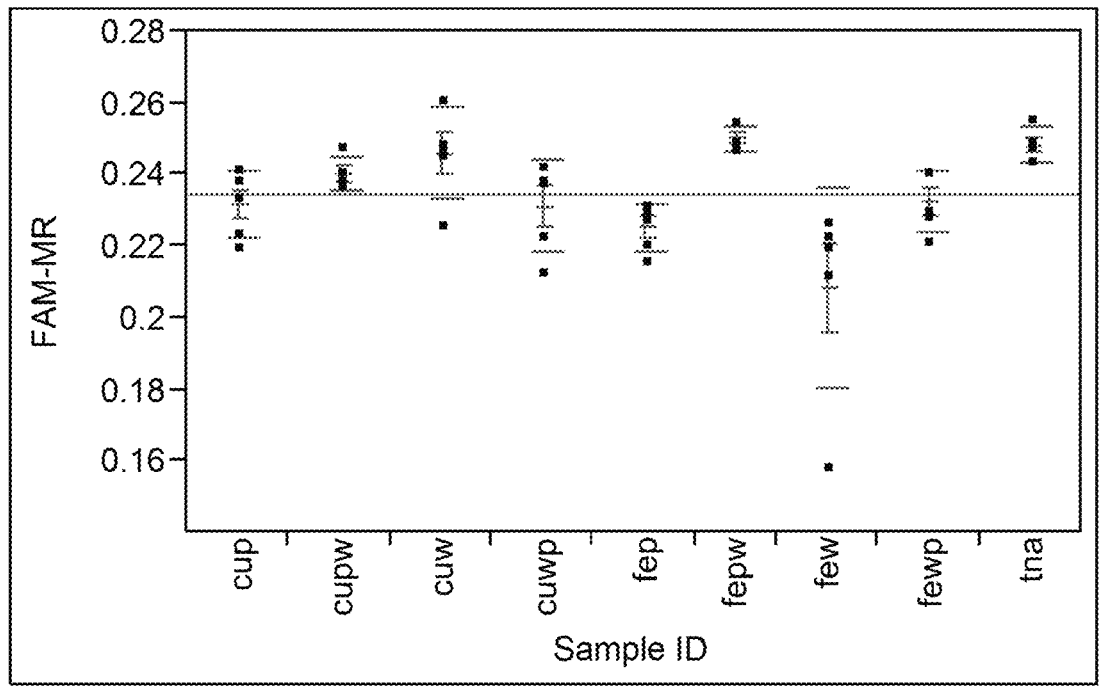

After amplification, HBV data was analyzed using MultiAnalyze (FIGS. 23A-B) and JMP. Oneway Analysis of FAM-Ct by Sample ID, and oneway analysis of FAM-MR by Sample ID is shown in FIGS. 24A-B.

The Washing steps did not improve any of the HBV signals.

Figure 25:
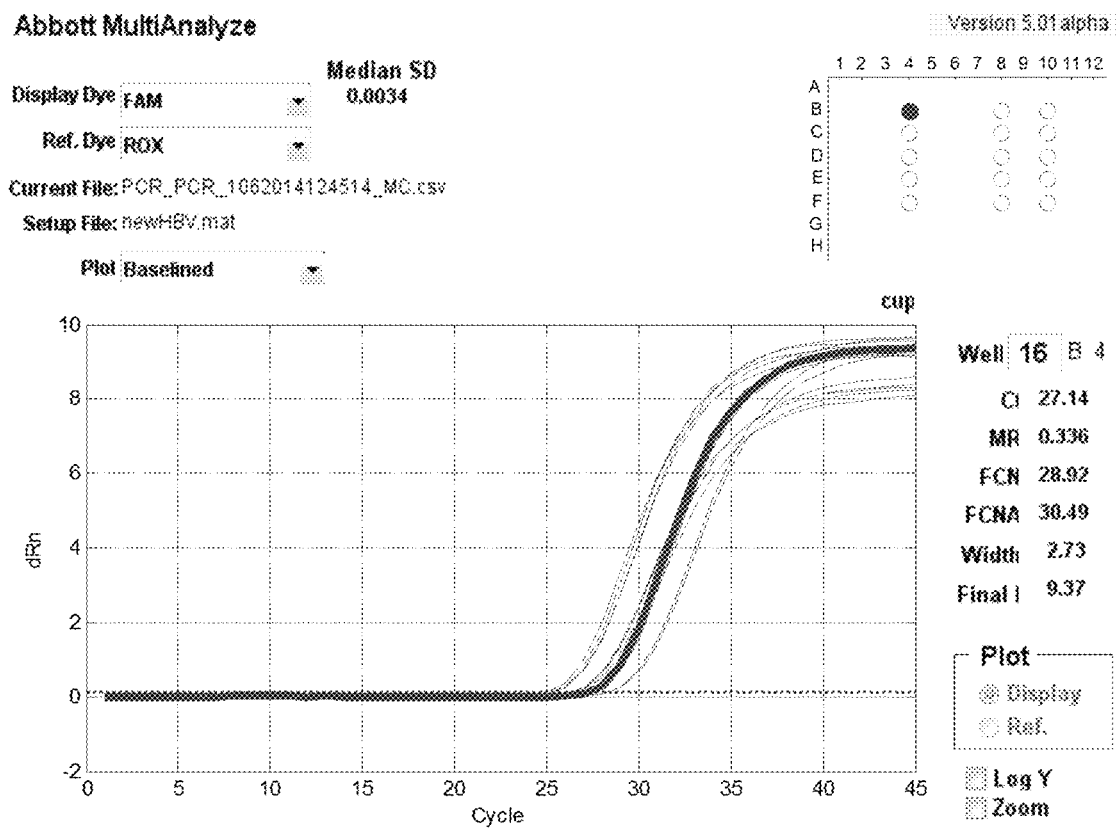
FIG. 25 shows recovery of RNA and DNA from CuTi coated particles compared to silica particles.
Figure 26A:
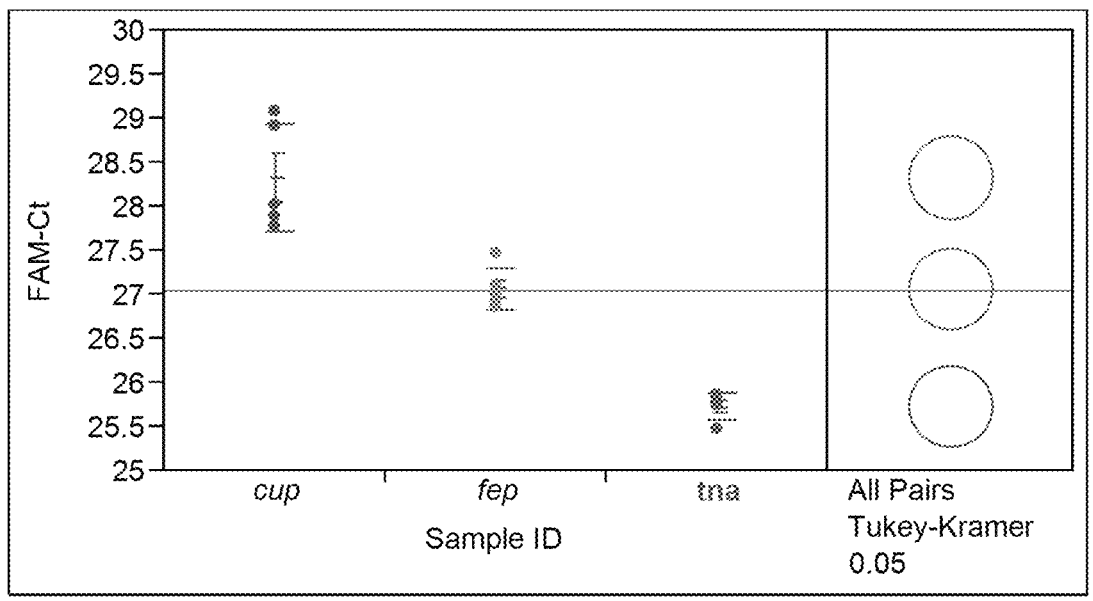
FIG. 26A-B shows a comparison of the elution of RNA and DNA from CuTi coated particles, FeO$_3$ particles, and silica particles.
Figure 26B:
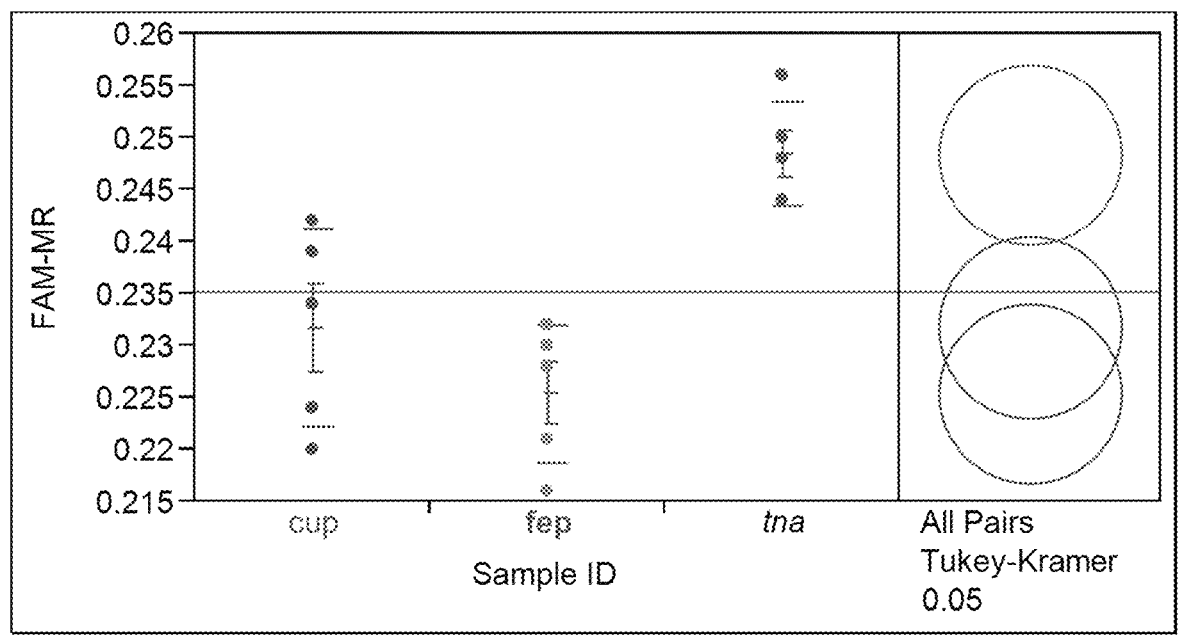

Next, the first phosphate elutions were compared with the silica process. (FIG. 25). Oneway analysis of FAM-Ct by sample ID and oneway analysis of FAM-MR by Sample ID is shown in FIGS. 26A-B.

The $Fe_2O_3$ process and the CuTi process do not isolate DNA as well as the TNA method (see Table below).

| HBV | FAM CT | CT diff | xfold | % TNA |
|---|---|---|---|---|
| CuTi | 28.33 | 2.6 | 6.062866 | 16% |
| $Fe_2O_3$ | 27.07 | 1.34 | 2.531513 | 40% |
| Silica | 25.73 | | | |

The $Fe_2O_3$ method isolated 40% of the HBV signal when processed with genomic DNA. The CuTi method only isolated 16% DNA compared to the silica particle TNA method.

Figure 27:
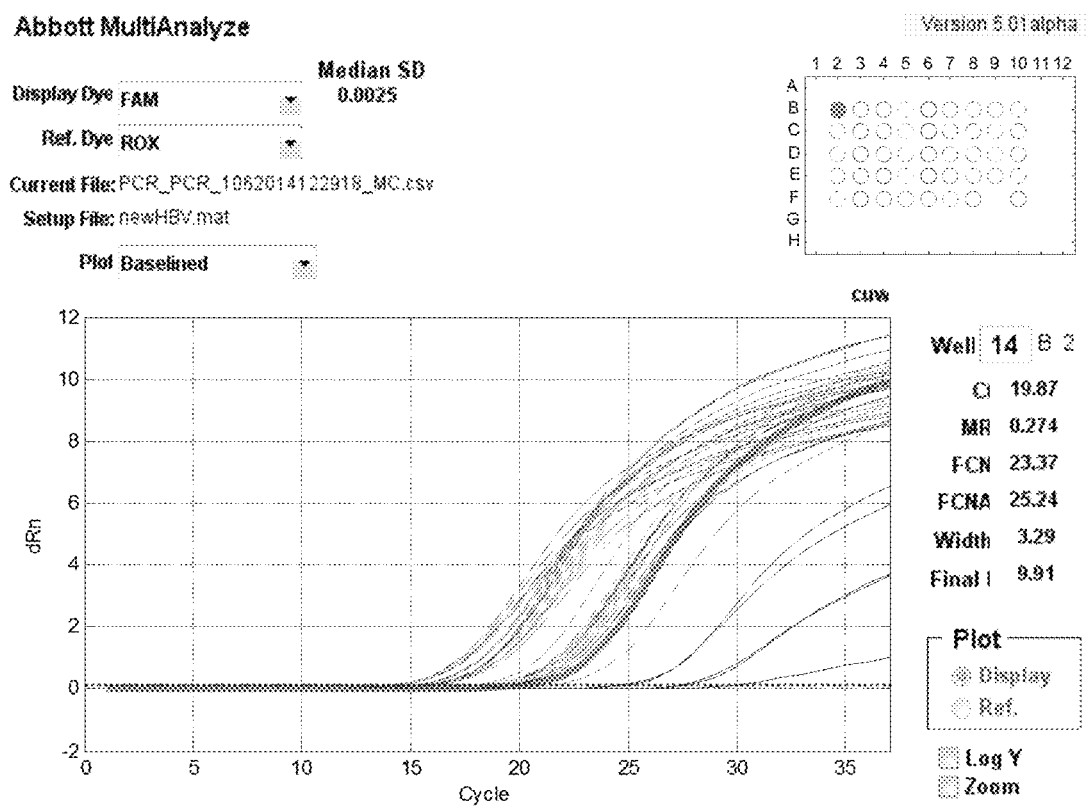
FIG. 27 shows the binding of RNA to CuTi coated particles.
Figure 28A:
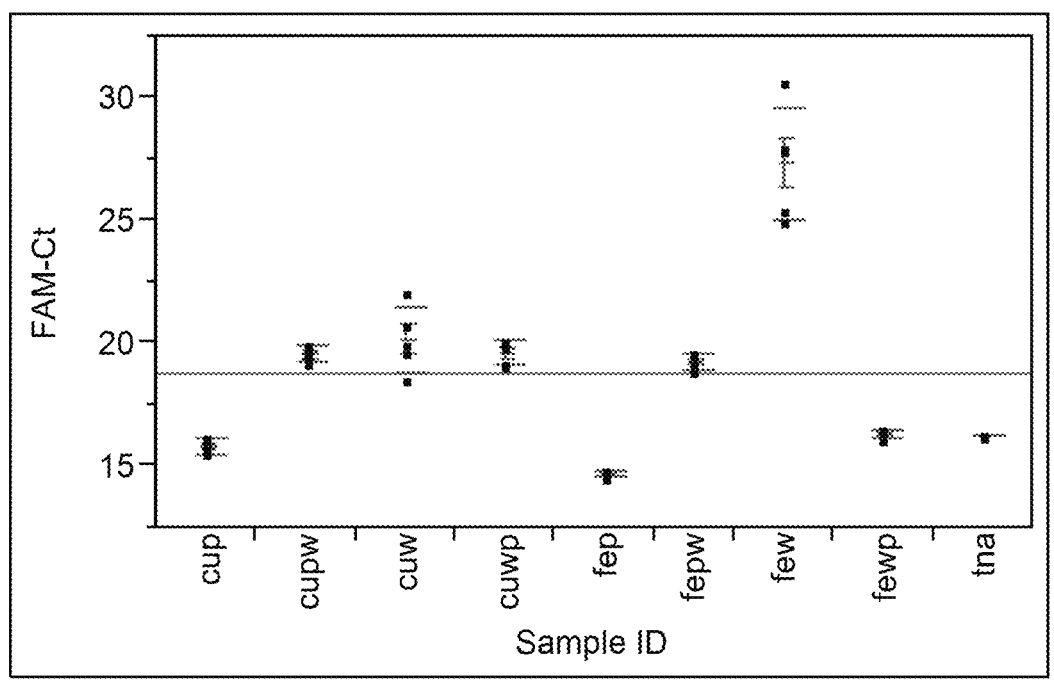
FIG. 28A-B shows a comparison of the elution of RNA and DNA from CuTi coated particles, FeO$_3$ particles, and silica particles.
Figure 28B:
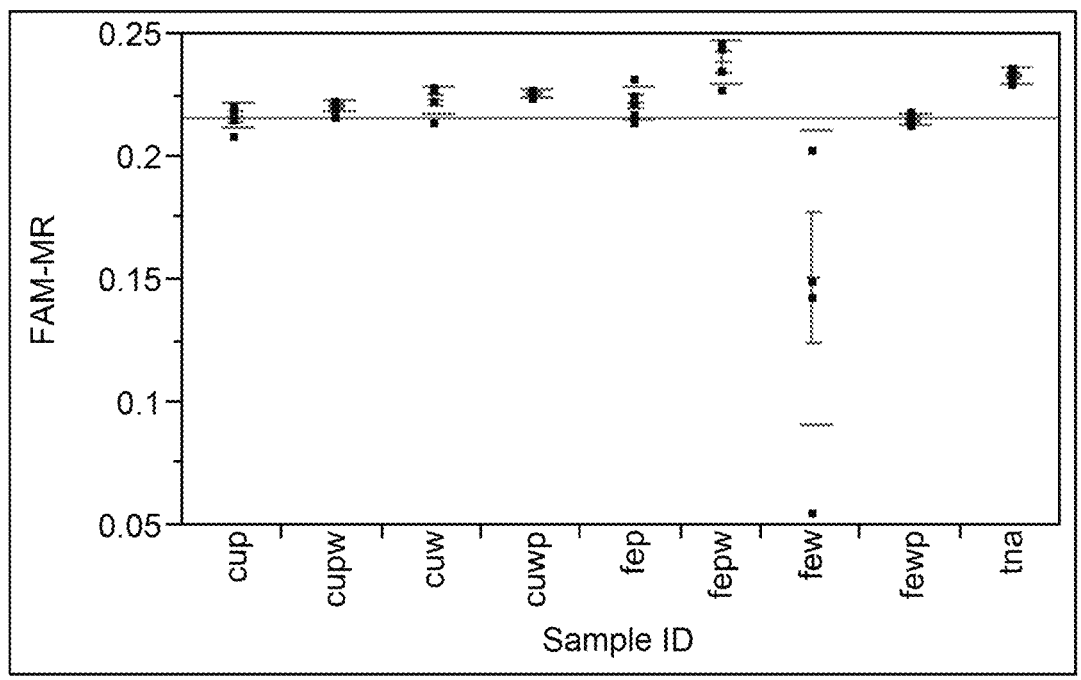

The assay and analysis was repeated with HCV. FIG. 27 shows FAM results for HCV. Oneway analysis of FAM-Ct by Sample ID and oneway Analysis of FAM-MR by Sample ID is shown in FIGS. 29A-B. The Washing steps did not improve any of the HBV signals.

Figure 29:
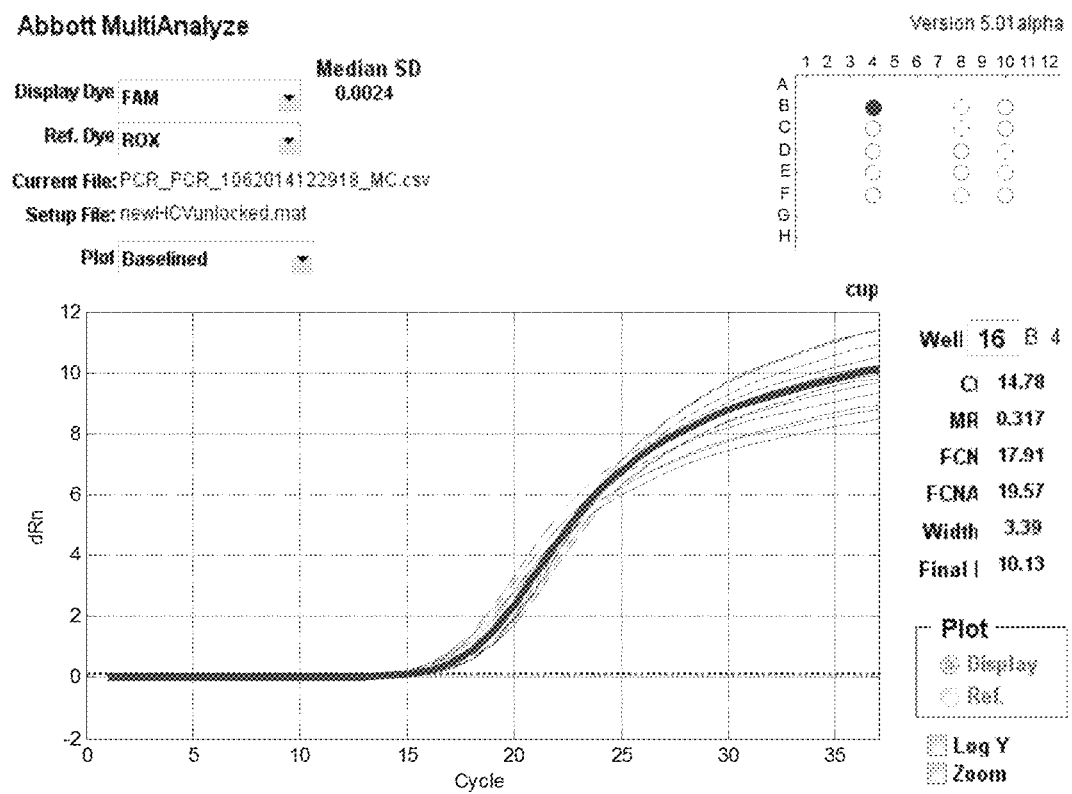
FIG. 29 shows a comparison of the elution of RNA and DNA from CuTi coated particles, FeO$_3$ particles, and silica particles.
Figure 30A:
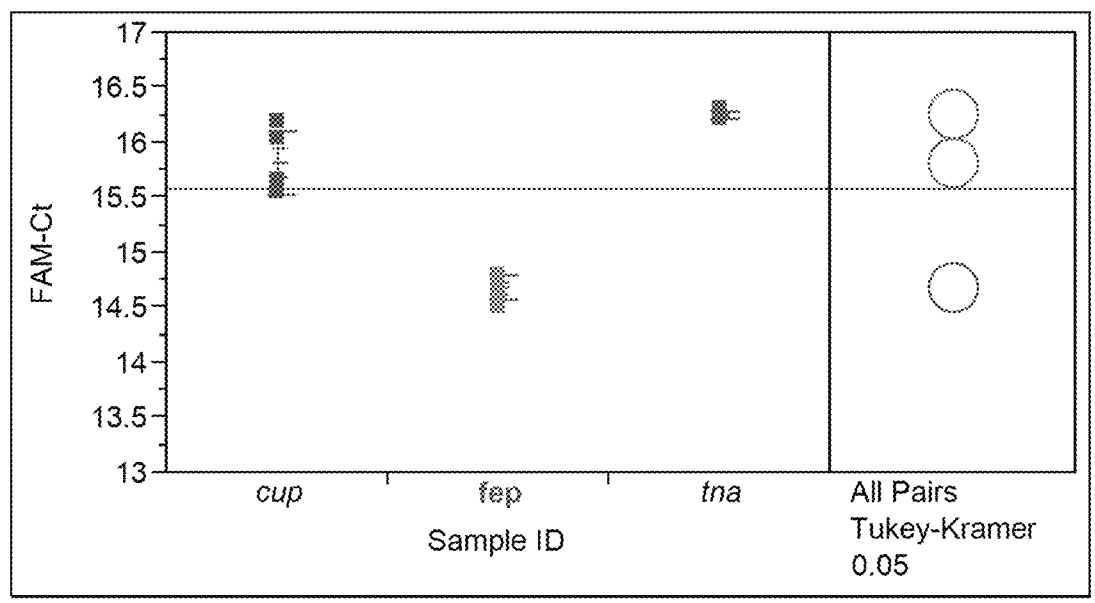
FIG. 30A-B shows a comparison of the elution of RNA and DNA from CuTi coated particles, FeO$_3$ particles, and silica particles.
Figure 30B:
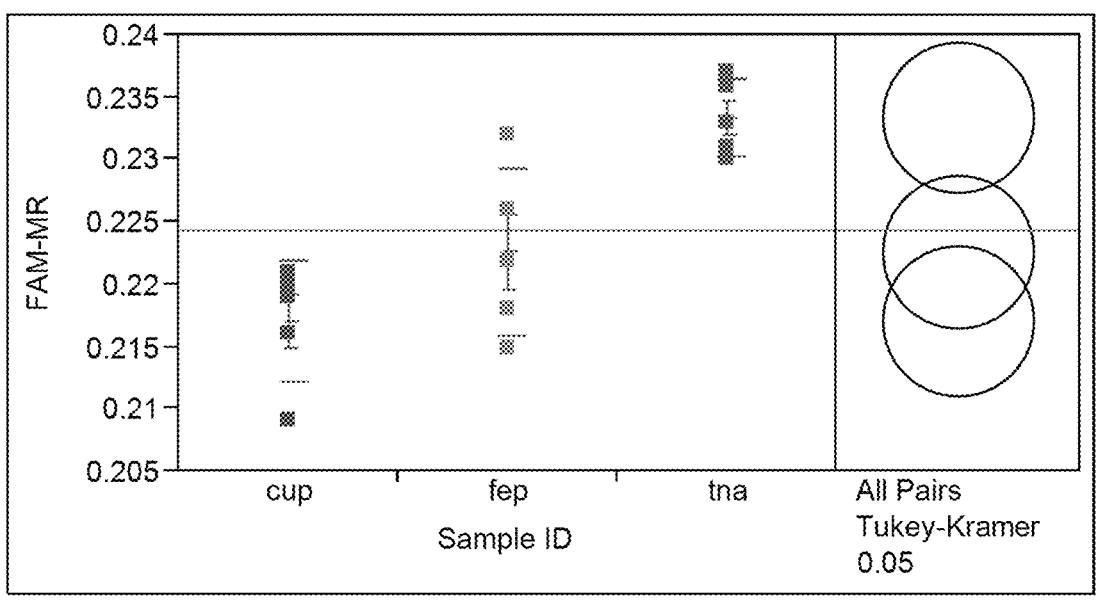

The first phosphate elutions were compared with the silica process. (FIG. 29). Oneway analysis of FAM-Ct by Sample ID and oneway analysis of FAM-MR by Sample ID is shown in FIGS. 30A-B. Results show that the $Fe_2O_3$ method isolated more HCV RNA than either the CuTi method or the silica method in this experiment. The CuTi method isolated more RNA than the silica TNA method. All three methods effectively isolate RNA.

Figure 31:
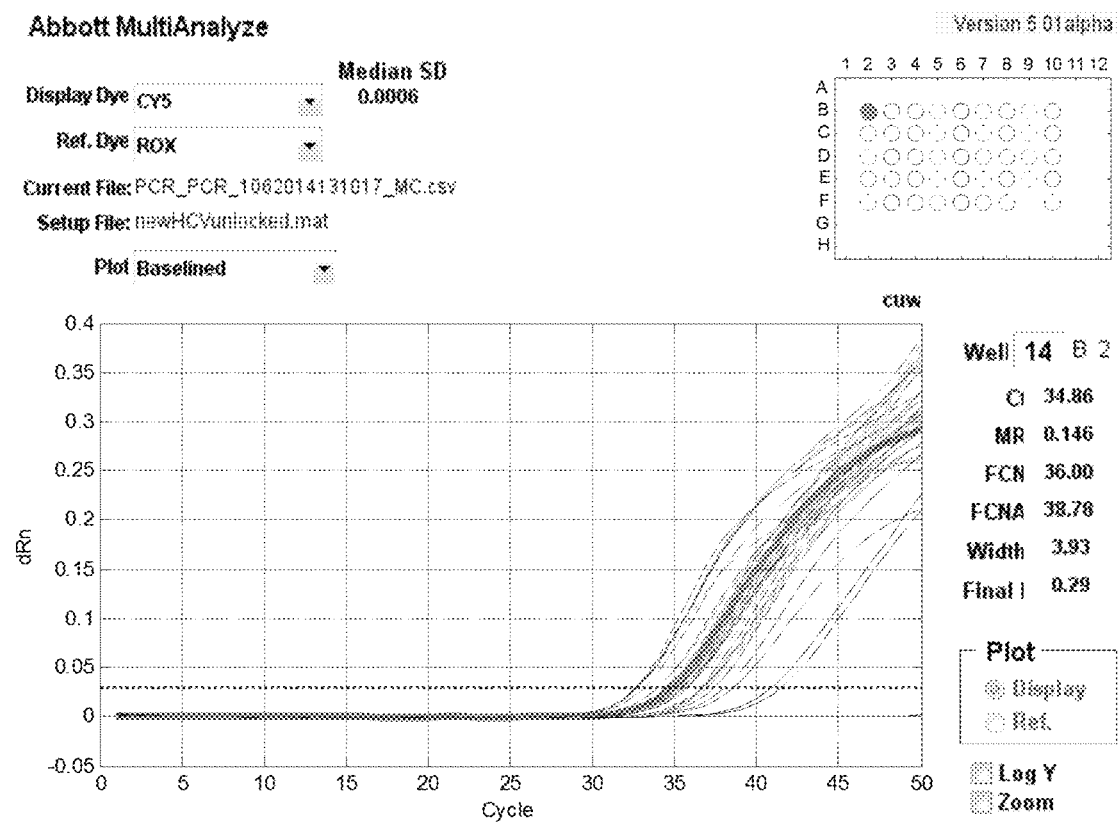
FIG. 31 shows a comparison of the elution of RNA and DNA from CuTi coated particles, FeO$_3$ particles, and silica particles.
Figure 32A:
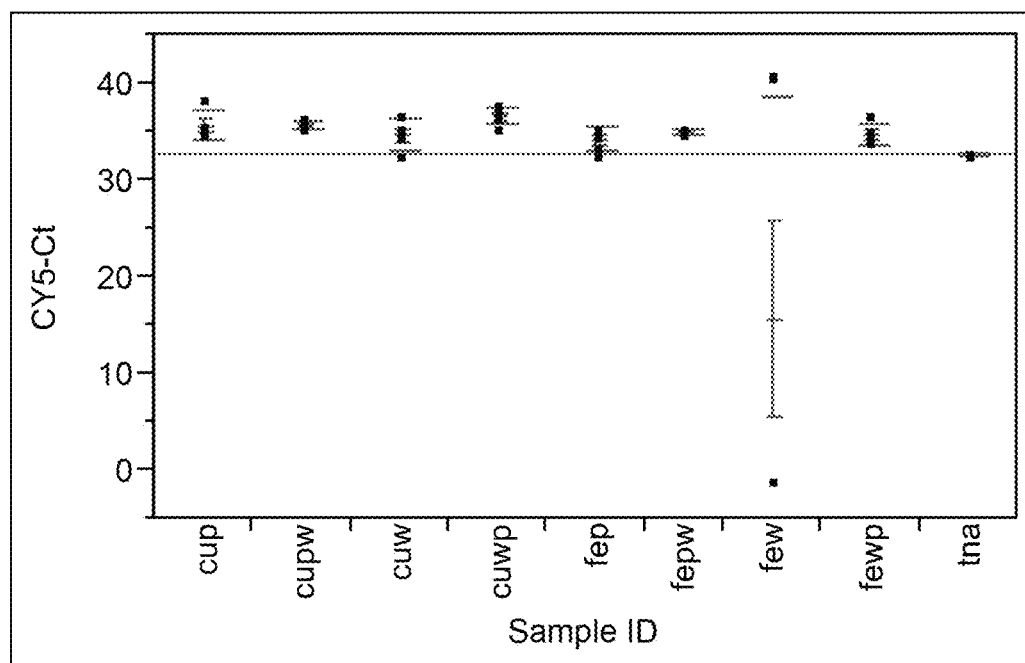
FIG. 32A-B shows a comparison of the elution of RNA and DNA from CuTi coated particles, FeO$_3$ particles, and silica particles.
Figure 32B:
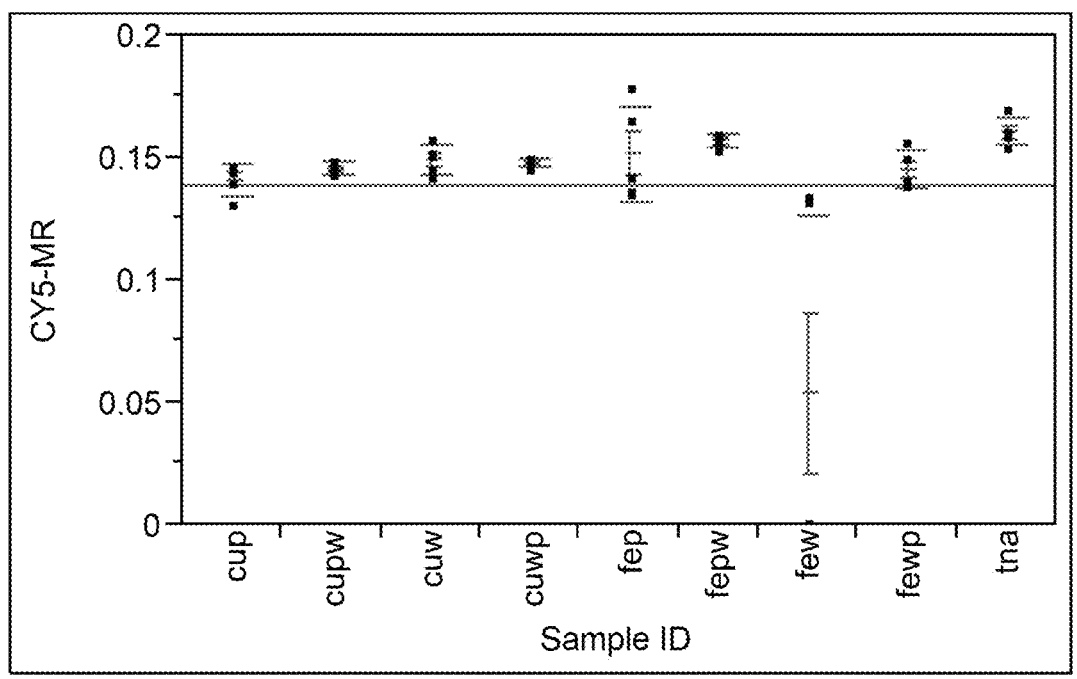

Experiments were repeated with genomic DNA. FIG. 31 shows FAM results. Oneway analysis of CY5-Ct by Sample ID and oneway analysis of CY5-MR by Sample ID is shown in FIGS. 32A-B.

Again, the Washing did not appear to improve the signals.

Figure 33:
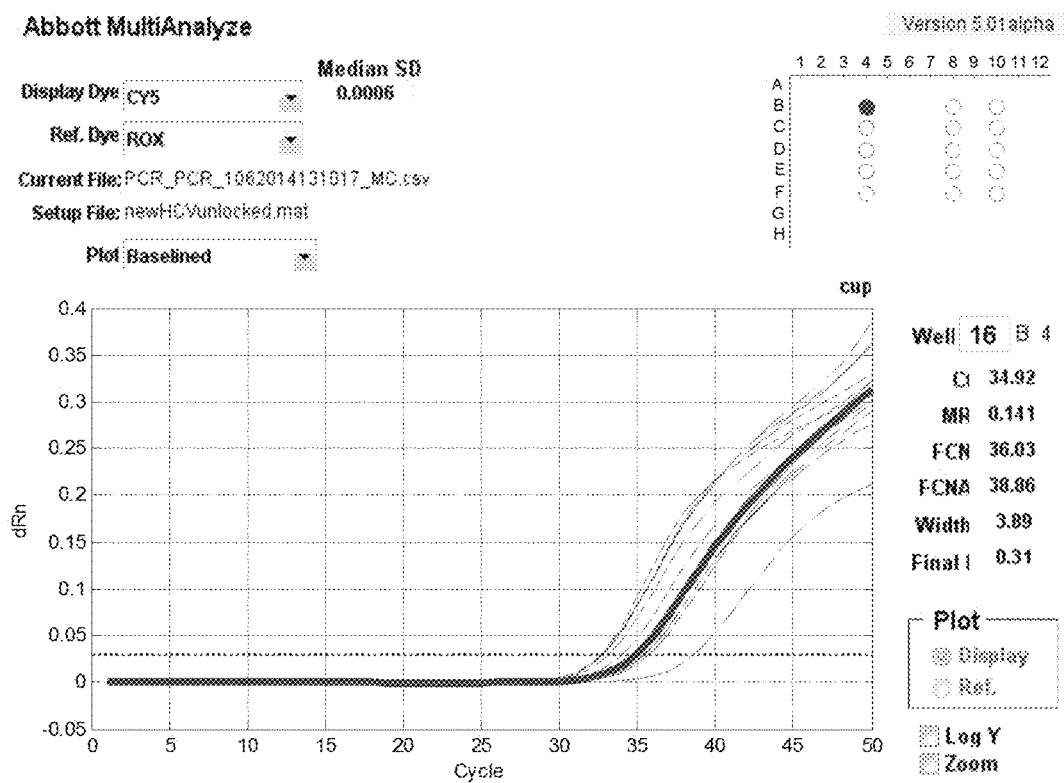
FIG. 33 shows a comparison of the elution of RNA and DNA from CuTi coated particles, FeO$_3$ particles, and silica particles.
Figure 34A:
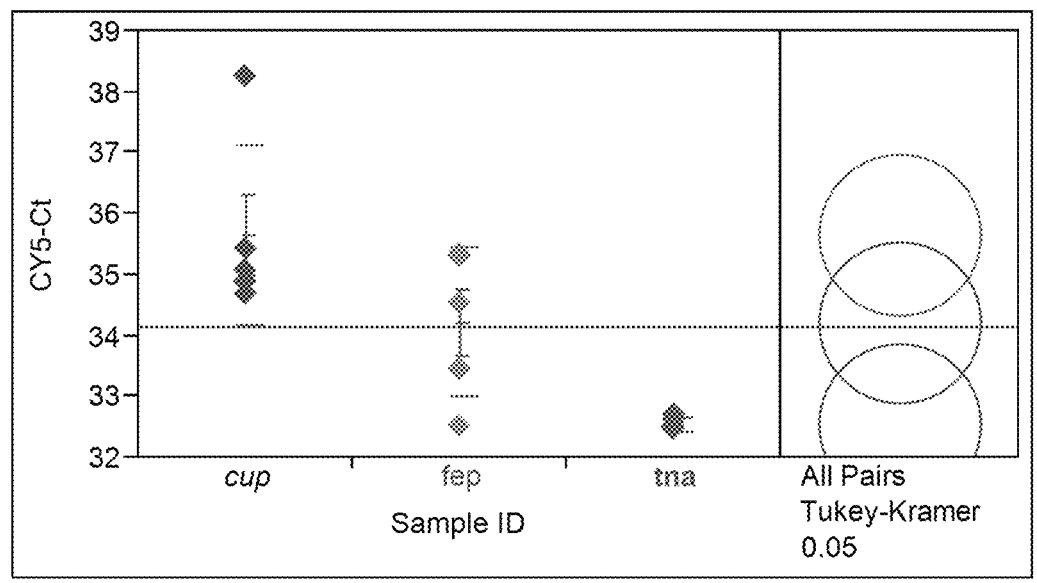
FIG. 34A-B shows a comparison of the binding and elution of RNA and DNA from CuTi coated particles, FeO$_3$ particles, and silica particles.
Figure 34B:
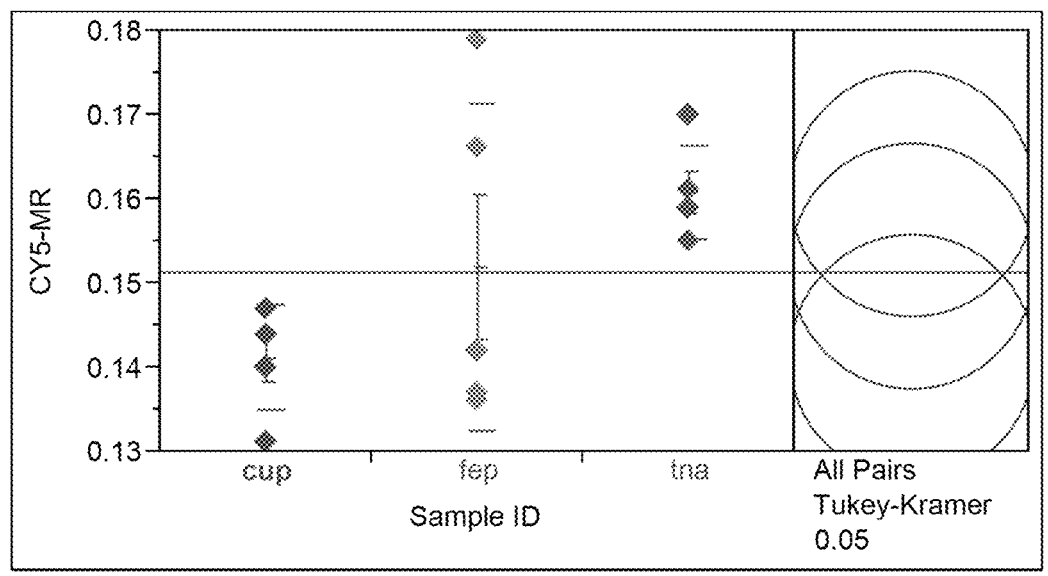

The first phosphate elutions were compared with the silica process (FIG. 33). Oneway analysis of CY5-Ct by Sample ID and oneway analysis of CY5-MR by Sample ID is shown in FIGS. 34A-B and the below Table.

| MYD88 | FAMCT | CT diff | xfold | % TNA |
|---|---|---|---|---|
| CuTi | 35.666 | 3.086 | 8.491386 | 12% |
| Fe2O3 | 34.22 | 1.64 | 3.116658 | 32% |
| Silica | 32.58 | | | |

Results show that the $Fe_2O_3$ method isolates 32% of the genomic DNA. The CuTi method only isolates 12% DNA compared to the silica particle TNA method.

Summary:

The $Fe_2O_3$ method isolates 40% of the HBV signal when processed with genomic DNA. The CuTi method only isolates 16% DNA compared to the silica particle TNA method.

Figure 35:
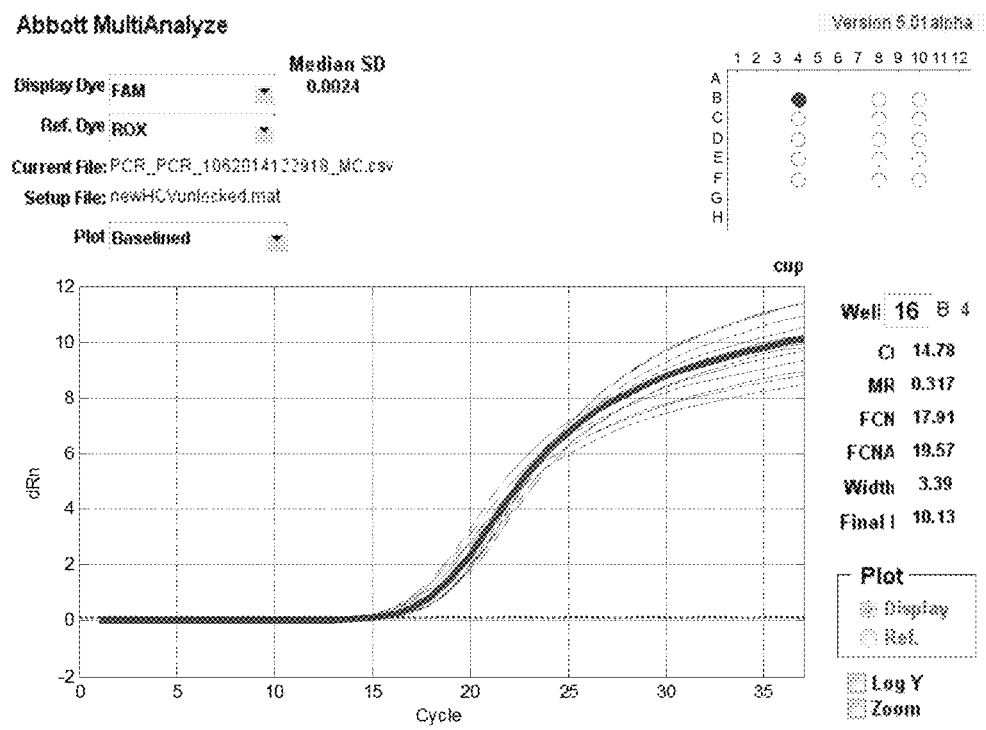
FIG. 35 shows isolation of HCV with $Fe_2O_3$, CuTi and silica.

The $Fe_2O_3$ method isolated more HCV RNA than either the CuTi method or the silica method in this experiment. The CuTi isolated more RNA than the silica TNA method, 136%. All three methods effectively isolate RNA as can be seen by the amplification curves for FAM. There is a great deal of overlap in the curves and the CT values may not reflect that similarity (FIG. 35).

The $Fe_2O_3$ method isolates 32% of the genomic DNA. The CuTi method only isolates 12% DNA compared to the silica particle TNA method.

Figure 36:
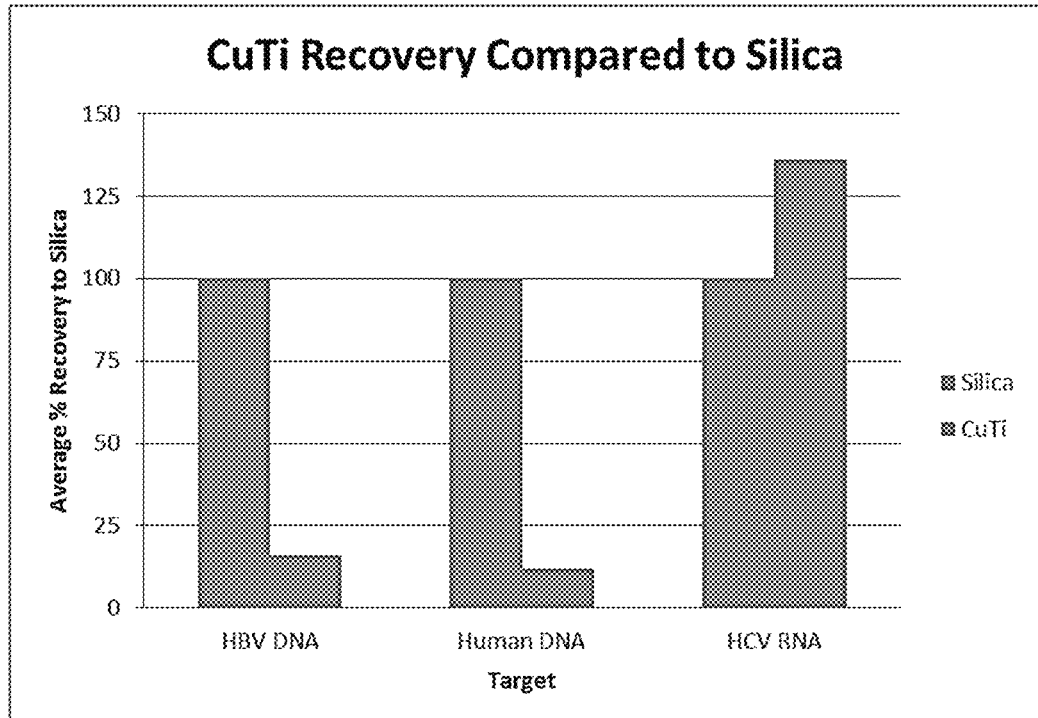
FIG. 36 shows isolation of RNA and DNA by CuTi particles.
Figure 37A:
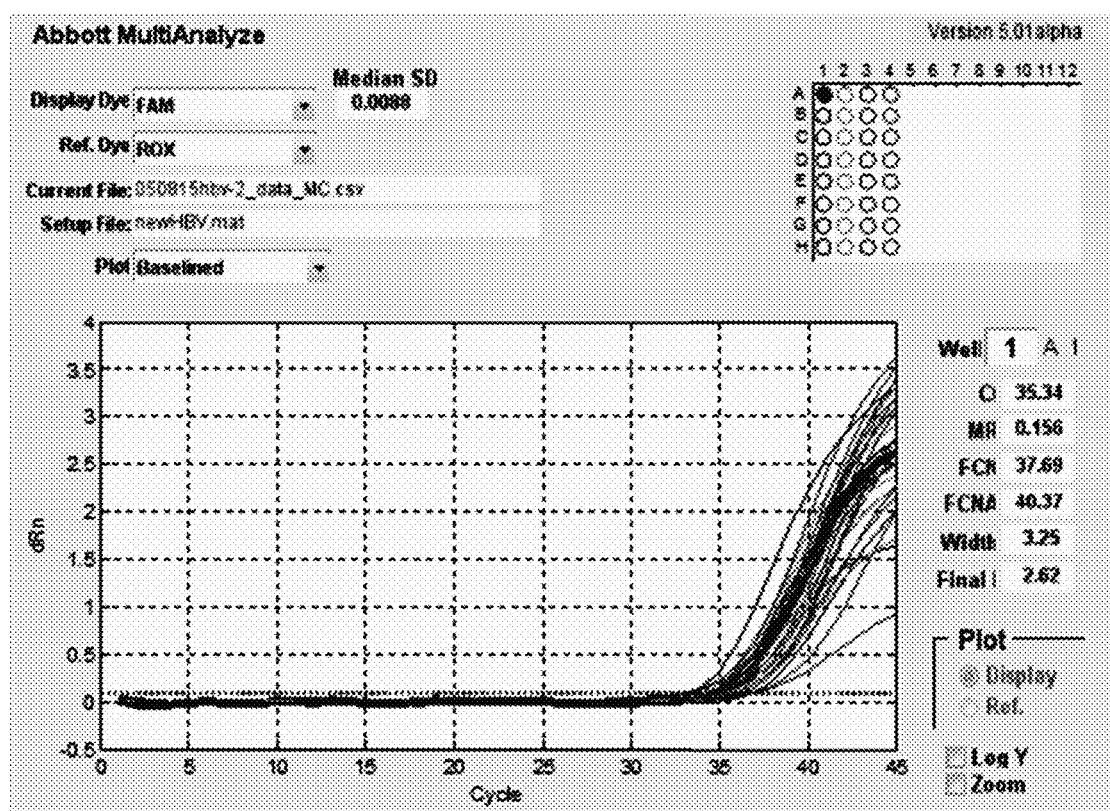
FIG. 37A-F shows isolation of HBV DNA from CuTi and silica.
Figure 37B:
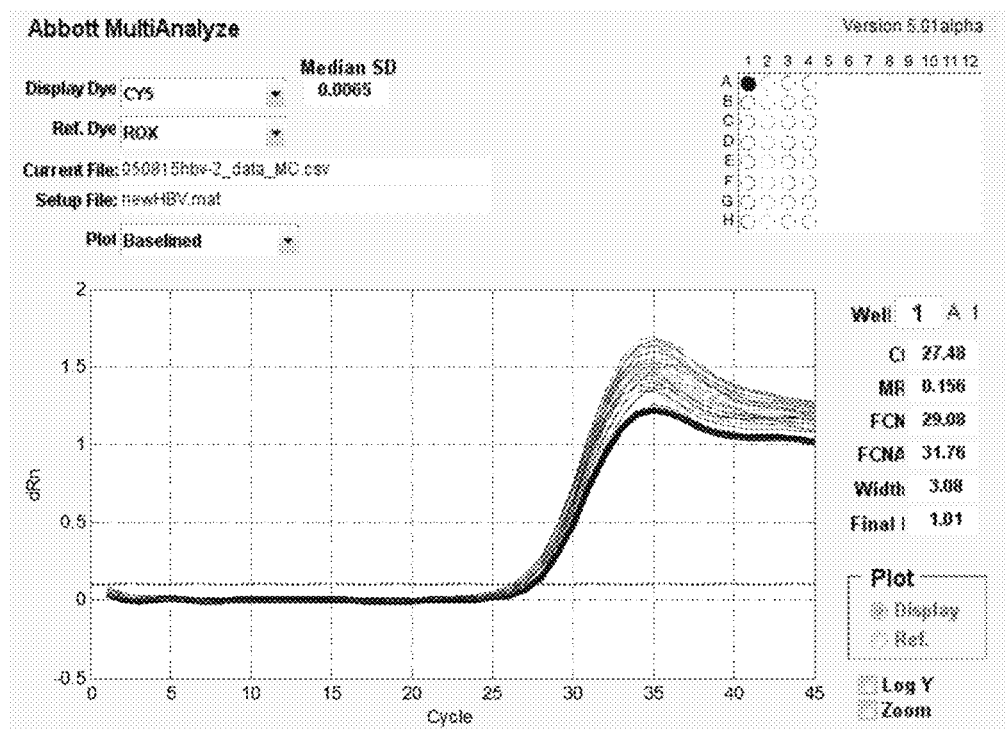
Figure 37C:
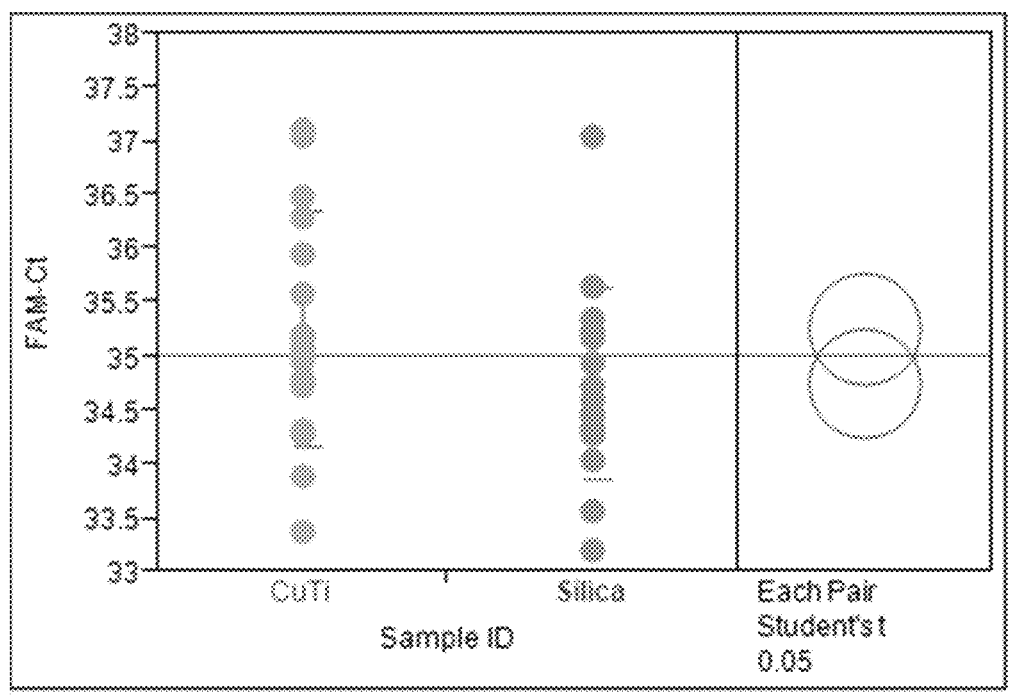
Figure 37D:
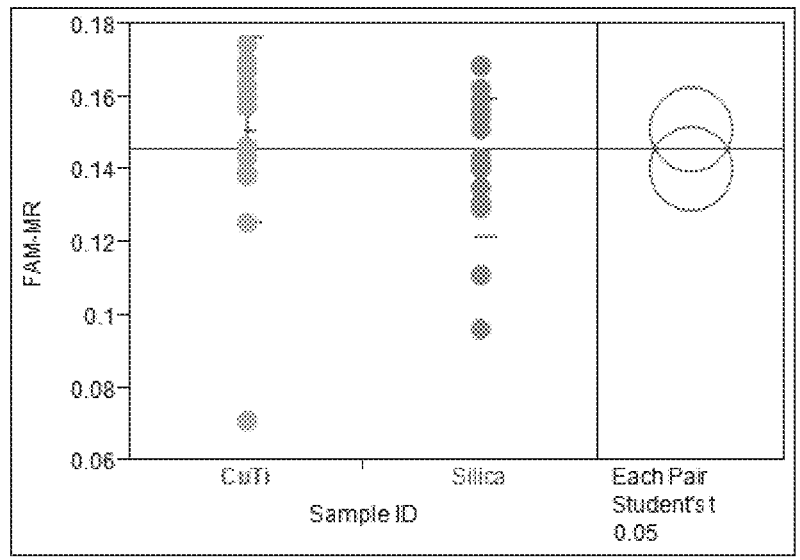
Figure 37E:
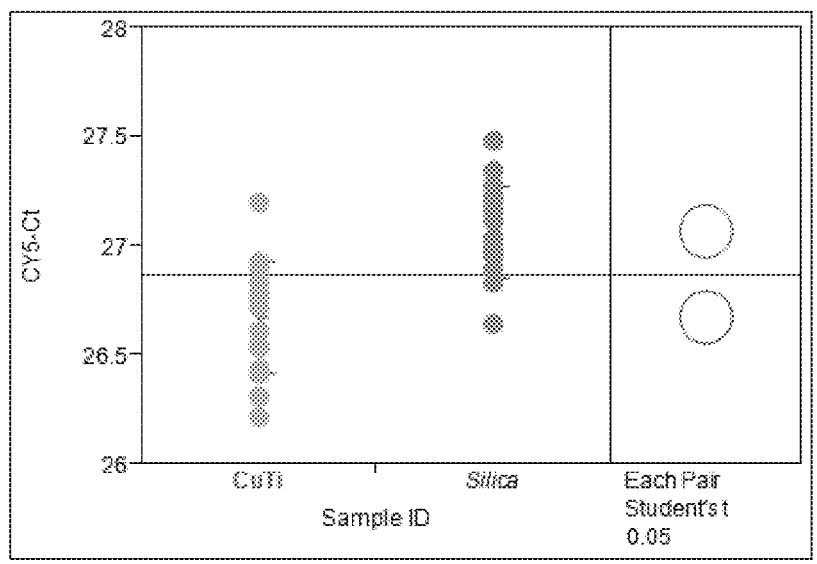
Figure 37F:
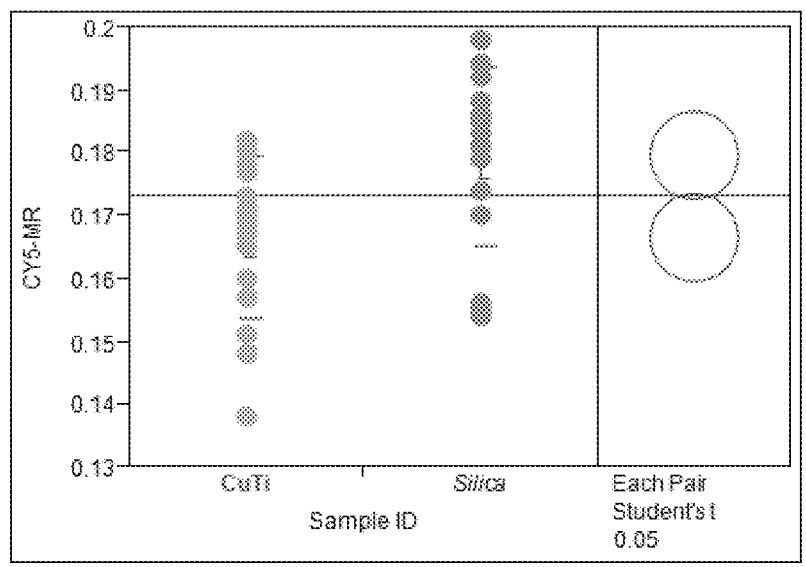
Figure 38A:
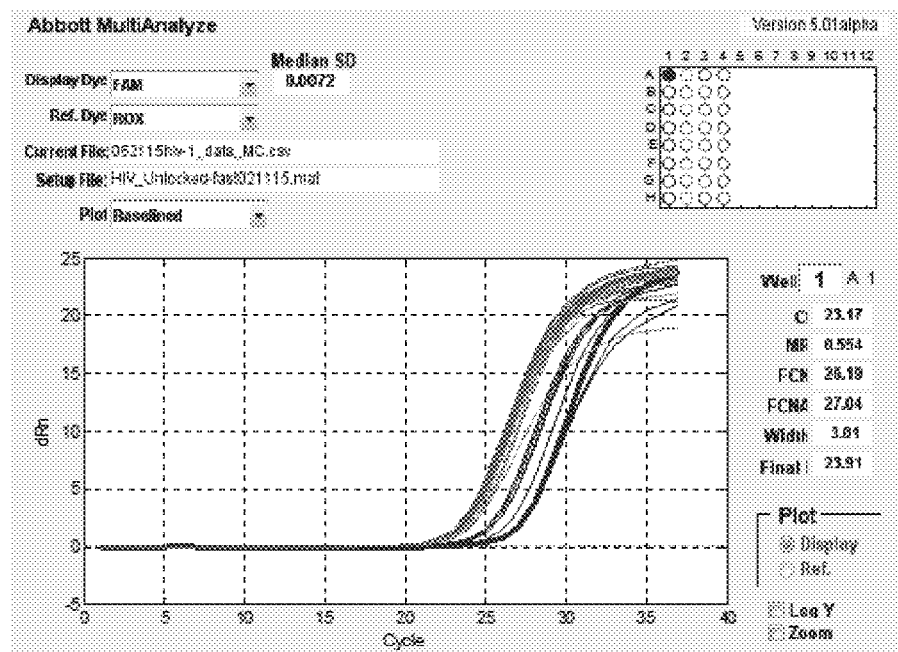
FIG. 38A-I shows isolation of HIV RNA from CuTi using different lysis buffer conditions.
Figure 38B:
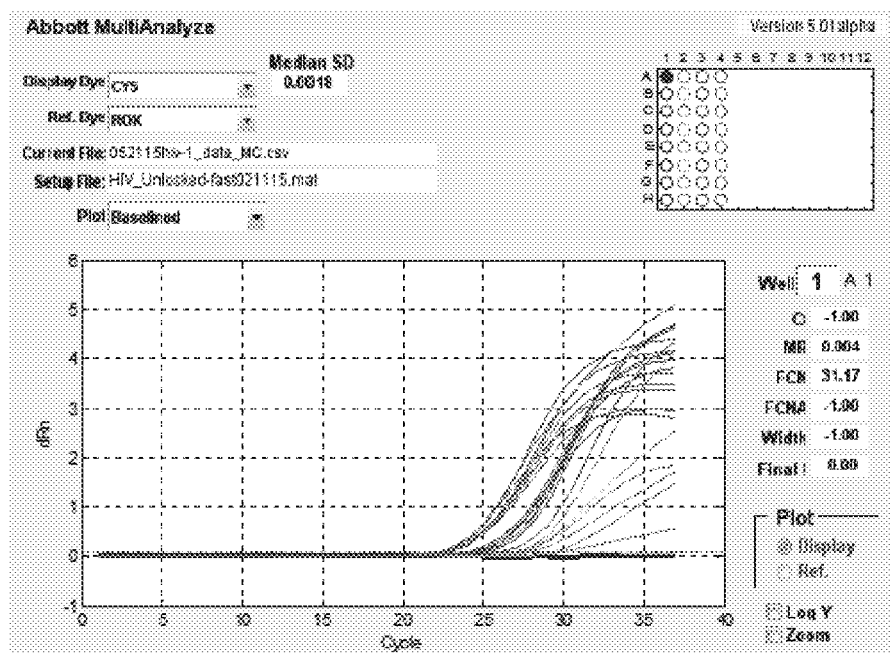
Figure 38C:
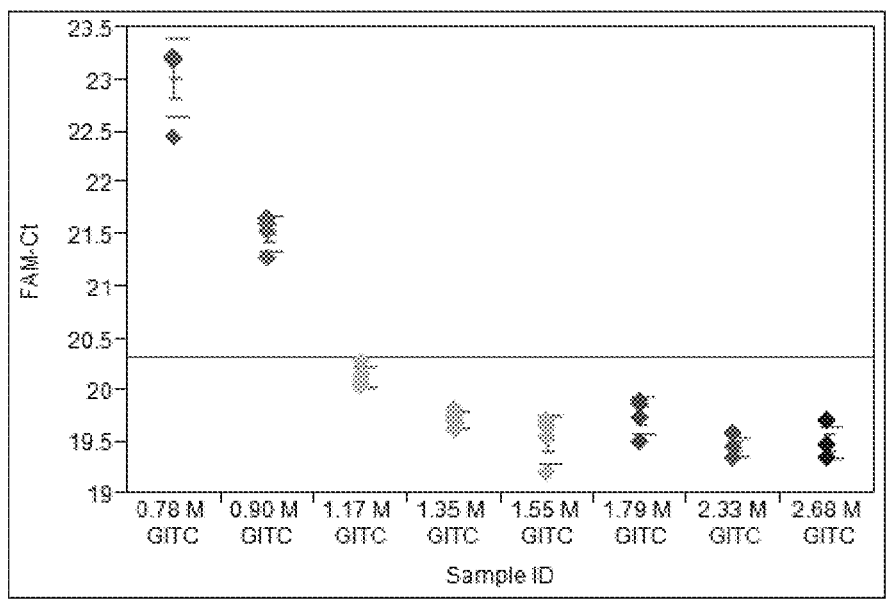
Figure 38D:
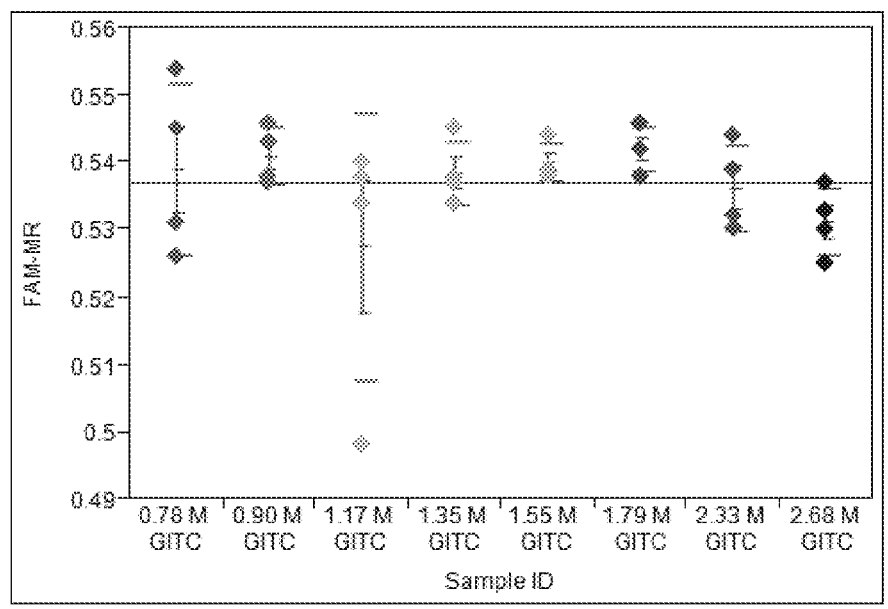
Figure 38E:
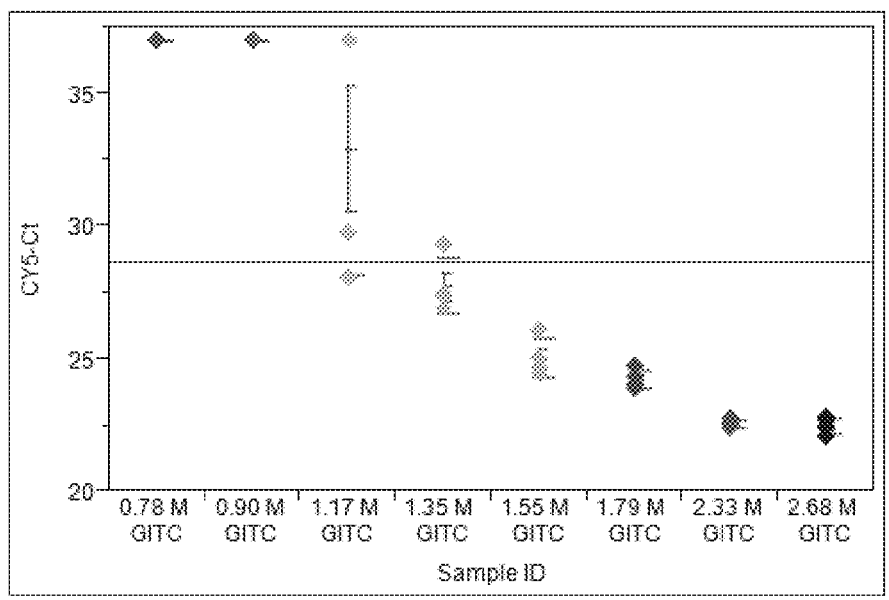
Figure 38F:
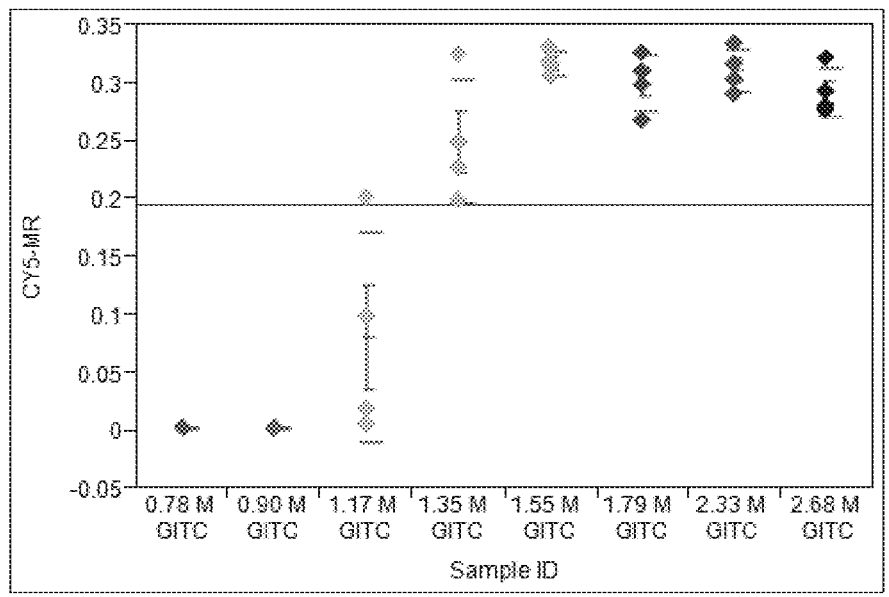
Figure 38G:
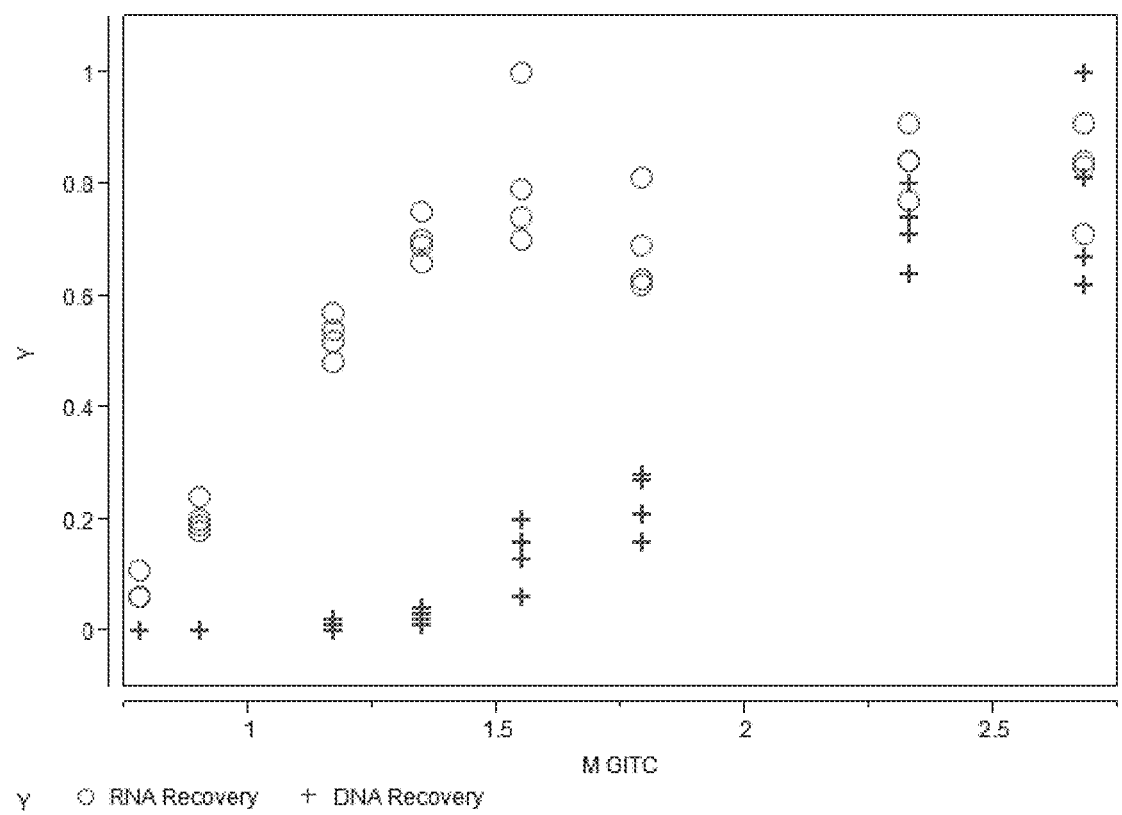
Figure 38H:
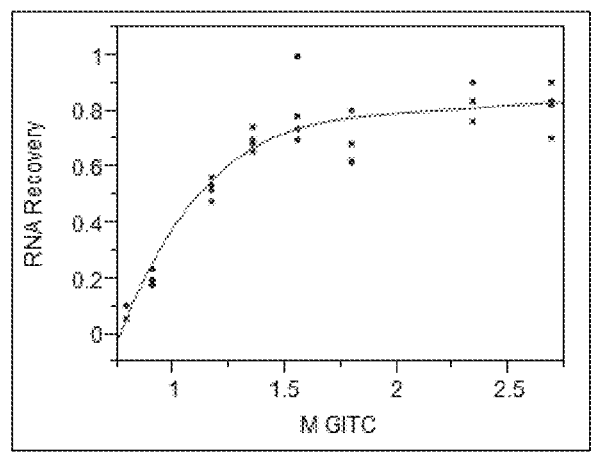
Figure 38I:
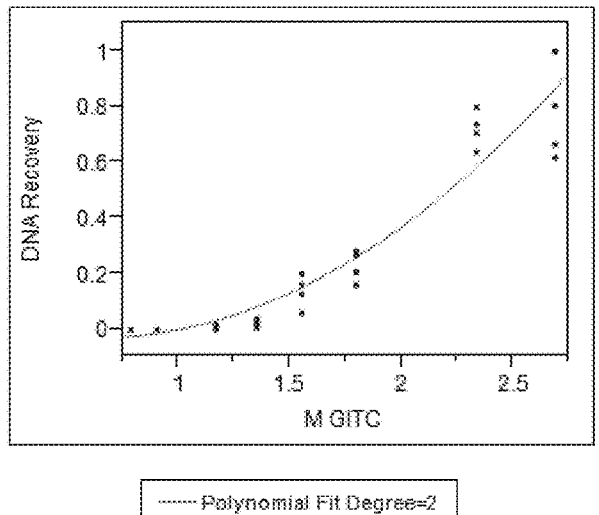
Figure 39A:
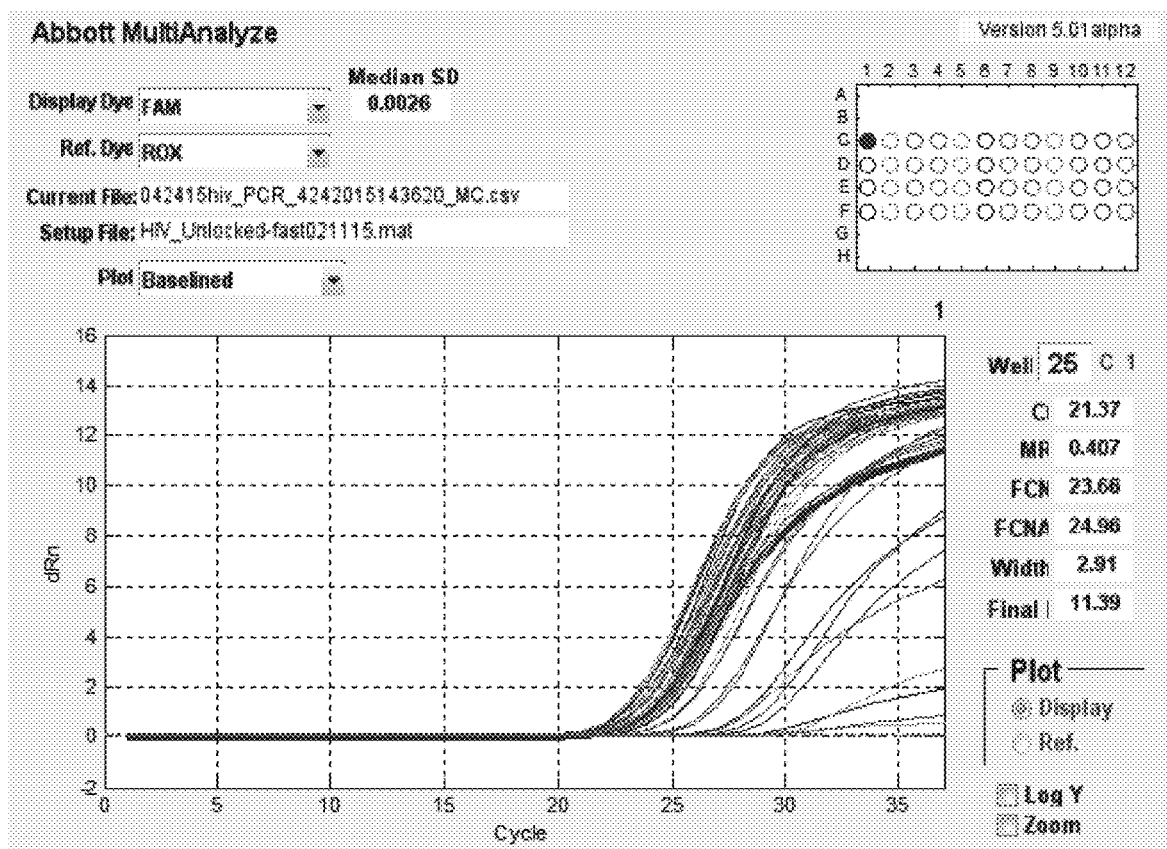
FIG. 39A-F shows HIV binding data for different metal particles.
Figure 39B:
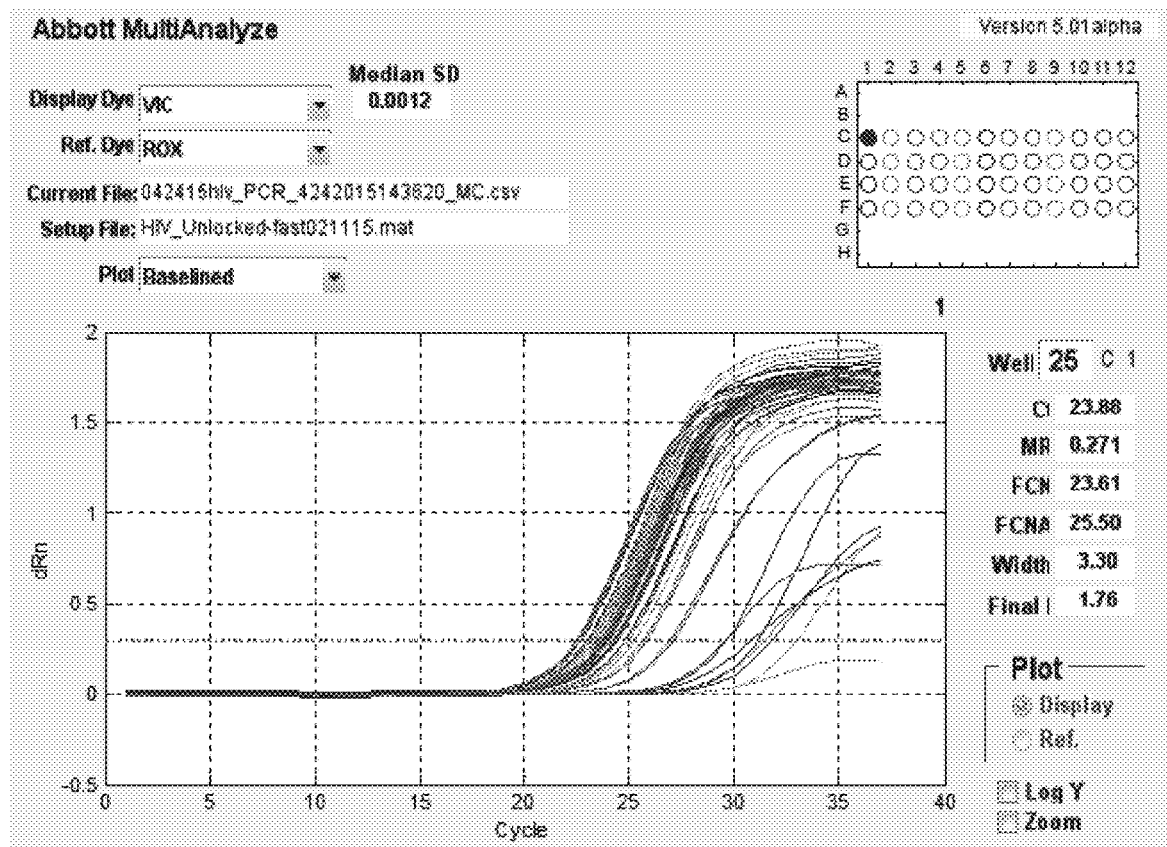
Figure 39C:
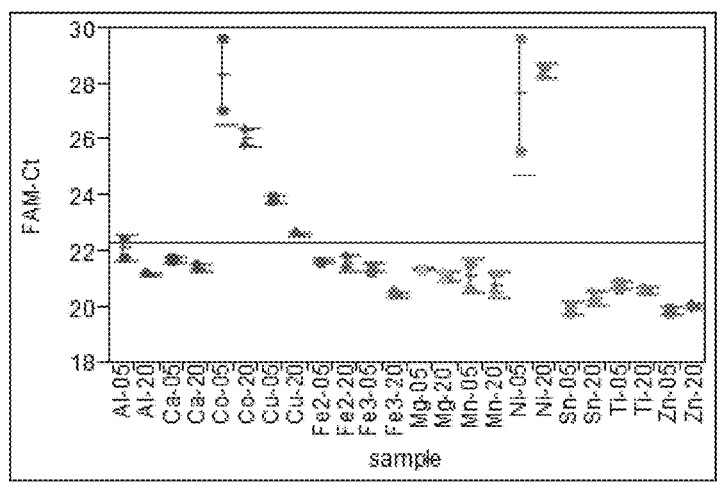
Figure 39D:
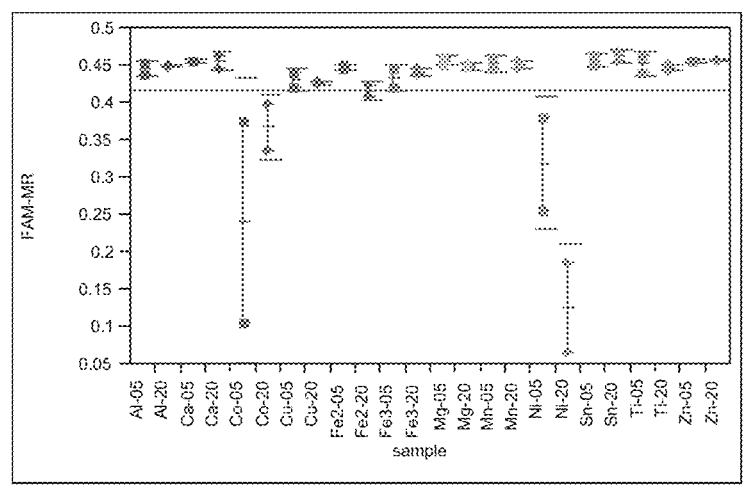
Figure 39E:
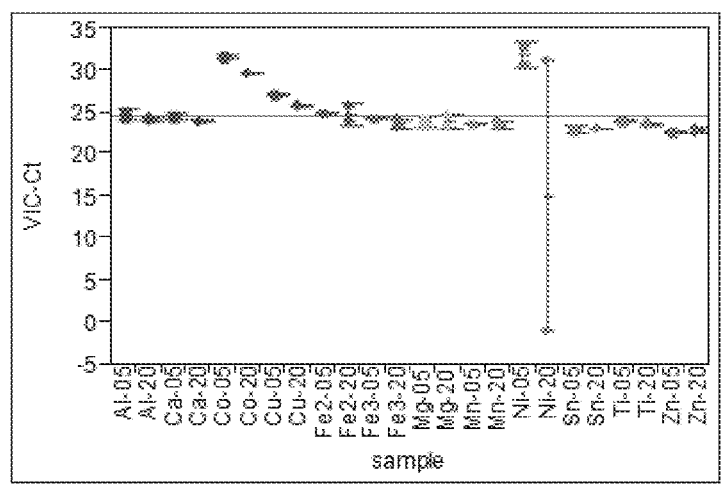
Figure 39F:
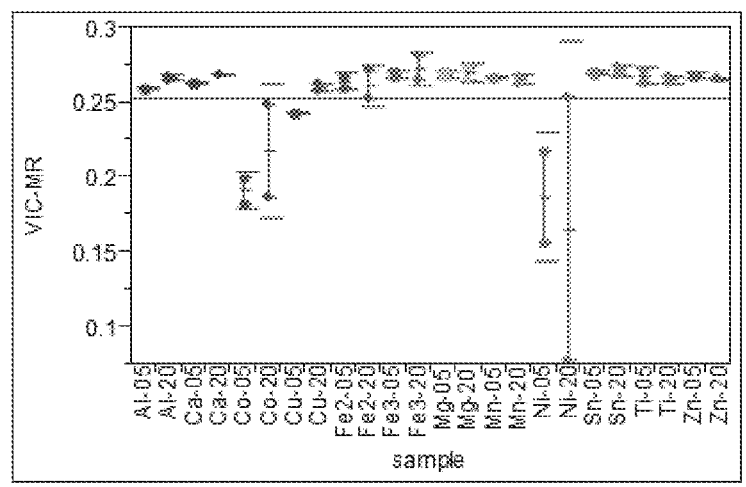
Figure 40A:
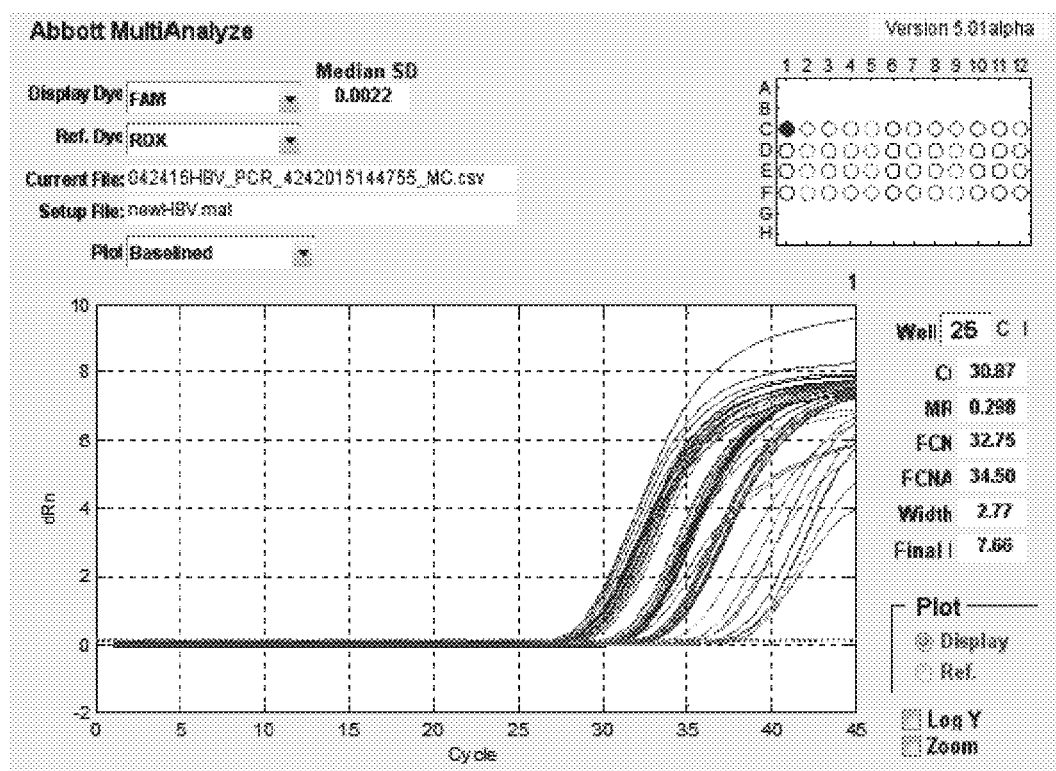
FIG. 40A-F shows HBV binding data for different metal particles.
Figure 40B:
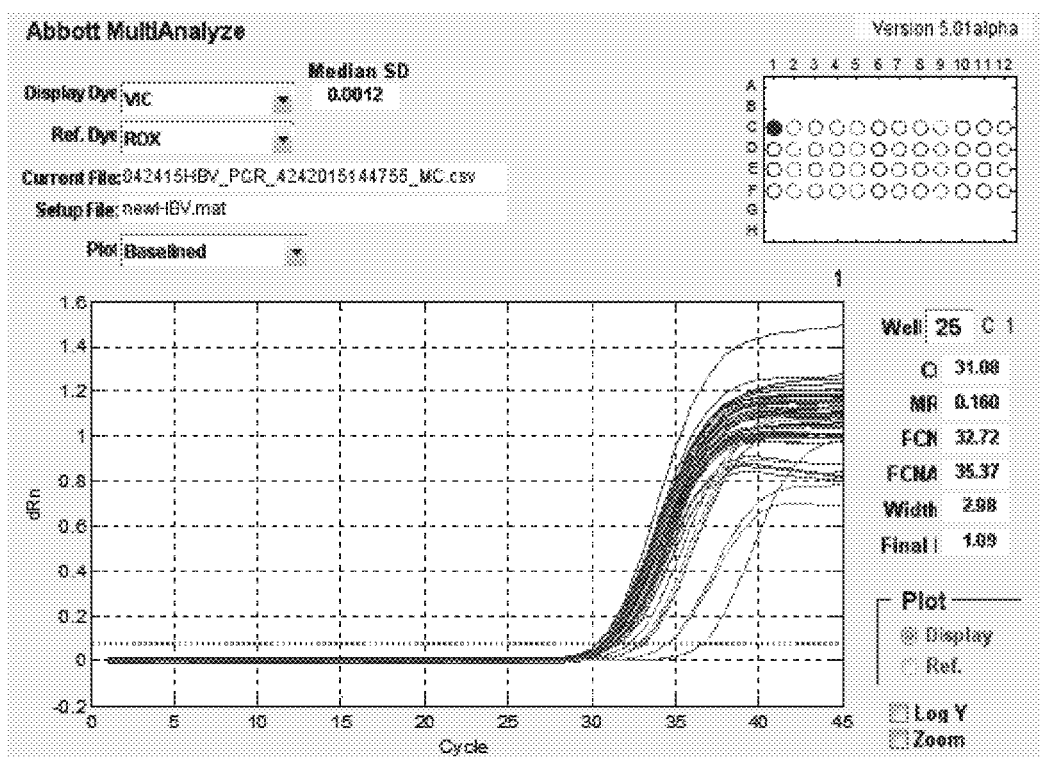
Figure 40C:
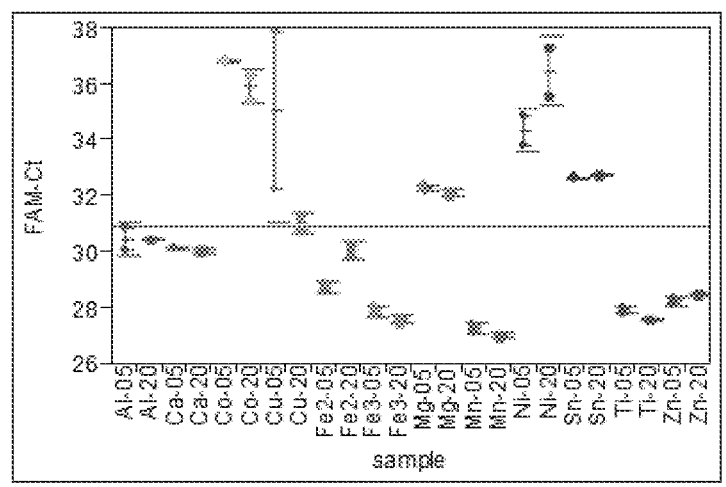
Figure 40D:
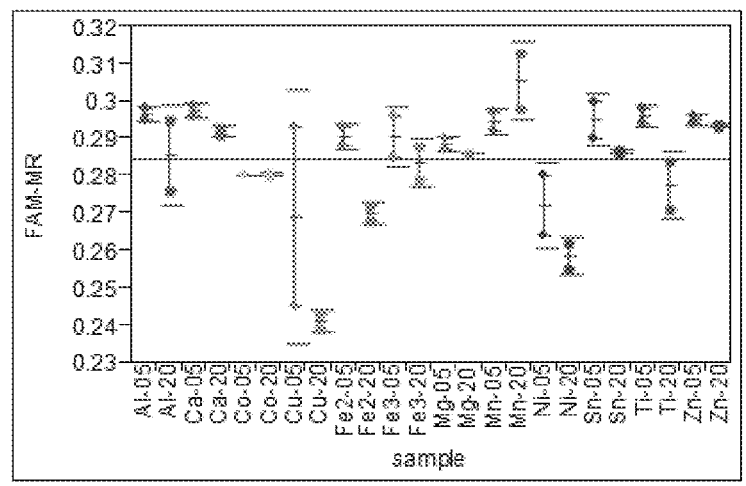
Figure 40E:
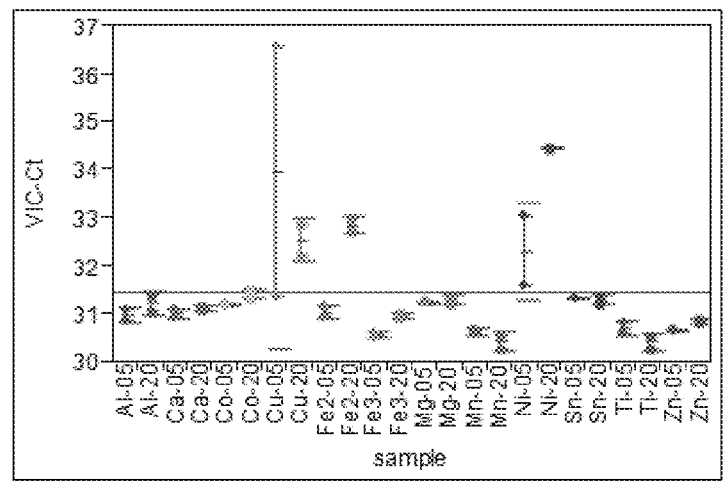
Figure 40F:
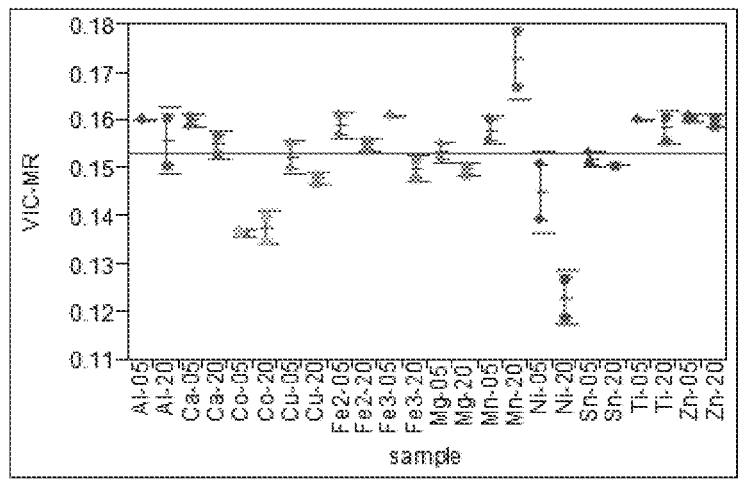

The CuTi particles capture RNA as well as other methods but do not capture DNA as well as the other methods. This means that the CuTi particles can selectively capture RNA. This is important in the measure method of RNA viruses. It is not desirable to capture DNA because the presence of pro-viral DNA in the extraction could give an inaccurate determination of the amount of viral particles (FIG. 36 and the Table below shows CuTi recovery compared to Silica)

| | % Recovery | |
|---|---|---|
| Target | Silica | CuTi |
| HBV DNA | 100 | 16 |
| Human DNA | 100 | 12 |
| HCV RNA | 100 | 136 |

Example 8

This example describes isolation of DNA using CuTi.

HBV was used at a concentration below LOD samples (10 cps/ml). For CuTi extractions, lysis buffer w/o ethanol for lysis and wash 1 were used, water was used for wash 2, and 5 mM Elution buffer was used. For the silica extraction, lysis and wash 1 used 70 ml ethanol added to 70 ml lysis buffer. For wash 2, 70 ml ethanol was added to 25 ml wash 2 (water).

Samples were HBV at a final concentration of 10 IU/ml. The table below shows the different samples tested and assay protocols.

| 8 samples | 8 samples | 8 samples | 8 samples |
|---|---|---|---|
| 20 ul IC | 20 ul IC | 20 ul IC | 20 ul IC |
| 1500 ul lysis buffer total | 1500 ul lysis buffer total | 500 ul lysis buffer total | 500 ul lysis buffer total |
| 50 ul PK | 50 ul PK | 50 ul PK | 50 ul PK |
| 150 ul LB | 150 ul LB | 150 ul LB | 150 ul LB |
| 200 ul sample | 200 ul sample | 200 ul sample | 200 ul sample |
| 25 ul Silica MMP | 25 ul Silica MMP | 100 ul CuTi | 100 ul CuTi |
| 500 wash 1 | 500 wash 1 | 500 wash 1 | 500 wash 1 |
| 800 wash 2A | 800 wash 2A | 800 wash 2A | 800 wash 2A |
| 800 wash 2B | 800 wash 2B | 800 wash 2B | 800 wash 2B |
| 55 ul elution | 55 ul elution | 55 ul elution | 55 ul elution |
| 300 sec pk incubation | 300 sec pk incubation | 300 sec pk incubation | 300 sec pk incubation |
| 10 min lysis | 10 min lysis | 10 min lysis | 10 min lysis |
| 10 min elution | 10 min elution | 10 min elution | 10 min elution |

After extractions were completed, assays were setup and run as above. After analysis, data transferred to MultiAnalyze and JMP as above. Results are shown in FIGS. 37A-F. Results show that all the samples at 10 IU/ml were detected with both the CuTi particles and the silica particles. For example, 40/40 were detected for the CuTi particles and 24/24 for the silica particles. In both experiments the target HBV signals were statistically identical, although the MR for the CuTi trends higher than the silica particles. The internal control in the first experiment had a higher CT value for the CuTi particles but was lower than the silica particles in the second experiment. The HBV target was detected at below LOD at 100% detection with the CuTi particle preparations and the internal control was also detected at levels comparable to the silica process.

Example 9

This example describes DNA and RNA capture with CuTi particles. Different lysis buffer dilutions were tested to determine any differential DNA and RNA recovery. A total of 8 lysis buffer concentrations were tested. HIV (1000 molecules/ml) and HBV nucleic acids were tested. GITC is the primary component of the lysis buffer. The table below shows lysis buffer conditions.

| Using 1 ml total lysis as lysis buffer and water-total vol is 1.37 ml | | | | | | | | | |
|---|---|---|---|---|---|---|---|---|---|
| IC | sample | add lysis | add water | lb | MMP | MGITC lysis | lysis vol | total vol | total GITC |
| 0.02 | 1 | 0 | 0.2 | 1.3 | 0.1 | 1.566 | 1.3 | 2.62 | 0.777022901 |
| 0.02 | 1 | 0.2 | 0 | 1.3 | 0.1 | 1.566 | 1.5 | 2.62 | 0.896564885 |
| 0.02 | 1 | 0 | 0.2 | 1.3 | 0.1 | 2.35 | 1.3 | 2.62 | 1.166030534 |
| 0.02 | 1 | 0.2 | 0 | 1.3 | 0.1 | 2.35 | 1.5 | 2.62 | 1.345419847 |
| 0.02 | 1 | 0 | 0.2 | 1.3 | 0.1 | 3.13 | 1.3 | 2.62 | 1.553053435 |
| 0.02 | 1 | 0.2 | 0 | 1.3 | 0.1 | 3.13 | 1.5 | 2.62 | 1.791984733 |
| 0.02 | 1 | 0 | 0.2 | 1.3 | 0.1 | 4.7 | 1.3 | 2.62 | 2.332061069 |
| 0.02 | 1 | 0.2 | 0 | 1.3 | 0.1 | 4.7 | 1.5 | 2.62 | 2.690839695 |

Multianalyze 5 was used to analyze data. Results are shown in FIG. 38 A-I. The percent recovery was calculated using the lowest CT as the maximal value. Each CT higher represents ½ the recovery of the CT below (a Cycle Threshold is the difference from one amplification cycle to the next, each cycle results in a doubling of the amount of amplicon.) The CT differences were calculated and the percent recovery under each GITC level (FIGS. 38H-I) was calculated for the RNA and the DNA recovery.

The DNA recovery is highest at high levels of GITC (2.33 M GITC and above) while the RNA recovery is high at 1.35 M GITC and above. At 1.35 M GITC using the extraction conditions described above (58° C., 1 ml sample and 1.5 ml lysis buffer) there is almost maximal RNA recovery but less than 10% DNA recovery for the RNA and DNA targets described above.

Example 10

This example describes DNA and RNA binding by metal particles. The purpose of this experiment was to expand the metal oxides tested for RNA and DNA binding beyond the CuTi particle formulation.

The following particles were prepared:

| | Metal Chlorides |
|---|---|
| 1 | AlCl3 |
| 2 | Calcium chloride 1.0M |
| 3 | CoCl2 |
| 4 | Chromium(III)chloride |

-continued

| | Metal Chlorides |
|---|---|
| 5 | Copper(II) chloride |
| 6 | FeCl2-Iron(II)chloride |
| 7 | FeCl2-Iron(III)chloride |
| 8 | Manganese (II) Chloride |
| 9 | MgCL2 |
| 10 | NiCl2 |
| 11 | SnCl2 |
| 12 | Titanium(III) chloride solution |
| 13 | Zinc chloride |

Particles were prepared in in 125 ml PETG bottles with 1 g particles. 100 ml water was added to each. Bottle 1 had 0.5 ml of $AlCl_3$—HCl; Bottle 2 had 0.5 ml of $CaCL2+0.5$ ml 3M HCl; Bottle 3 had 0.5 ml $CoCl_2$—HCl; Bottle 4 had 0.5 ml $CuCl_2$—HCl. Bottles were incubated on rotator for 50 minutes. Particles were then neutralized with 0.63 ml 50% NaOH.

The particles were tested for HIV and HBV extraction using the following reagents.

Extraction
Reagents
Lysis buffer
Wash2
Water
Elution buffer (20 mM phosphate)
Elution buffer (5 mM phosphate)
Neg Diluent
HBV IC
HIV IC
The HIV IC (17 ul) was added directly to the lysis well during processing
The HBV IC was added directly to the master mix prior to running the assay. No sample prep on the HBV IC, to look for assay inhibition directly.

Particles (100 μl) are added manually to the lysis well prior to starting extraction.

Bottle 1 - Al oxide ppt
Bottle 2 - CaCl oxide ppt
Bottle 3 - Cl oxide ppt
Bottle 4 - Cu oxide ppt
Bottle 5 - Fe2 oxide ppt
Bottle 6 - Fe3 oxide ppt
Bottle 7 - Mg oxide ppt
Bottle 8 - Mn oxide ppt
Bottle 9 - Ni oxide ppt
Bottle 10 - Sn oxide ppt
Bottle 11 - Ti oxide ppt
Bottle 12 - Zn oxide ppt

| position | module #1 | module #2 | module #3 |
|---|---|---|---|
| #1 | Bottle 1 - Al oxide ppt | Bottle 9 - Ni oxide ppt | Bottle 5 - Fe2 oxide ppt |
| #2 | Bottle 2 - CaCl oxide ppt | Bottle 10 - Sn oxide ppt | Bottle 6 - Fe3 oxide ppt |
| #3 | Bottle 3 - Cl oxide ppt | Bottle 11 - Ti oxide ppt | Bottle 7 - Mg oxide ppt |
| #4 | Bottle 4 - Cu oxide ppt | Bottle 12 - Zn oxide ppt | Bottle 8 - Mn oxide ppt |
| #5 | Bottle 5 - Fe2 oxide ppt | Bottle 1 - Al oxide ppt | Bottle 9 - Ni oxide ppt |
| #6 | Bottle 6 - Fe3 oxide ppt | Bottle 2 - CaCl oxide ppt | Bottle 10 - Sn oxide ppt |
| #7 | Bottle 7 - Mg oxide ppt | Bottle 3 - Cl oxide ppt | Bottle 11 - Ti oxide ppt |
| #8 | Bottle 8 - Mn oxide ppt | Bottle 4 - Cu oxide ppt | Bottle 12 - Zn oxide ppt |

The 2nd Extraction same as the first except that the elution buffer was 20 mM phosphate undiluted and a two-step elution (25 ul of 20 mM then 75 ul of water).

After extraction, particles were assayed for binding to HBV and HIV using RealTime assays described above.

FIGS. 39A-F shows HIV data for the different particles. FIGS. 40A-F show HBV data for the different particles.

The different metal oxides show differential binding to HIV and HBV. Some of the eluates show inhibition in the reactions as can be seen in the IC signal from HBV. Nickel and Cobalt oxides show inhibition. Cu and Fez also show inhibition. To compare the relative recovery of RNA and DNA, the cycle threshold values (CT) were used to calculate the relative recovery of the targets to the particles that gave the best recovery. For example, if one oxide had a CT of 20, and another had a CT value of 21, then the second oxide recovered ½ the amount of the first. If another had a CT value of 22, then it only recovered ¼ the amount of the first. The calculation is CT difference from the lowest value (best recovery) which is then used as the exponent to $2^X$

| | | diff | max | HBV % Recovery |
|---|---|---|---|---|
| Al-05 | 2 | 30.455 | 3.43 | 10.77787 | 9% |
| Al-20 | 2 | 30.45 | 3.43 | 10.74058 | 9% |
| Ca-05 | 2 | 30.135 | 3.11 | 8.633826 | 12% |
| Ca-20 | 2 | 30.045 | 3.02 | 8.111676 | 12% |
| Co-05 | 2 | 36.825 | 9.80 | 891.4438 | 0% |
| Co-20 | 2 | 35.91 | 8.89 | 472.7717 | 0% |
| Cu-05 | 1 | 32.24 | 5.22 | 37.14253 | 3% |
| Cu-20 | 2 | 31.055 | 4.03 | 16.33619 | 6% |
| Fe2-05 | 2 | 28.74 | 1.72 | 3.282966 | 30% |
| Fe2-20 | 2 | 30.065 | 3.04 | 8.224911 | 12% |
| Fe3-05 | 2 | 27.865 | 0.84 | 1.79005 | 56% |
| Fe3-20 | 2 | 27.59 | 0.57 | 1.479388 | 68% |
| Mg-05 | 2 | 32.31 | 5.29 | 38.98913 | 3% |
| Mg-20 | 2 | 32.105 | 5.08 | 33.82458 | 3% |
| Mn-05 | 2 | 27.265 | 0.24 | 1.180993 | 85% |
| Mn-20 | 2 | 27.025 | 0.00 | 1 | 100% |
| Ni-05 | 2 | 34.36 | 7.34 | 161.4563 | 1% |
| Ni-20 | 2 | 36.48 | 9.46 | 701.8408 | 0% |
| Sn-05 | 2 | 32.635 | 5.61 | 48.84029 | 2% |
| Sn-20 | 2 | 32.76 | 5.74 | 53.26072 | 2% |
| Ti-05 | 2 | 27.92 | 0.90 | 1.85961 | 54% |
| Ti-20 | 2 | 27.575 | 0.55 | 1.464086 | 68% |
| Zn-05 | 2 | 28.24 | 1.22 | 2.321408 | 43% |
| Zn-20 | 2 | 28.5 | 1.48 | 2.779836 | 36% |

| | | diff | max | HIV % Recovery |
|---|---|---|---|---|
| Al-05 | 2 | 22.13 | 2.26 | 4.773343 | 21% |
| Al-20 | 2 | 21.16 | 1.29 | 2.436821 | 41% |
| Ca-05 | 2 | 21.725 | 1.85 | 3.605002 | 28% |
| Ca-20 | 2 | 21.42 | 1.55 | 2.918041 | 34% |

-continued

| | | | | | |
|---|---|---|---|---|---|
| Co-05 | 2 | 28.345 | 8.47 | 354.588 | 0% |
| Co-20 | 2 | 26.07 | 6.20 | 73.26235 | 1% |
| Cu-05 | 2 | 23.895 | 4.02 | 16.22335 | 6% |
| Cu-20 | 2 | 22.62 | 2.75 | 6.703897 | 15% |
| Fe2-05 | 2 | 21.66 | 1.79 | 3.446185 | 29% |
| Fe2-20 | 2 | 21.585 | 1.71 | 3.271608 | 31% |
| Fe3-05 | 2 | 21.405 | 1.53 | 2.887858 | 35% |
| Fe3-20 | 2 | 20.46 | 0.59 | 1.500039 | 67% |
| Mg-05 | 2 | 21.37 | 1.50 | 2.818642 | 35% |
| Mg-20 | 2 | 21.09 | 1.22 | 2.321408 | 43% |
| Mn-05 | 2 | 21.11 | 1.24 | 2.353813 | 42% |
| Mn-20 | 2 | 20.825 | 0.95 | 1.931873 | 52% |
| Ni-05 | 2 | 27.635 | 7.76 | 216.7668 | 0% |
| Ni-20 | 2 | 28.445 | 8.57 | 380.038 | 0% |
| Sn-05 | 2 | 19.995 | 0.12 | 1.086735 | 92% |
| Sn-20 | 2 | 20.34 | 0.47 | 1.380317 | 72% |
| Ti-05 | 2 | 20.8 | 0.93 | 1.898684 | 53% |
| Ti-20 | 2 | 20.605 | 0.73 | 1.658639 | 60% |
| Zn-05 | 2 | 19.875 | 0.00 | 1 | 100% |
| Zn-20 | 2 | 20.025 | 0.15 | 1.109569 | 90% |

Figure 41:
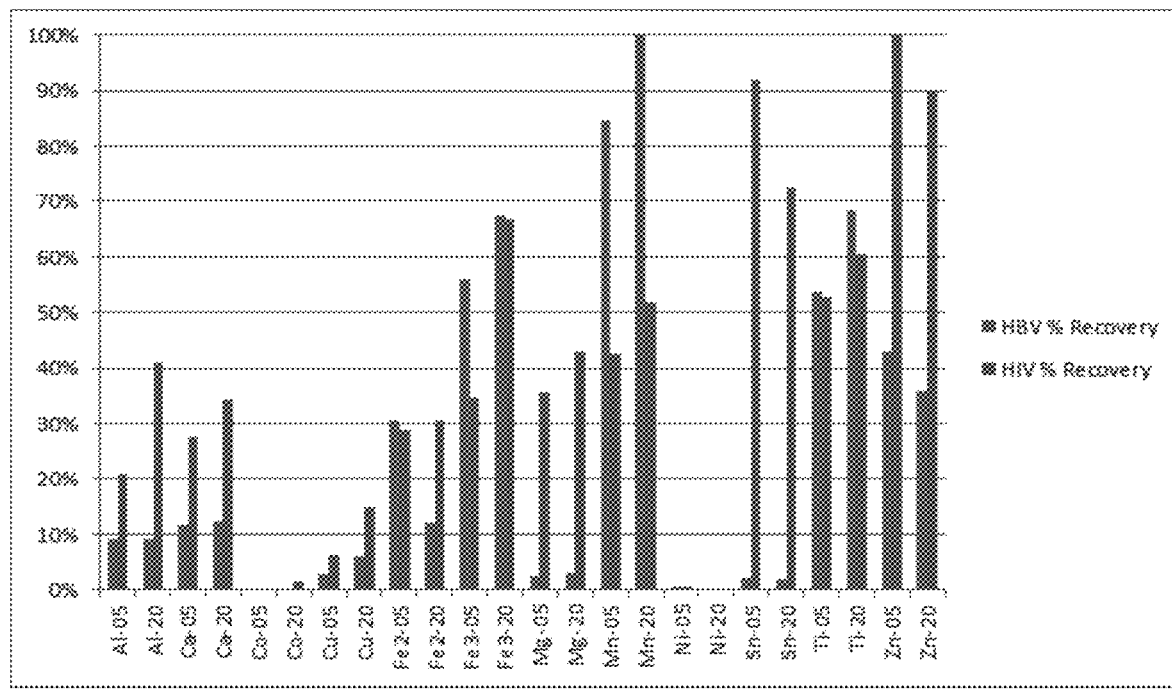
FIG. 41 shows recovery of HIV and HBV targets by metal particles.
Figure 42A:
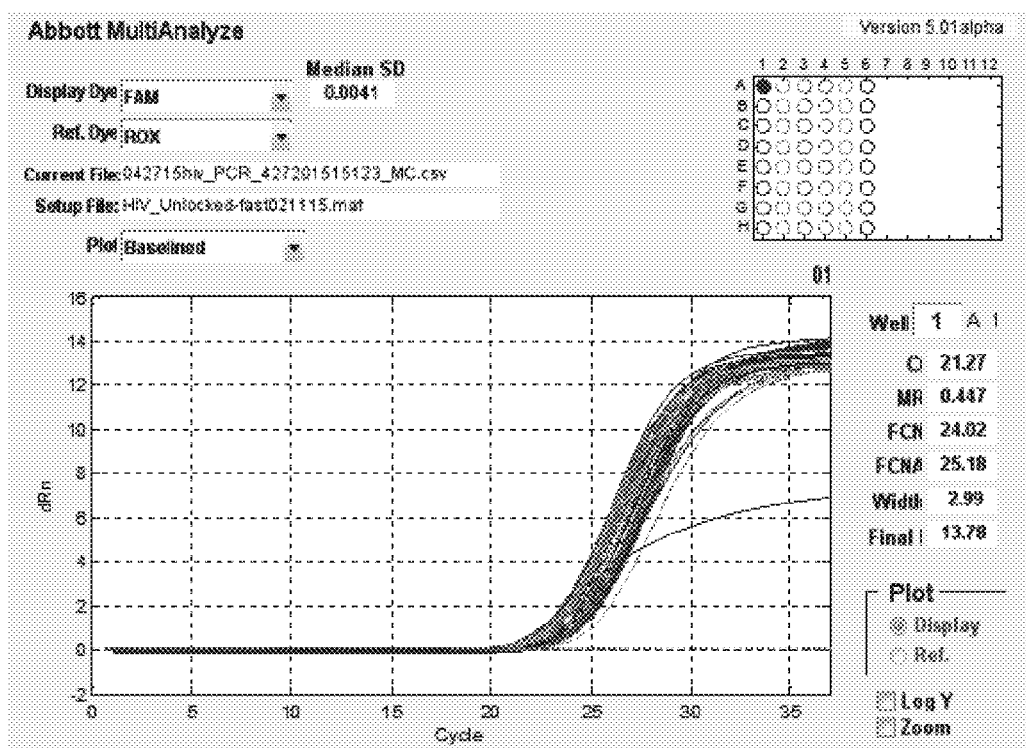
FIG. 42A-F HIV shows binding data for different metal particles.
Figure 42B:
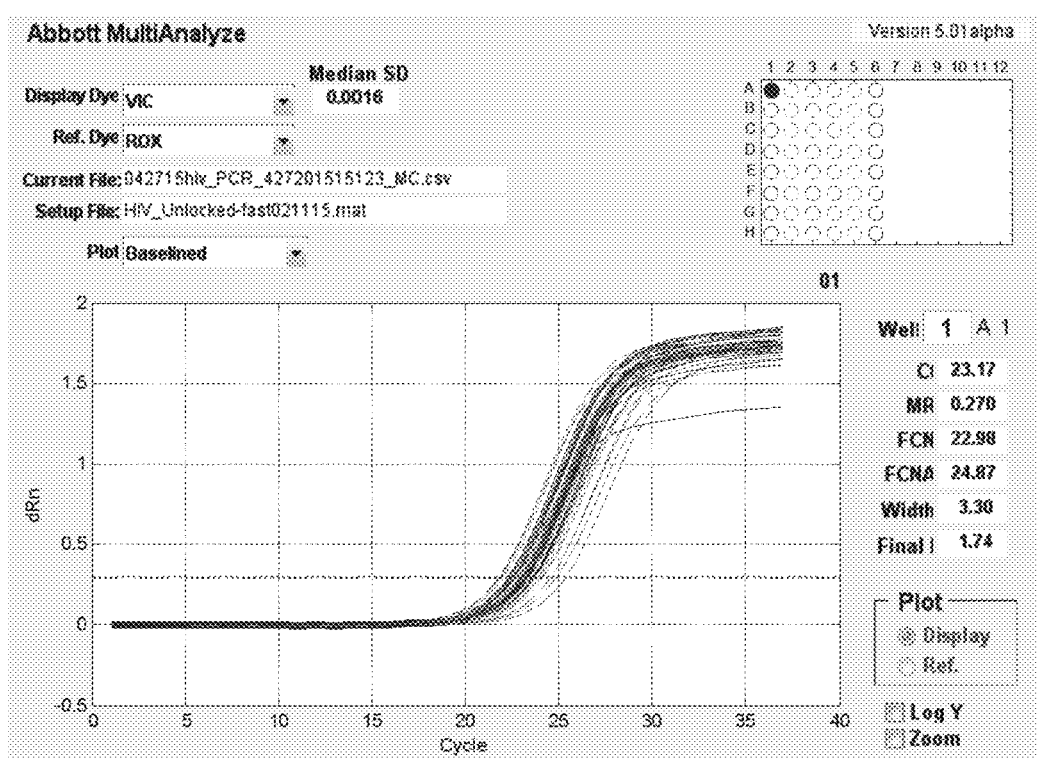
Figure 42C:
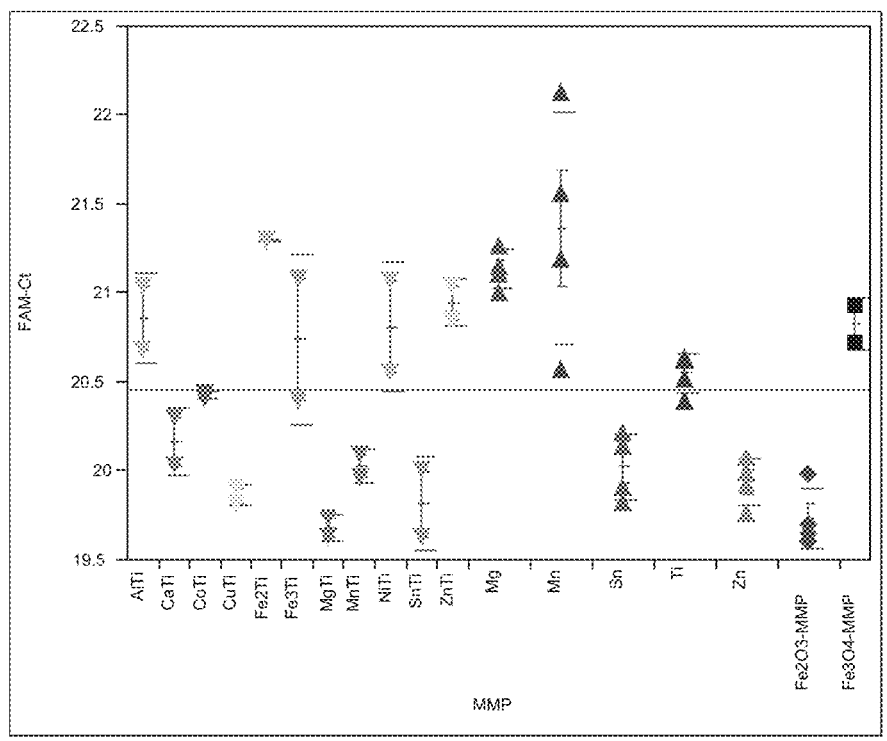
Figure 42D:
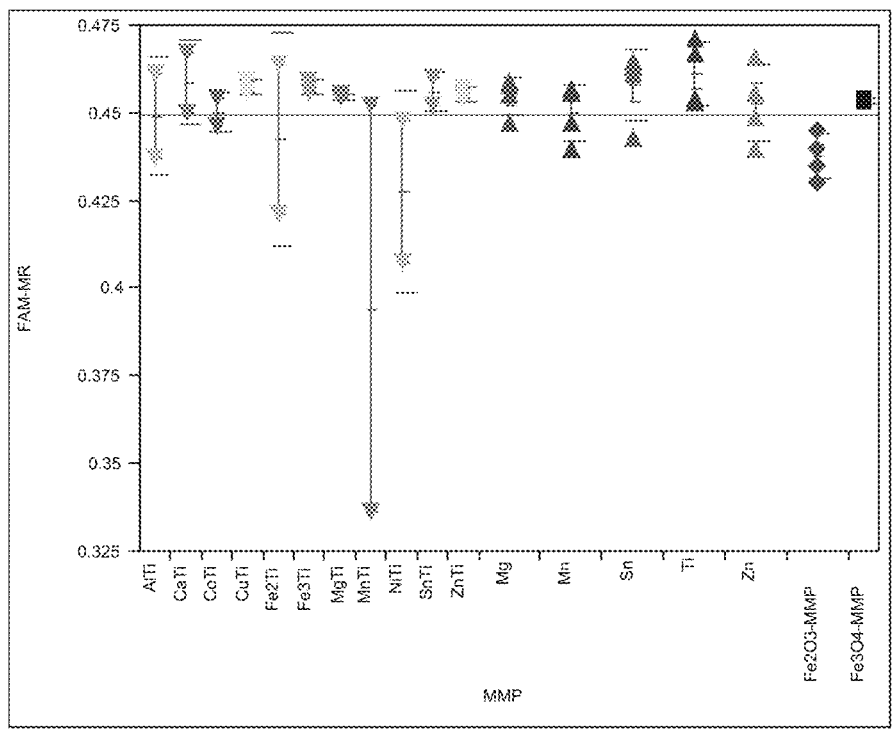
Figure 42E:
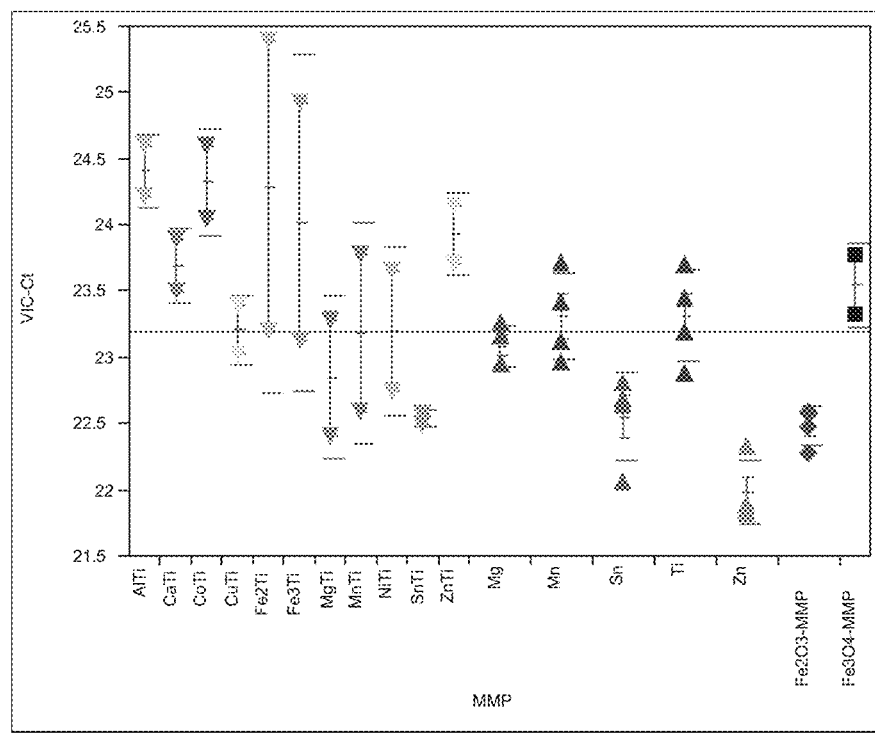
Figure 42F:
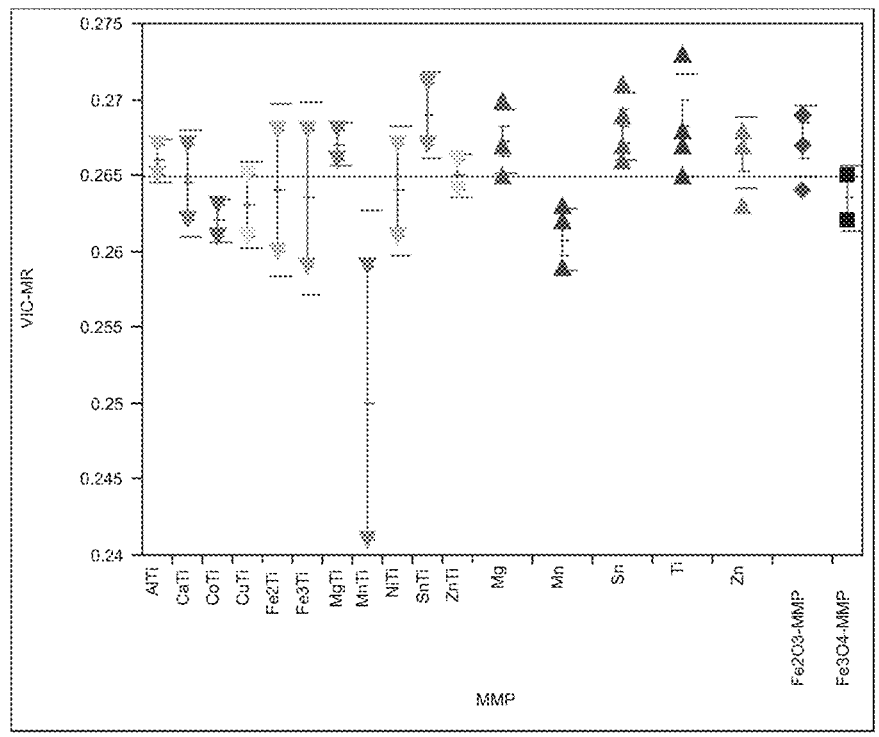
Figure 43A:
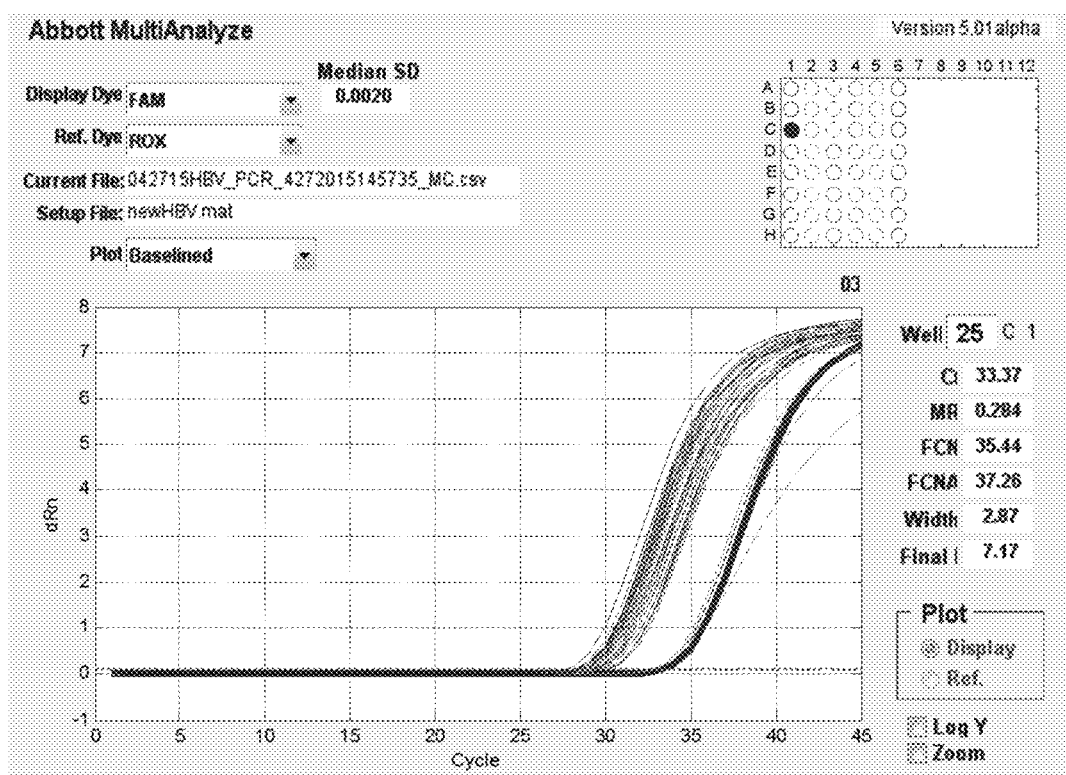
FIG. 43A-F shows HBV binding data for different metal particles.
Figure 43B:
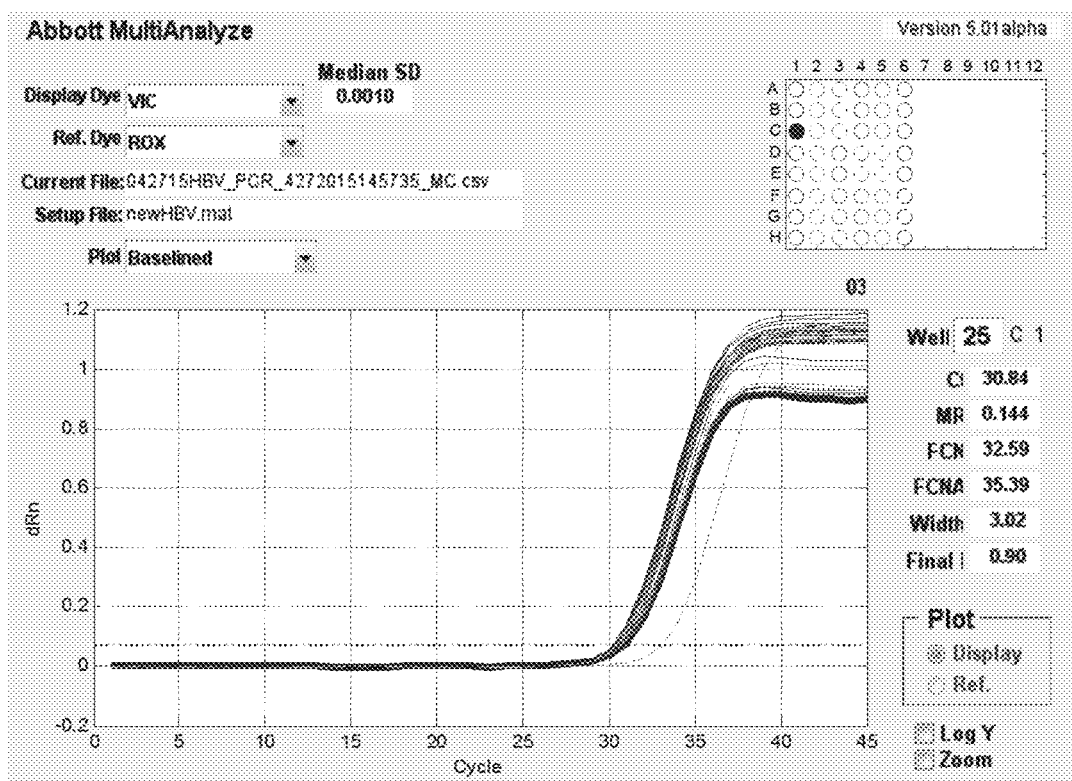
Figure 43C:
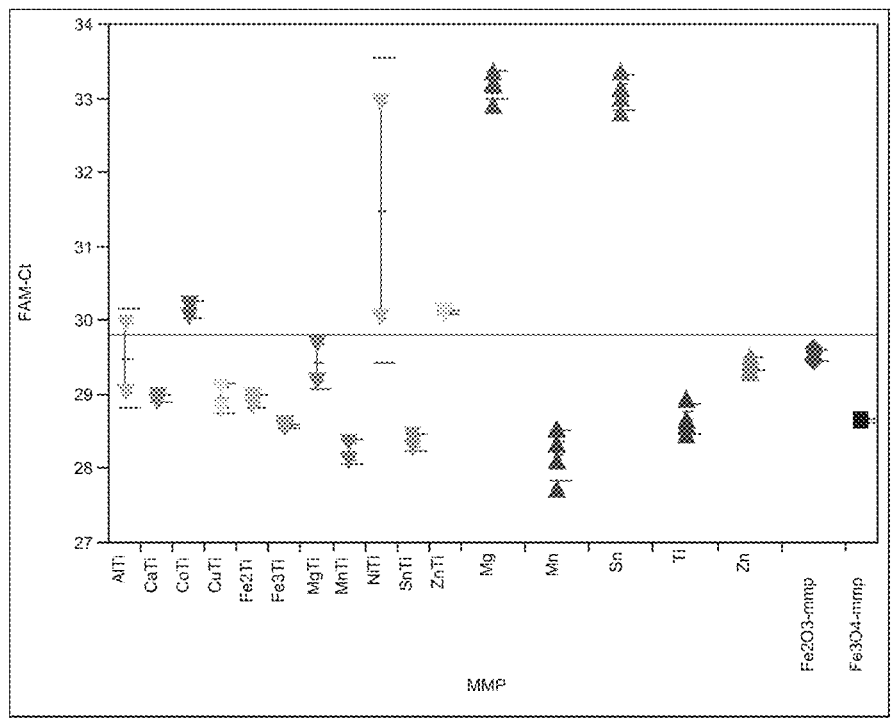
Figure 43D:
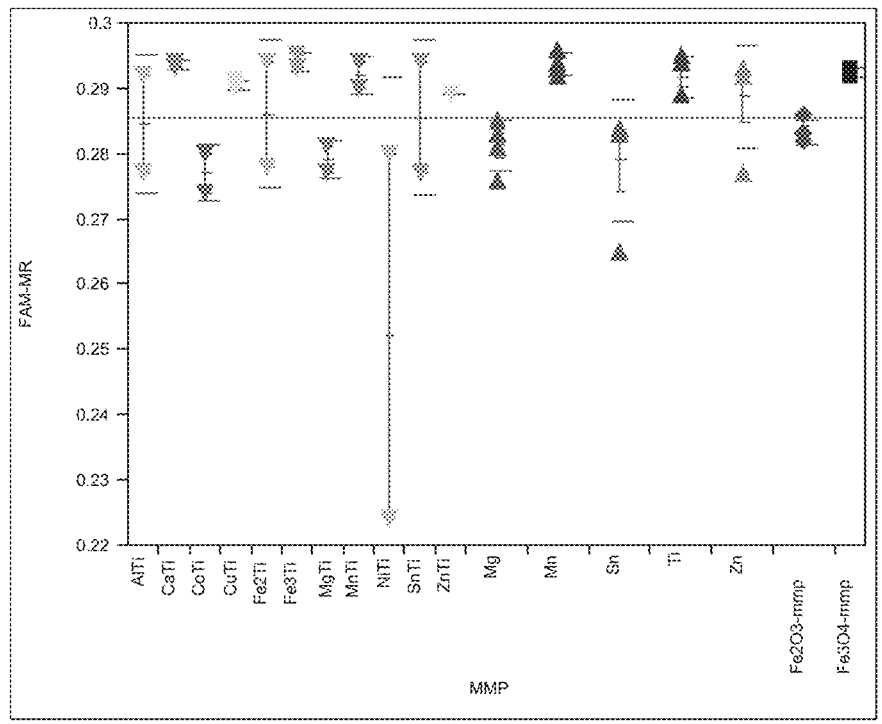
Figure 43E:
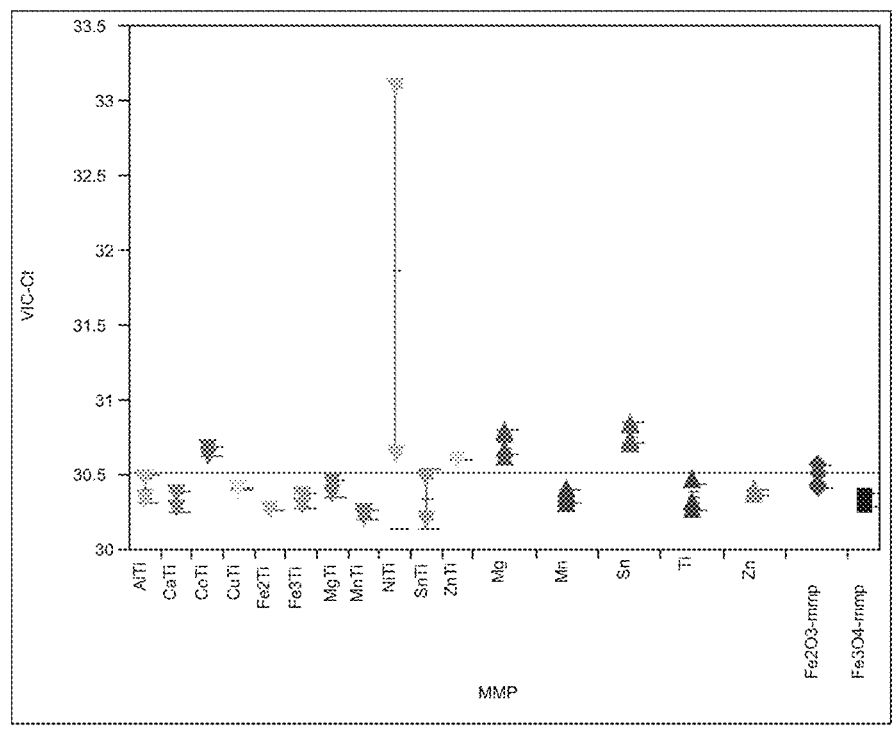
Figure 43F:
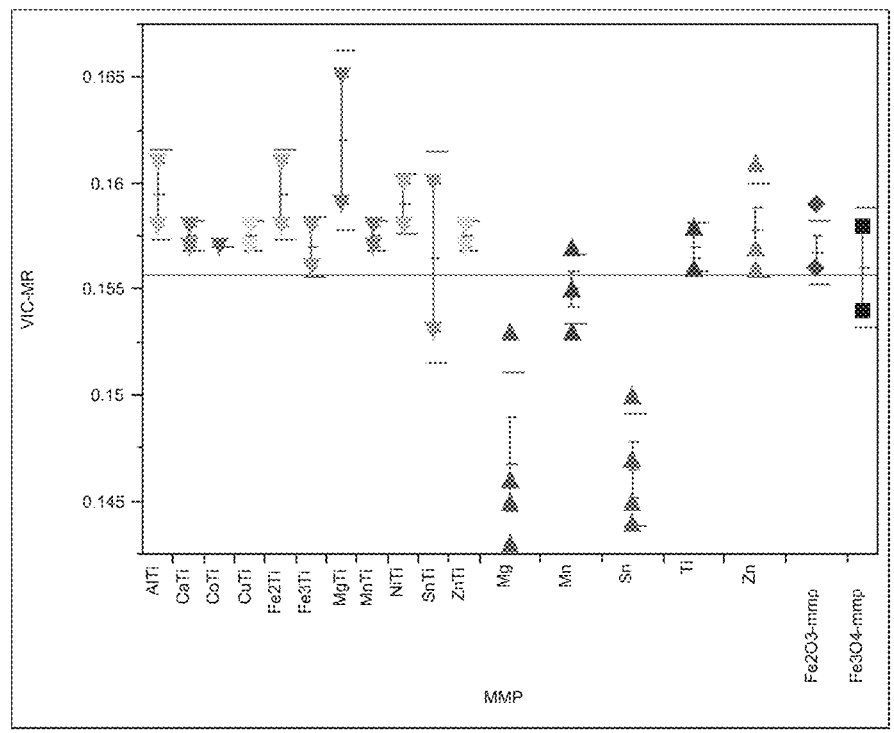

As can be seen FIG. 41, various metal oxides recover the HIV and HBV targets to different degrees. The Al, Ca, Co, Cu, Fez, Mg and Ni oxide particles do not recover either target as well as the other metal oxides. The $Fe_3$ and Ti oxides recover both RNA and DNA, the Mn oxide coated particles recover more DNA than RNA, and the Sn and Zn oxide particles recover more RNA than DNA. The lysis conditions are 58° C. and the sample:lysis volume ratio of 1:1.5 and the phosphate elution was 5 and 20 mM. Other temperatures and other sample volume ratios may change the relative recoveries. The amount of phosphate used to elute the targets may also have an effect on the target recovery.

Additional experiments were conducted to retest metal oxides and metal-titanium oxides. The following particles were tested:
Mg, Mn, Sn, Ti, Zn oxide coated particles.
$Fe_3O_4$ particles
Al—Ti, Ca—Ti, Co—Ti, Cu—Ti, Fe2-Ti, Fe3-Ti, Mg—Ti, Mn—Ti, Ni—Ti, Sn—Ti, and Zn—Ti oxide coated particles.

Figure 44:
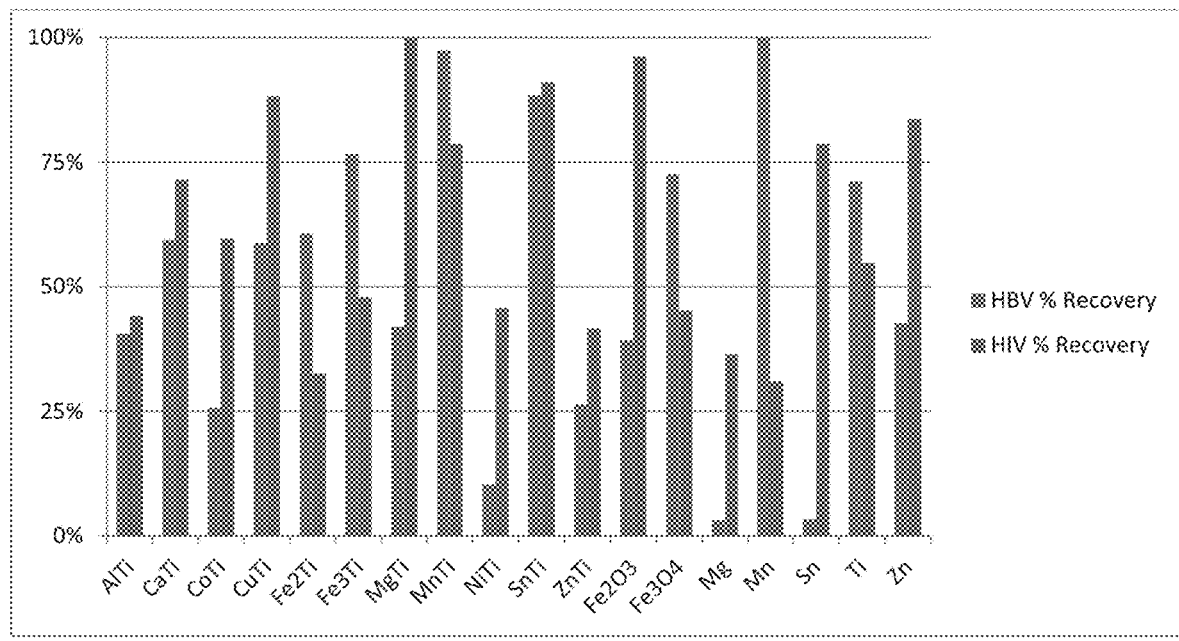
FIG. 44 shows DNA and RNA binding by metal oxide and combinations of metal oxide-titanium oxide coatings on particles.

Particles were prepared and tested as described above. FIGS. 42A-F shows HIV data. FIGS. 43A-F shows HBV data. The metal oxide and metal oxide-titanium oxide precipitate coated particles show differential RNA and DNA binding. To compare the relative recovery of RNA and DNA, the cycle threshold values (CT) were used to calculate the relative recovery of the targets to the particles that gave the best recovery. As is shown in FIG. 44, particular metal oxide and combinations of metal oxide-titanium oxide coatings on the magnetic particles have different DNA and RNA binding properties. All of the oxides tested in this experiment show some nucleic acid recovery. The best oxide coatings for the purification of RNA under the tested conditions are Cu—Ti, Mg—Ti, Sn, and Zn oxides. The best oxide coatings for the purification of DNA under the tested conditions are $Fe_3$—Ti and Mn oxides. The best oxide coatings for the purification of both RNA and DNA under the tested conditions are Mn—Ti and Sn—Ti oxides. The recovery is dependent upon the ability of the metal oxide to bind the nucleic acids under the tested conditions, retain the nucleic acids under the wash conditions and also release the bound nucleic acids under the elution conditions.

| | HBV % Recovery | HIV % Recovery | oxide |
|---|---|---|---|
| AlTi | 41% | 44% | |
| CaTi | 59% | 71% | |
| CoTi | 26% | 60% | |
| CuTi | 59% | 88% | RNA |
| Fe2Ti | 61% | 33% | |
| Fe3Ti | 77% | 48% | DNA |
| MgTi | 42% | 100% | RNA |
| MnTi | 97% | 79% | DNA-RNA |
| NiTi | 10% | 46% | |
| SnTi | 88% | 91% | DNA-RNA |
| ZnTi | 26% | 42% | |
| Fe2O3-mmp | 39% | 96% | |
| Fe3O4-mmp | 73% | 45% | |
| Mg | 3% | 36% | |
| Mn | 100% | 31% | DNA |
| Sn | 3% | 79% | RNA |
| Ti | 71% | 55% | |
| Zn | 43% | 84% | RNA |

All patents, patent application publications, journal articles, textbooks, and other publications mentioned in the specification are indicative of the level of skill of those in the art to which the disclosure pertains. All such publications are incorporated herein by reference to the same extent as if each individual publication were specifically and individually indicated to be incorporated by reference.

What is claimed is:

1. A kit, comprising:
   a) a particle or solid surface comprising or coated with a metal oxide wherein said metal oxide is selected from the group consisting of CuTi, AlTi, CaTi, CoTi, $Fe_2Ti$, $Fe_3Ti$, MgTi, MnTi, NiTi, SnTi and ZnTi; and
   b) a DNA and/or RNA elution buffer.

2. The kit of claim 1, wherein said metal oxide is an anhydride or hydrated form of said metal oxide.

3. The kit of claim 1, wherein said particle has a diameter of 0.5 to 50 um.

4. The kit of claim 1, wherein said particle or solid surface is comprised of a polymer, a magnetic material, a metallic material, an inorganic solid, or a combination thereof.

5. The kit of claim 4, wherein said inorganic solid is silica.

6. The kit of claim 1, wherein said solid surface has a shape selected from the group consisting of planer, acicular, cuboidal, tubular, fibrous, columnar, and amorphous.

7. The kit of claim 6, wherein said DNA and/or RNA elution buffer comprises phosphate.

8. The kit of claim 7, wherein said phosphate is an inorganic or an organophosphate.

9. The kit of claim 7, wherein said phosphate is present in said elution buffer at a concentration of 0.5 to 20 mM.

10. The kit of claim 1, comprising one or more nucleic acid primers.

11. The kit of claim 1, comprising one or more nucleic acids probes.

12. The kit of claim 1, comprising one or more of a lysis buffer, a binding buffer, and a wash buffer.

13. The kit of claim 1, comprising an internal control.

* * * * *